United States Patent
Das et al.

(10) Patent No.: US 6,914,058 B2
(45) Date of Patent: Jul. 5, 2005

(54) ANTIBACTERIAL COMPOUNDS: PROCESS FOR THEIR PREPARATION AND PHARMACEUTICAL COMPOSITIONS CONTAINING THEM

(75) Inventors: Jagattaran Das, Hyderabad (IN); Selavakumar Natesan, Hyderabad (IN); Sanjay Trehan, Hyderabad (IN); Javed Iqbal, Hyderabad (IN); Sitaram Kumar Magadi, Hyderabad (IN); Naga Venkata Srinivasa Rao Mamidi, Hyderabad (IN); Rajagopalan Ramanujam, Hyderabad (IN)

(73) Assignees: Dr. Reddy's Laboratories, Limited, Hyderabad (IN); Dr. Reddy's Laboratories Inc., Hyderabad (IN)

( * ) Notice: Subject to any disclaimer, the term of this patent is extended or adjusted under 35 U.S.C. 154(b) by 164 days.

(21) Appl. No.: 10/342,114

(22) Filed: Jan. 14, 2003

(65) Prior Publication Data

US 2005/0113347 A1 May 26, 2005

(30) Foreign Application Priority Data

Jan. 18, 2002 (IN) ...................................... 42/MAS/2002

(51) Int. Cl.$^7$ .................... C07D 417/10; C07D 405/10; A61K 31/541; A61K 31/5355; A61P 31/04

(52) U.S. Cl. ..................... 514/227.8; 544/58.6; 544/60; 544/132; 546/268.4

(58) Field of Search ............... 544/58.6, 60; 514/227.8

(56) References Cited

PUBLICATIONS

Polymorphism in Pharmaceutical Solids, edited by Harry G. Brittain pp. 1–10, 1992.*
Furuya EY, Lowy FD, abstract of Curr. Opin. Pharmacol. Oct. 2003.; 3(5):464–9.*

* cited by examiner

*Primary Examiner*—Mark L. Berch
*Assistant Examiner*—Kahsay Habte
(74) *Attorney, Agent, or Firm*—Ladas & Parry LLP

(57) ABSTRACT

The present invention relates to novel triazole compounds of formula (I), their derivatives, their analogs, their tautomeric forms, their regioisomers, their rotammers, their stereoisomers, their polymorphs, their pharmaceutically acceptable salts, their pharmaceutically acceptable solvates and pharmaceutical compositions containing them. More particularly, the present invention relates to novel triazoles of the general formula (I)

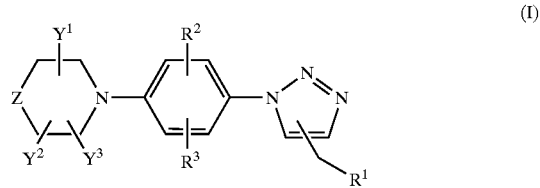

(I)

their derivatives, their analogs, their tautomeric forms, their regioisomers, their rotamers, their stereoisomers, their polymorphs, their pharmaceutically acceptable salts, their pharmaceutically acceptable solvates and pharmaceutical compositions containing them.

56 Claims, No Drawings

ANTIBACTERIAL COMPOUNDS: PROCESS FOR THEIR PREPARATION AND PHARMACEUTICAL COMPOSITIONS CONTAINING THEM

FIELD OF THE INVENTION

The present invention relates to novel triazole compounds of formula (I), their derivatives, their analogs, their tautomeric forms, their regioisomers, their rotamers, their stereoisomers, their polymorphs, their pharmaceutically acceptable salts, their pharmaceutically acceptable solvates and pharmaceutical compositions containing them. More particularly, the present invention relates to novel triazoles of the general formula (I).

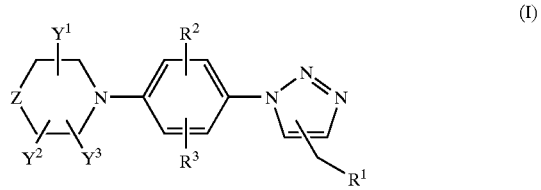

their derivatives, their analogs, their tautomeric forms, their regioisomers, their rotamers, their stereoisomers, their polymorphs, their pharmaceutically acceptable salts, their pharmaceutically acceptable solvates and pharmaceutical compositions containing them.

The present invention also relates to a process for the preparation of the above said novel compounds, their derivatives, their analogs, their tautomeric forms, their regioisoniers, their rotamers, their stereoisomers, their polymorphs, their pharmaceutically acceptable salts, their pharmaceutically acceptable solvates and pharmaceutical compositions containing them.

The present invention also relates to novel intermediates, methods for their preparation and their use in the preparation of compounds of formula (I).

BACKGROUND OF THE INVENTION

Since the discovery of penicillin, pharmaceutical companies have produced more than one hundred antibacterial agents to combat a wide variety of bacterial infections. In the past several years, there has been rapid emergence of bacterial resistance to several of these antibiotics. The multidrug resistance among these bacterial pathogens may also be due to mutation leading to more virulent clinical isolation, the most disturbing milestone has been the acquisition of resistance to vancomycin, an antibiotic generally regarded as the agent of last resort for serious Gram-positive infections. This growing multidrug resistance has recently rekindled interest in the search for new structural class of antibiotic that inhibit or kill these bacteria possibly by novel mechanisms.

A problem of larger dimension is the increasing incidence of the more virulent, methicillin-resistant *Staphylococcus aureas* (MRSA) among clinical isolates found worldwide. As with vancomycin resistant organisms, many MRSA strains are resistant to most of the known antibiotics, but MRSA strains have remained sensitive to vancomycin. However, in view of the increasing reports of vancomycin resistant clinical isolates and growing problem of bacterial resistance, there is an urgent need for new molecular entities effective against the emerging and currently problematic Gram-positive organisms.

Recently, several oxazolidinones have been discovered, which inhibit protein synthesis by binding to the 50S-ribosomal subunit which is close to the site to which chloramphenicol and lincomycin bind but their mode of action is mechanistically distinct from these two antibiotics.

Various 1,2,3-triazoles, 1,2,4-triazoles and benzotriazoles have been reported to show various biological activities and have therefore found applications in medicinal chemistry. The literature survey shows the use of 1,2,3-triazoles, for the treatment of neuropathic pain and associated hyperalgesia, including trigeminal and herpectic neuralgia, diabetic neuropathic pain, migraine, causalgia and deafferentation syndromes such as brachial plexus avulsion, an anticoccidiostat, as antiproliferativc agents, for antimetastatic activity in a model of ovarian cancer progression, for anti-inflammatory effect, controlling activity against noxious organisms, for the treatment of ischemia, anti-human immunodeficiency virus activity etc.

However, there are no reports of 1,2,3-triazole derivatives of the present invention being used for treating bacterial infections, specifically against multidrug resistant strains.

The new class of triazoles of the present invention is useful for the treatment of a number of resistant and sensitive gram-positive strains both in vitro and in vivo.

(a) Chem. Pharm. Bull. 48(12), 1935–1946 (2000) discloses the triazoles of formula (ia) and (ib), which are reported as antifungal agents,

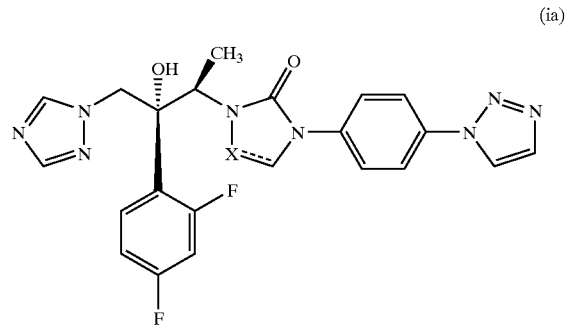

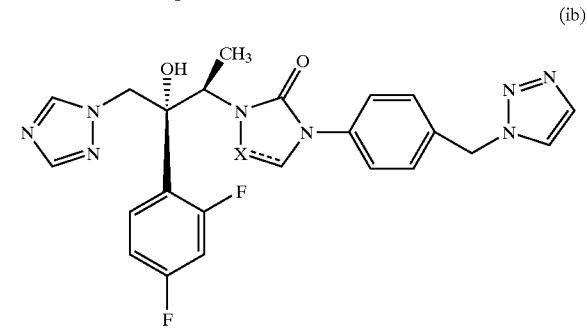

where X represents N, CH or $CH_2$.

U.S. Pat. No. 6,054,471 discloses fluorinated triazoles of the formula (ii), which are reported for the treatment of neuropathic pain and associated hyperalgesia, including trigeminal and herpectic neuralgia, diabetic neuropathic pain, migraine, causalgia and deafferentation syndromes such as brachial plexus avulsion,

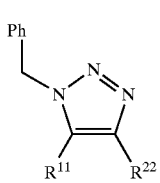

(ii)

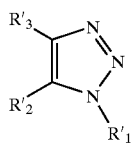

(v)

where R'₁ represents

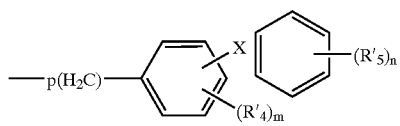

where Ph is an o-fluorinated phenyl group which may be additionally substituted by 1 or 2 halogen atoms selected from fluorine and chlorine; $R^{11}$ is hydrogen, carbamoyl, N—($C_2$–$C_5$) alkanoylcarbamoyl or N,N-di-($C_1$–$C_4$) alkylcarbamoyl; $R^{21}$ is carbamoyl, N—($C_2$–$C_5$) alkanoyl-carbamoyl or N,N-di-($C_1$–$C_4$)alylcarbamoyl.

An example of this class of compounds is shown in formula (iia),

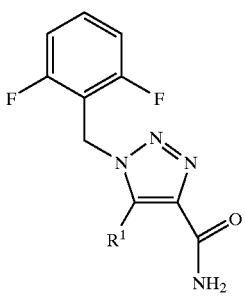

(iia)

(c) J. Med. Chem., 2843, 1991 discloses compound of formula (iii), which is an anticoccidiostat and also been found to have antiproliferative activity in several disease models and to posses antimetastatic activity in a model of ovarian cancer progression,

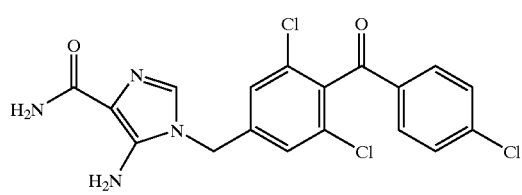

(iii)

(d) J. Heterocycl. Chem., 609, 1989 discloses compound of formula (iv), which is reported for anti-inflammatory effects,

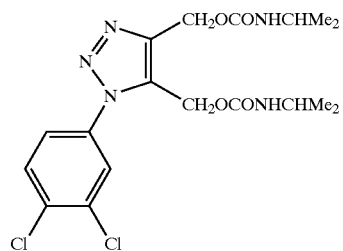

(iv)

(e) EPO publication no 0304221 A2 discloses compounds of formula (v), which are reported as antiproliferative reagents, wherein p is 0 to 2; m is 0 to 4; and n is 0 to 5; X is O, S, SO, $SO_2$, CO, CHCN, $CH_2$ or C=$NR_6$ where $R_6$ is hydrogen, loweralkyl, hydroxy, loweralkoxy, amino loweralkylamino. diloweralkylamino or cyano, and, R'₄ and R'₅ are independently halogen, cyano, trifluoromethyl, loweralkanoyl, nitro, loweralkyl, loweralkoxy, carboxy, carbalkoxy, trifluoromethoxy, acetamido, loweralkylthio, loweralkylsulfonyl, trichlorovinyl, trifluoromethylthio. trifluoromethylsuifinyl, or trifluoromethylsulfonyl;

R'₂ is amino, mono or diloweralkylamino, acetamido, acetimido, ureido, formamido, or guanidino; and R'₃ is carbamoyl, cyano. carbazoyl, amidino or N-hydroxycarbamoyl.

An example of this class of compounds is shown in formula (va),

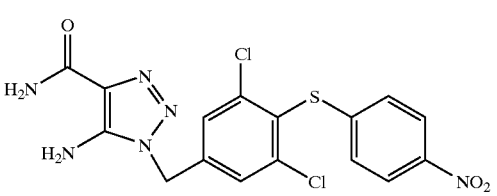

(va)

SUMMARY OF THE INVENTION

With an objective to develop novel compounds effective against a number of human and veterinary pathogens, including gram-positive aerobic bacteria such as MRSA, streptococci and enterococci as well as anaerobic organisms such as *Bacteroides* spp, *Clostridia* spp. species and acid-fast organisms such as *Mycobacterium tuberculosis, Mycobacterium avium* and *Mycobacterium* spp., we focus our research to develop new compounds effective against the above mentioned organisms. Efforts in this direction have led to the discovery of compounds having general formula (I) as defined above. The compounds of this invention can be used to treat infections caused by any number of microorganisms or pathogens including but not limited to gram-positive aerobic bacteria, anaerobic organism, acid-fast organism or gram-negative bacteria. The compounds of the present invention can also be used to prevent infections caused by microorganisms or other pathogens in patients that are at risk of developing an infection. Such patients include but are not limited to patients who are in a hospital, post or pre-surgical or immuno-compromised.

The present invention provides novel 1,2,3-triazole derivatives of the general formula (I) as defined above and their derivatives, their analogs, their tautomeric forms, their regioisomers, their rotamers, their stereoisomers, their polymorphs, their pharmaceutically acceptable salts, their pharmaceutically acceptable solvates and pharmaceutical compositions containing them, or their mixtures having enhanced activities, without toxic effect or with reduced toxic effect.

The present invention also provides a process for the preparation of novel 1,2,3-triazole derivatives of the formula (I) as defined above and their derivatives, their analogs, their tautomeric forms, their regioisomers, their rotamers, their stereoisomers, their polymorphs and their pharmaceutically acceptable salts.

An aspect of the present invention is to provide pharmaceutical compositions containing compounds of the general formula (I), their analogs, their derivatives, their tautomers, their stereoisomers, their rotamers, their regioisomers, their polymorphs, their salts, solvates or their mixtures in combination with suitable carriers, solvents, diluents and other media normally employed in preparing such compositions.

DETAILED DESCRIPTION OF THE INVENTION

The present invention relates to compounds having the general formula (I),

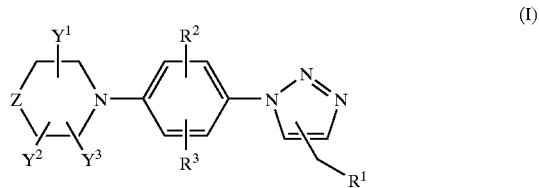

(I)

where $R^1$ represents halo, azido, thioalcohol, isothiocyanate, isoindole-1,3-dione, $NHR^4$, where $R^4$ represents hydrogen, substituted or unsubstituted groups selected from $(C_1-C_{10})$ alkyl, $(C_1-C_{10})$acyl, thio$(C_1-C_{10})$acyl, $(C_1-C_{10})$ alkoxycarbonyl, $(C_3-C_{10})$cycloalkoxythiocarbonyl, $(C_2-C_{10})$alkenyloxycarbonyl, $(C_2-C_{10})$alkenylcarbonyl, heteroaryl, aryloxycarbonyl, heteroarylcarbonyl, heteroarylthiocarbonyl, $(C_1-C_{10})$alkoxythiocarbonyl, $(C_2-C_{10})$alkenyloxythiocarbonyl, aryloxythiocarbonyl, —C(=O)—C(=O)—$(C_1-C_{10})$alkyl, —C(=O)—C(=O)-aryl, —C(=O)—C(=O)—$(C_1-C_{10})$alkoxy, —C(=O)—C(=O)-aryloxy, —C(=O)—C(=S)—$(C_1-C_{10})$alkyl, —C(=O)—C(=S)-aryl, —C(=S)—S—$(C_1-C_{10})$alkyl, —C(=S)—NH$_2$, —C(=S)—NH—$(C_1-C_{10})$alkyl, —C(=S)—N—$((C_1-C_{10})$alkyl)$_2$, —C(=S)—NH—$(C_2-C_{10})$alkenyl, —C(=S)—C(=O)—$(C_1-C_{10})$alkoxy, —C(=S)—C(=O)-aryloxy, —C(=S)—O—C(=O)—$(C_1-C_{10})$alkyl, —C(=S)—C(=S)—$(C_1-C_{10})$alkyl, —C(=S)—C(=S)-aryl, —C(=S)—NH—C(=O)-aryl, —C(=S)—NH-aralkyl, —C(=S)—NH-heteroaralkyl, —C(=NH)—NH$_2$, —C(=NH)—$(C_1-C_{10})$alkyl, —C(=NH)-aryl, —S(O)$_2$$(C_1-C_{10})$alkyl, —S(O)$_2$aryl, thiomorpholinylthiocarbonyl, pyrrolidinylthiocarbonyl or —C(=S)—N(R'R"), where R' and R" together form a substituted or unsubstituted 5 or 6 member heterocycle ring containing nitrogen and optionally having one or two additional hetero atoms selected from O, S or N; OR$^5$ where $R^5$ represents hydrogen, substituted or substituted groups selected from $(C_1-C_{10})$acyl, heteroaryl, —S(O)$_2$$(C_1-C_{10})$alkyl, —S(O)$_2$aryl or —C(=S)—S—$(C_1-C_{10})$alkyl; N(R$^6$)$_2$, where —(R$^6$)$_2$ together represent a substituted or unsubstituted 5 or 6 member heterocycle ring containing nitrogen and optionally having one or two additional hetero atoms selected from O, S or N; $R^2$ and $R^3$ may be same or different and independently represent hydrogen, halogen atom, substituted or unsubstituted $(C_1-C_{10})$alkyl group, halo$(C_1-C_{10})$ alkyl, cyano, nitro, SR$^a$, NR$^a$, OR$^a$ where R$^a$ represents substituted or unsubstituted $(C_1-C_{10})$alkyl group; Z represents S, O, —S(O)$_n$ where n represents 1–2, —C(R$^p$)$_2$ where R$^p$ represents hydrogen or —(R$^p$)$_2$ together represent a substituted or unsubstituted 5 or 6 membered cyclic ring optionally having one or two hetero atoms selected from oxygen atom, —S=NR, —S(=O)=NR wherein R represents hydrogen or substituted or unsubstituted $(C_1-C_{10})$ alkyl; $Y^1$, $Y^2$ and $Y^3$ may be same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$ alkylcarbonylamino$(C_1-C_{10})$alkyl, arylcarbonylamino $(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$ alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ may represent =O, =S, substituted or unsubstituted =NOH; or

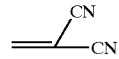

group; its derivatives, its analogs, its tautomeric forms, its stereoisomers, its polymorphs, it rotamers, its regioisomers, its pharmaceutically acceptable salts or its pharmaceutically acceptable solvates.

Suitable groups represented by $R^4$ are described as $(C_1-C_{10})$alkyl such as methyl, ethyl, propyl, isopropyl, butyl, isobutyl, tert-butyl and the like, the $(C_1-C_{10})$alkyl group may be substituted; $(C_1-C_{10})$acyl group such as —C(=O)H, —C(=O)CH$_3$, —C(=O)CH$_2$CH$_3$, —C(=O)(CH$_2$)$_2$CH$_3$, —C(=O)(CH$_2$)$_3$CH$_3$, —C(=O)(CH$_2$)$_4$CH$_3$, —C(=O)(CH$_2$)$_5$CH$_3$, —C(=O)Ph and the like, the $(C_1-C_{10})$acyl group may be substituted; thio$(C_1-C_{10})$acyl group such as —C(=S)H, —C(=S)CH$_3$, —C(=S) CH$_2$CH$_3$, —C(=S)Ph and the like, the thio$(C_1-C_{10})$acyl group maybe substituted; $(C_1-C_{10})$alkoxycarbonyl group containing $(C_1-C_{10})$alkyl group which may be linear or branched such as methoxycarbonyl, ethoxycarbonyl, propoxycarbonyl, isopropoxycarbonyl and the like, the $(C_1-C_{10})$alkoxycarbonyl group may be substituted; $(C_3-C_{10})$cycloalkoxythiocarbonyl such as cyclopropoxythiocarbonyl, cyclobutoxythiocarbonyl and the like, the $(C_3-C_{10})$cycloalkoxythiocarbonyl may be substituted; $(C_2-C_{10})$alkenylcarbonyl such as ethenylcarbonyl, propenylcarbonyl, butenylcarbonyl and the like, the $(C_2-C_{10})$alkenylcarbonyl may be substituted; heteroaryl group such as pyridyl, furyl, thiophenyl, benzothiazoyl, purinyl, benzimidazoyl, pyrimidinyl, tetrazolyl and the like, the heteroaryl group may be substituted; heteroarylcarbonyl such as pyridylcarbonyl, furylcarbonyl, thiophenylcarbonyl, benzothiazoylcarbonyl, benzimidazoylcarbonyl, pyrimidinylcarbonyl, pyridazinecarbonyl, pyrimidinecarbonyl, pyrazinecarbonyl, tetrazolylcarbonyl and the like, the heteroarylcarbonyl group may be substituted, heteroarylthiocarbonyl such as pyridylthiocarbonyl, furylthiocarbonyl, thilophenylthiocarbonyl, benzothiazoylthiocarbonyl, benzimidazoylthiocarbonyl, pyrimidinylthiocarbonyl, pyridazinethiocarbonyl, pyrimidinethiocarbonyl, pyrazinethiocarbonyl, tetrazolylthiocarbonyl and the like, the heteroarylthiocarbonyl may be substituted, $(C_2–C_{10})$ alkenyloxycarbonyl group such as ethenyloxycarbonyl, propenyloxycarbonyl, butenyloxycarbonyl and the like, the $(C_2–C_{10})$alkenyloxycarbonyl may be substituted; aryloxycarbonyl group such as phenoxycarbonyl, benzyloxycarbonyl group and the like, the aryloxycarbonyl group may be substituted; $(C_1–C_{10})$alkoxythiocarbonyl group such as $CH_3O—C(=S)—$, $C_2H_5O—C(=S)—C_3H_7O—C(=S)—$ and the like, $(C_1–C_{10})$alkoxythiocarbonyl group may be substituted; $(C_2–C_{10})$alkenyloxythiocarbonyl group such as ethenyloxythiocarbonyl, propenyloxythiocarbonyl, butenyloxythiocarbonyl and the like, the $(C_2–C_{10})$ alkenyloxythiocarbonyl group may be substituted; aryloxythiocarbonyl group such as (plienyl)$O—C(=S)—$, (benzyl)$O—C(=S)—$ and the like, which may be substituted; $—C(=O)—C(=O)—(C_1–C_{10})$alkyl group such as $—C(=O)—C(=O)$methyl, $—C(=O)—C(=O)$ethyl, $—C(=O)—C(=O)$propyl and the like, which may be substituted; $—C(=O)—C(=O)$-aryl group such as $—C(=O)—C(=O)$phenyl, $—C(=O)—C(=O)$naphthyl and the like, which may be substituted; $—C(=O)—C(=O)—(C_1–C_{10})$alkoxy group such as $—C(=O)—C(=O)$methoxy, $—C(=O)—C(=O)$ethoxy, $—C(=O)—C(=O)$propyloxy and the like, which may be substituted; $—C(=O)—C(=O)$-aryloxy group such as $—C(=O)—C(=O)$phenyloxy, $—C(=O)—C(=O)$benzyloxy, which may be substituted; $—C(=O)—C(=S)—(C_1–C_{10})$alkyl group such as $—C(=O)—C(=S)$-methyl, $—C(=O)—C(=S)$-ethyl, $—C(=O)—C(=S)$-propyl, $—C(=O)—C(=S)$-butyl and the like, which may be substituted; $—C(=O)—C(=S)$-aryl group such as $—C(=O)—C(=S)$-phenyl, $—C(=O)—C(=S)$-naphthyl and the like, which may be substituted; $—(C=S)—S—(C_1–C_{10})$alkyl such as $—(C=S)—S$-methyl, $—(C=S)—S$-ethyl, $—(C=S)—S$-propyl and the like, which may be substituted; $—(C=S)—NH_2$, which may be substituted; $—(C=S)—NH—(C_1–C_{10})$alkyl such as $—(C=S)—NH$-methyl, $—(C=S)—NH$-ethyl, $—(C=S)—NH$-propyl and the like, which may be substituted; $—C(=S)—N—((C_1–C_6)alkyl)_2$ such as $—C(=S)—N$-(methyl)$_2$, $—C(=S)—N$-(ethyl)$_2$, $—C(=S)—N$-(propyl)$_2$ and the like, which may be substituted; $—C(=S)—NH—(C_2–C_{10})$alkenyl such as $—C(=S)—NH$-ethenyl, $—C(=S)—NH$-propenyl, $—C(=S)—NH$-butenyl and the like, which may be substituted; $—(C=S)—(C=O)—(C_1–C_{10})$alkoxy such as $—(C=S)—(C=O)$-methoxy, $—(C=S)—(C=O)$-ethoxy, $—(C=S)—(C=O)$-propoxy and the like, which may be substituted; $—(C=S)—(C=O)$-aryloxy such as $—(C=S)—(C=O)$-phenyloxy, $—(C=S)—(C=O)$-naphthyloxy and the like, which may be substituted; $—C(=S)—O—(C=O)—(C_1–C_{10})$alkyl such as $—C(=S)—O—(C=O)$-methyl, $—C(=S)—O—(C=O)$-ethyl, $—C(=S)—O—(C=O)$-propyl and the like, which may be substituted; $—C(=S)—C(=S)—(C_1–C_{10})$alkyl group such as $—C(=S)—C(=S)$methyl, $—C(=S)—C(=S)$ethyl, $—C(=S)—C(=S)$propyl and the like, which may be substituted; $—C(=S)—C(=S)$aryl group such as $—C(=S)—C(=S)$phenyl, $—C(=S)—C(=S)$naphthyl and the like, which may be substituted; $—C(=S)—NH—C(=O)$-aryl group such as $—C(=S)—NH—C(=O)$-phenyl, $—C(=S)—NH—C(=O)$-naphthyl and the like, $—C(=S)—NH—C(=O)$-aryl group may be substituted; $—C(=S)—NH$-aralkyl group such as $—C(=S)—NH$-benzyl, $—C(=S)—NH$-phenethyl, $—C(=S)—NH—C_6H_5CH_2CH_2CH_2$, $—C(=S)—NH$-naphthylmethyl and the like, $—C(=S)—NH$-aralkyl group may be substituted; $—C(=S)—NH$-heteroaralkyl such as pyridinemethyl, furanmethyl, thiophenylenemethyl, benzothiazolemethyl, benzimidazolemethyl, pyrimidinemethyl, pyrimidinemethyl, pyrazinemethyl, tetrazolemethyl and the like, where $—C(=S)—NH$-aralkyl group may be substituted; $—C(=NH)—NH_2$, which may be substituted; $—C(=NH)—(C_1–C_{10})$alkyl such as $—C(=NH)$-methyl, $—C(=NH)$-ethyl, $—C(=NH)$-propyl and the like, which may be substituted; $—C(=NH)$-aryl such as $—C(=NH)$-phenyl, $—C(=NH)$-naphthyl and the like, which may be substituted; $S(O)_2—(C_1–C_{10})$alkyl such as $S(O)_2$-methyl, $S(O)_2$-ethyl, $S(O)_2$-propyl, $S(O)_2$-isopropyl, $S(O)_2$-butyl, $S(O)_2$-isobutyl and the like, which may be substituted; $S(O)_2$-aryl such as $S(O)_2$-phenyl, $S(O)_2$-naphthyl and the like, which may be substituted; thiomorpholinylthiocarbonyl, which may be substituted; pyrrolidinylthiocarbonyl, which may be substituted; or $—C(=S)—N(R'R")$ where R'R" are as defined above.

Suitable groups represented by $R^5$ may be described as $(C_1–C_{10})$acyl group such as $—C(=O)H$, $—C(=O)CH_3$, $—C(=O)CH_2CH_3$, $—C(=O)(CH_2)_2CH_3$, $—C(=O)(CH_2)_3CH_3$, $—C(=O)(CH_2)_4CH_3$, $—C(=O)(CH_2)_5CH_3$, $—C(=O)Ph$ and the like, the $(C_1–C_{10})$acyl group may be substituted; heteroaryl group such as pyridyl, furyl, thiophenyl, benzothiazoyl, purinyl, benzimidazoyl, pyrimidinyl, tetrazolyl and the like, the heteroaryl group may be substituted; $S(O)_2—(C_1–C_{10})$alkyl such as $S(O)_2$-methyl, $S(O)_2$-ethyl, $S(O)_2$-propyl, $S(O)_2$-isopropyl, $S(O)_2$-butyl, $S(O)_2$-isobutyl and the like, which may be substituted; $S(O)_2$-aryl such as $S(O)_2$-phenyl, $S(O)_2$-naphthyl and the like, which may be substituted; $—(C=S)—S—(C_1–C_{10})$alkyl such as $—(C=S)—S$-methyl, $—(C=S)—S$-ethyl, $—(C=S)—S$-propyl and the like, which may be substituted.

A 5 or 6 member heterocycle ring containing nitrogen, optionally having one or two additional heteroatoms selected from oxygen, nitrogen or sulfur, formed by R'&R" and/or heterocyclic ring formed by $—(R^6)_2$ is selected from pyrrolidinyl, pyrrolyl, morpholinyl, thiomorpholinyl, benzothiazole, benzoimidazolyl, pyridinyl, pyridazinyl, pyrimidinyl, pyrazinyl and the like, the heterocycle may be substituted.

When the groups represented by $R^4$, $R^{4a}$, $R^{4b}$, $4^{4c}$, $R^{4d}$, $R^e$, R, $R^7$ and heterocycles formed by R'and R" and heterocycles formed by $—(R^6)_2$ are substituted, the substituents may be selected from halogen atom such as chlorine, fluorine, bromine and iodine; hydroxy, amino, cyano, nitro, $(C_1–C_{10})$alkyl, which is as defined as earlier; hydroxy $(C_1–C_{10})$alkyl, in which $(C_1–C_{10})$alkyl groups is as defined earlier; $(C_1–C_{10})$alkoxy group such as methoxy, ethoxy, propoxy and the like; $=O$, $=S$, aryl group such as phenyl, naphthyl and the like, hydroxyaryl such as hydroxyphenyl, hydroxynaphthyl and the like, pyridyl, mono($C_1–C_{10}$) alkylamino such as methylamino, ethylamino, propylamino and the like; di($C_1–C_{10}$)alkylamino such as dimethylamino, diethylamino, dipropylamino and the like; $(C_1–C_{10})$ alkoxycarbonyl group such as methoxy carbonyl, ethoxycarbonyl, propoxycarbonyl, butoxycarbony, tert-butoxycarbonyl(BOC) and the like; $(C_1–C_{10})$alkoxyaryl group such as methoxyaryl, ethoxyaryl, propoxyaryl, isopropoxyaryl, butoxyaryl and the like, where aryl group is as defined above or carboxylic acid or its derivatives selected from amides and esters such as $CONH_2$, CONHMe, $CONMe_2$, CONHEt, $CONEt_2$, CONHPh, $COOCH_3$, $COOC_2H_5$ or $COOC_3H_7$.

Suitable groups represented by $R^2$ and $R^3$ may be selected from hydrogen, halogen atom such as fluorine, chlorine or bromine; substituted or unsubstituted $(C_1–C_{10})$alkyl group such as methyl, ethyl, n-propyl, isopropyl, n-butyl, isobutyl, t-butyl, n-pentyl, iso-pentyl, n-hexyl and the like; halo($C_1$–$C_{10}$)alkyl group such as halomethyl, haloethyl, halopropyl, trihalomethyl and the like, wherein the halo group is selected from fluorine, chlorine, bromine or iodine; cyano, nitro; $SR^a$, $NR^a$, $OR^a$ where $R^a$ represents substituted or unsubstituted ($C_1$–$C_{10}$)alkyl group such as methyl, ethyl, propyl, isopropyl and the like.

Suitable groups represented by Z may be selected from S, O, $S(O)_n$ where n represents 1–2, S=NR, —S(=O)=NR wherein R represents hydrogen or substituted or unsubstituted ($C_1$–$C_{10}$)alkyl such as methyl, ethyl, n-propyl, isopropyl, n-butyl, iso-butyl, t-butyl and the like, —$C(R^P)_2$ where $R^P$ represents hydrogen or —$(R^P)_2$ together represent a substituted or unsubstituted 5 or 6 membered cyclic ring having one or two hetero atoms selected from oxygen atoms, the heterocyles formed may be selected from tetrahydrofuran, [1,3]dioxolane, [1,3]dioxane and the like.

Suitable substitutents on $R^2$, $R^3$, $R^5$, $R^a$ and cyclic rings formed by —$(R^P)_2$ are selected from hydroxy, halogen, nitro, amino, ($C_1$–$C_{10}$)alkyl, ($C_1$–$C_{10}$)alkoxy, =O, =S, cyano group, or carboxylic acid or its derivatives. These groups are as defined above.

Suitable groups represented by $Y^1$, $Y^2$ and $Y^3$ are selected from hydrogen, cyano, nitro, formyl, hydroxy, amino, halogen such as fluorine, chlorine, bromine or iodine, substituted or unsubstituted ($C_1$–$C_{10}$)alkyl such as methyl, ethyl, n-propyl, isopropyl, n-butyl, iso-butyl, t-butyl and the like, which may be substituted; hydroxy($C_1$–$C_{10}$)alkyl such as hydroxymethyl, hydroxyethyl, hydroxypropyl and the like, which may be substituted; ($C_1$–$C_{10}$)alkoxy($C_1$–$C_{10}$)alkyl group such as methoxymethyl, methoxyethyl, ethoxyethyl, ethoxymethyl, methoxypropyl, propoxymethyl, propoxyethyl and the like, which may be substituted; ($C_1$–$C_{10}$) alkoxycarbonyl group such as methoxycarbonyl, ethoxycarbonyl and the like, which may be substituted; carboxy ($C_1$–$C_{10}$)alkyl such as $CH_3$—COOH, $CH_3$—$CH_2$—COOH and the like, which may be substituted; ($C_1$–$C_{10}$) alkylsulfonyl group such as methylsulfonyl, ethylsulfonyl and the like, which may be substituted; ($C_1$–$C_{10}$) alkylcarbonylamino($C_1$–$C_{10}$)alkyl groups such as methylcarbonylaminomethyl, ethylcarbonylaminomethyl, methylcarbonylaminoethyl and the like, which may be substituted; arylcarbonylamino($C_1$–$C_{10}$)alkyl such as phenylcarbonylaminomethyl, phenylcarbonylaminoethyl and the like, which may be substituted; ($C_1$–$C_{10}$) alkylcarbonyloxy($C_1$–$C_{10}$)alkyl group such as methylcarbonyloxymethyl, ethylcarbonylxoymethyl, methylcarbonyloxyethyl, propylcarbonyloxymethyl, propylcarbonyloxyethyl, propylcarbonyloxypropyl and the like, which may be substituted; amino($C_1$–$C_{10}$)alkyl such as aminomethyl, aminoethyl, aminopropyl and the like, which may be substituted; mono($C_1$–$C_{10}$)alkylamino such as methylamino, ethylamino, propylamino and the like, which may be substituted; di($C_1$–$C_{10}$)alkylamino such as dimethylamino, diethylamino, dipropylamino and the like, which may be substituted; arylamino such as phenylamino, benzylamino and the like, which may be substituted; ($C_1$–$C_{10}$)alkoxy group such as methoxy, ethoxy, propoxy, isopropoxy and the like, which may be substituted; aryl group such as phenyl, naphthyl and the like, which may be substituted; aryloxy group such as phenoxy, naphthyloxy and the like, the aryloxy group may be substituted; aralkyl such as benzyl, phenethyl, $C_6H_5CH_2CH_2CH_2$, naphthylmethyl and the like, the aralkyl group may be substituted; heteroaryl groups such as pyridyl, thienyl, furyl, pyrrolyl, oxazolyl, thiazolyl, pyrazolyl, imidazolyl, oxadiazolyl, tetrazolyl, benzopyranyl, benzofuranyl and the like, which may be substituted; heteroaralkyl such as imidazolemethyl, imidazoleethyl, pyridylmethyl, furyl methyl, oxazolemethyl, imidazolyl and the like, which may be substituted; heterocyclyl group such as pyrrolidinyl, piperidinyl, morpholinyl, piperazinyl and the like; heterocycloalkyl groups such as pyrrolidinemethyl, piperidinemethyl, morpholinemethyl, piperazinemethyl and the like, which may be substituted. Any of $Y^1$, $Y^2$ or $Y^3$ may also represent =O, =S, substituted or unsubstituted =NOH; or

group.

When the groups represented by $Y^1$, $Y^2$ and $Y^3$ are substituted, the substituents may be selected fiom hydroxy, nitro, cyano, amino, teri-butyldimetliylsilyloxy (TBSO), halogen atom, ($C_1$–$C_{10}$)alkyl, ($C_1$–$C_{10}$)alkoxy, cyclo ($C_3$–$C_{10}$)alkyl, aryl, benzyloxy, acyl or acyloxy group such as formyloxy, acetyloxy and the like. The remaining groups are as defined above.

When the groups representcd by $R^c$ and $R^d$ as defined below are substituted, the substituents are selected from halogen, hydroxy, nitro, amino, cyano, ($C_1$–$C_{10}$)alkyl or ($C_1$–$C_{10}$)alkoxy. ($C_1$–$C_{10}$)alkyl and ($C_1$–$C_{10}$)alkoxy are as defined above.

Pharmaceutically acceptable salts forming part of this invention include salts derived from inorganic bases such as Li, Na, K, Ca, Mg, Fe, Cu, Zn, Mn; salts of organic bases such as N,N'-diacetylethylenediamine, betaine, caffeine, 2-diethylaminoethanol, 2-dimethylaminoethanol, N-ethylmorpholinc, N-ethylpiperidine, glucamine, glucosamine, hydrabamine, isopropylamine, methylglucamine, morpholine, piperazine, piperidine, procaine, purines, theobroininc, triethylamine, trimethylamine, tripropylamine, trometlhaminle, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, ornithine, lysine, arginine, scrine, threonine, phenylalanine; unnatural amino acids such as D-isomers or substituted amino acids; guanidine, substituted guanidine wherein the substituents are selected from nitro, amino, alkyl such as methyl, ethyl, propyl and the like; alkenyl such as ethenyl, propenyl, butenyl and the like; alkynyl such as ethynyl, propynyl and the like; ammonium or substituted ammonium salts and aluminum salts. Salts may include acid addition salts where appropriate which are, sulphates, nitrates, phosphates, perchlorates, borates, halides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to this invention include:

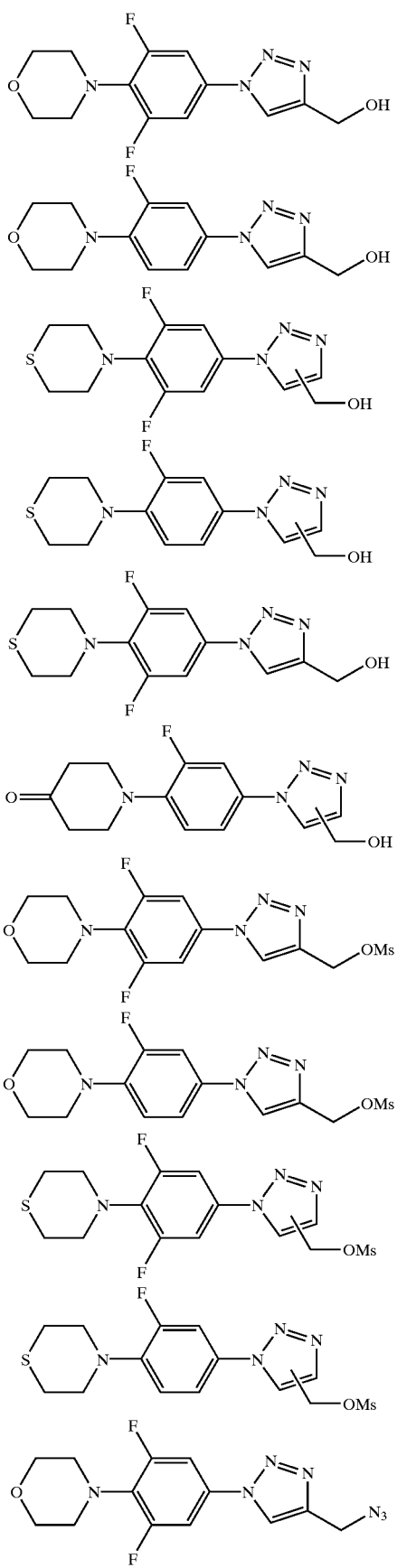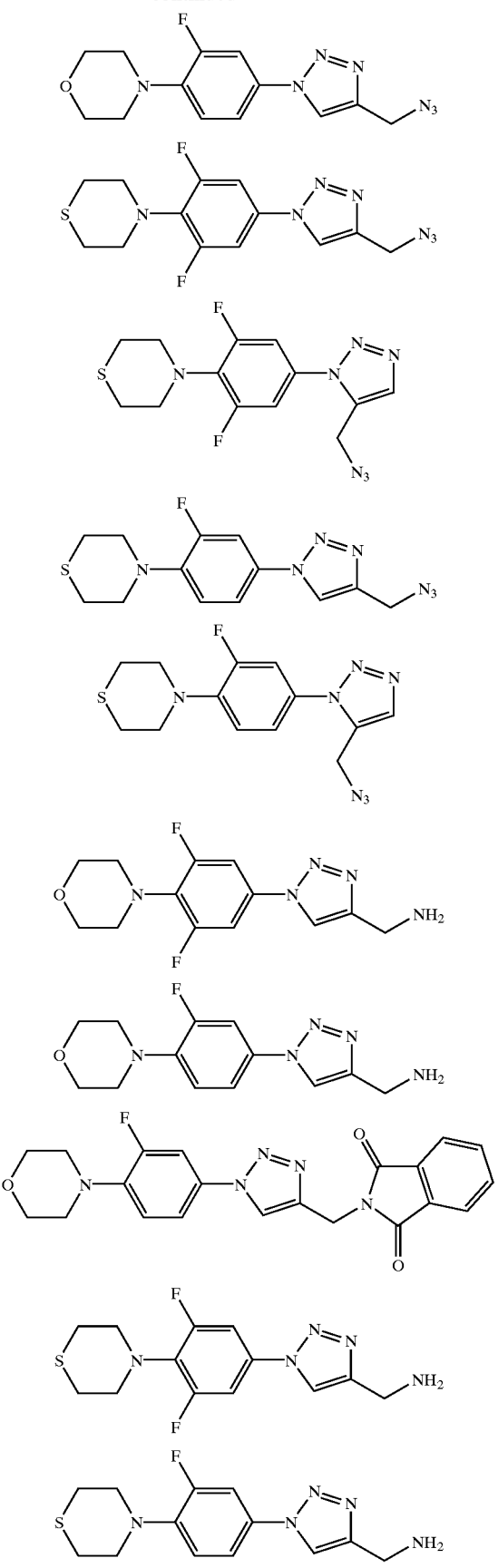

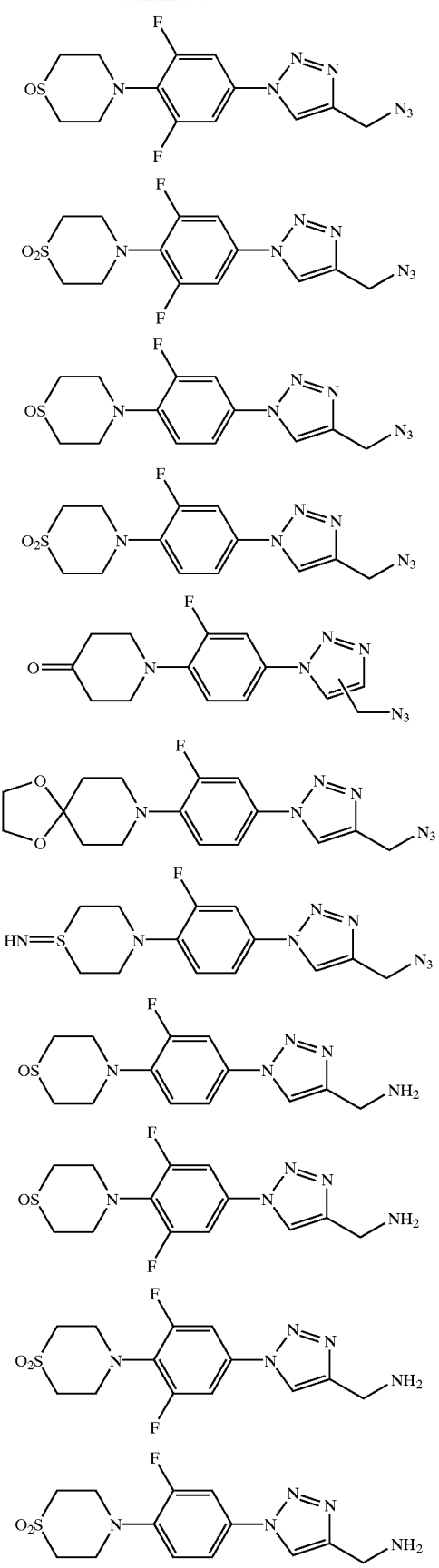
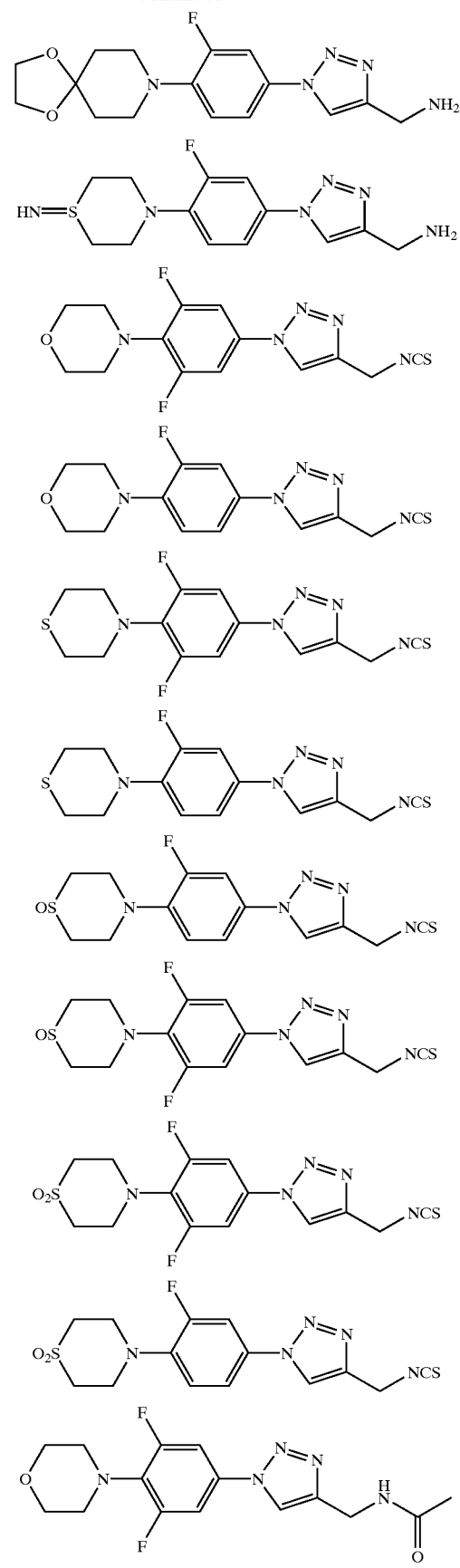

-continued
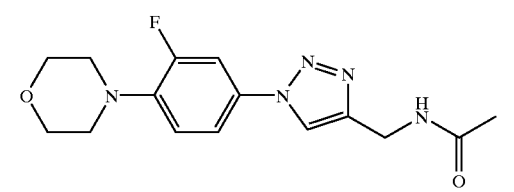
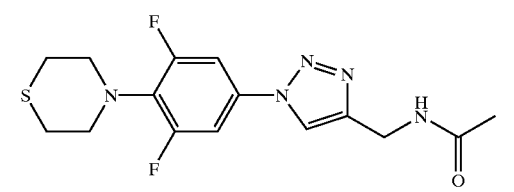
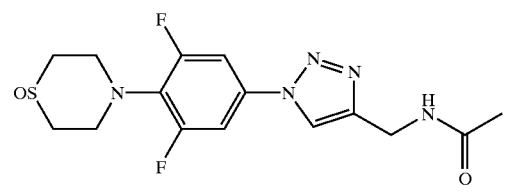
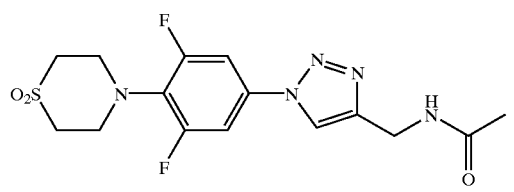
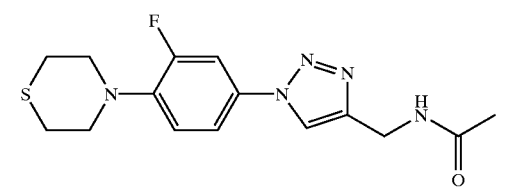
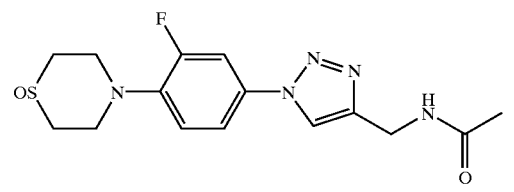
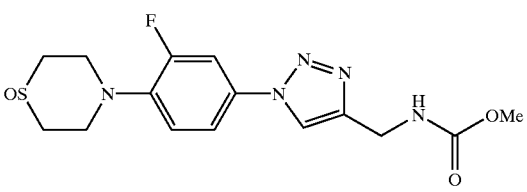
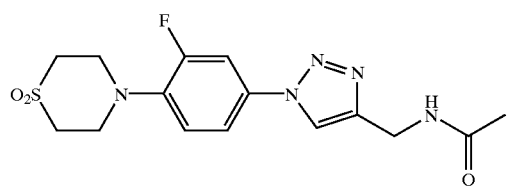
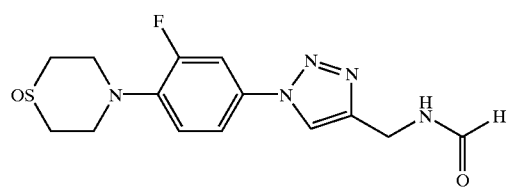
-continued
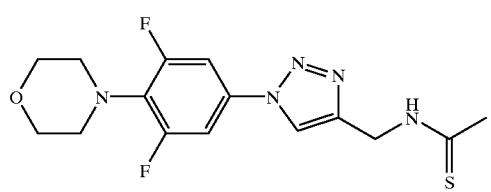
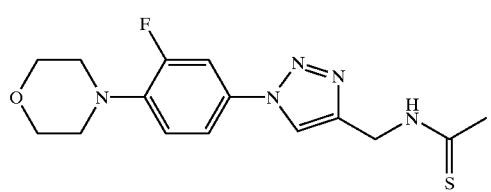
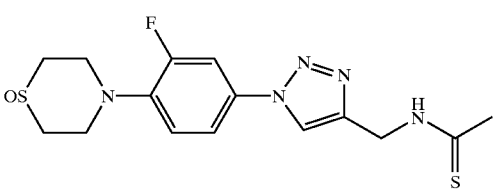
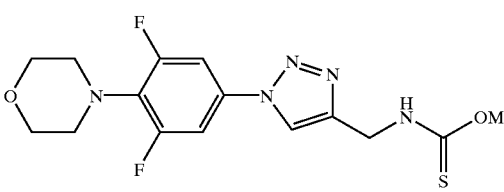
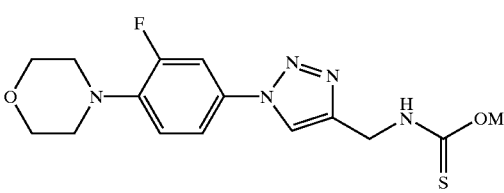
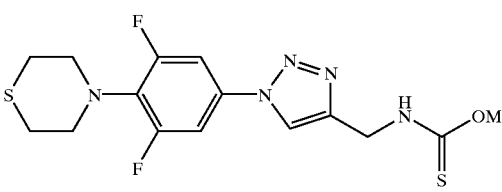
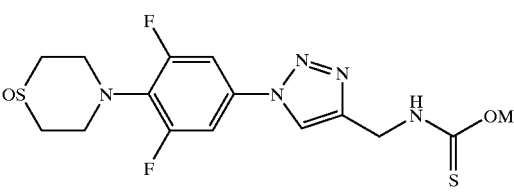
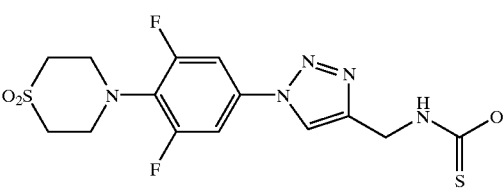
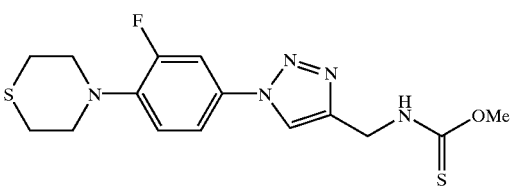

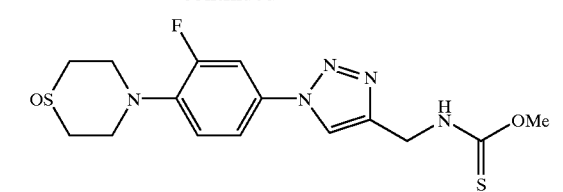
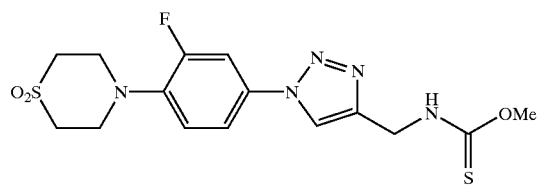
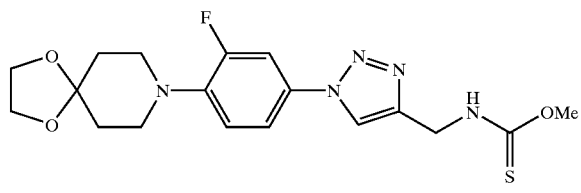
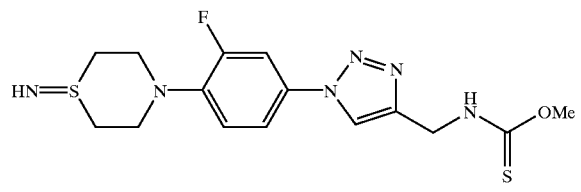
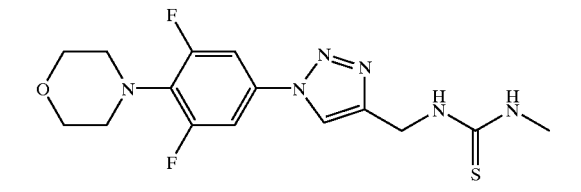
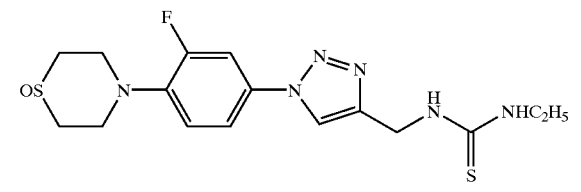
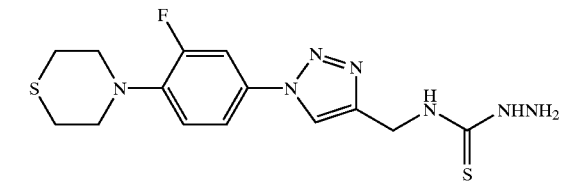
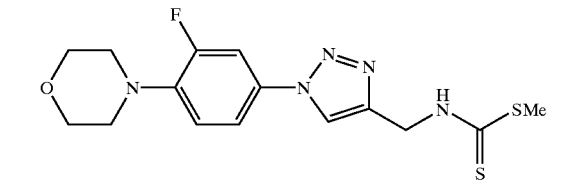
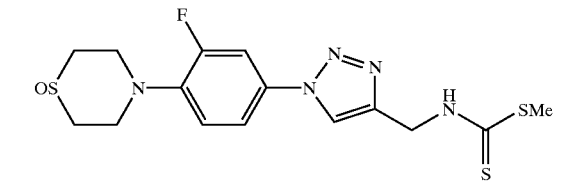
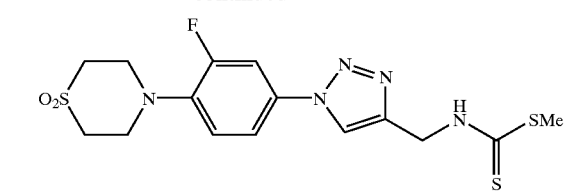
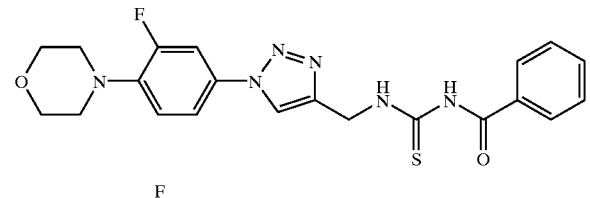
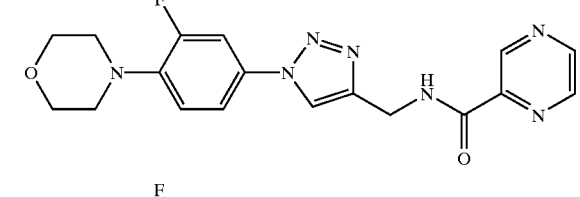
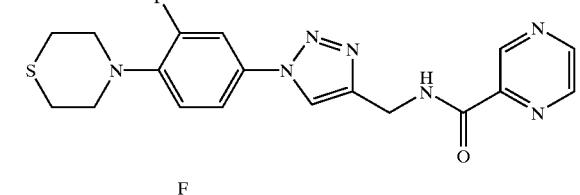
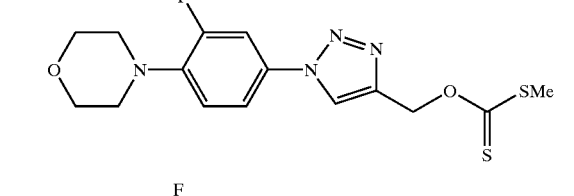
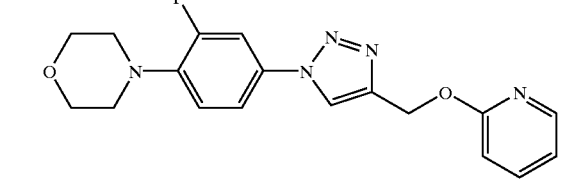
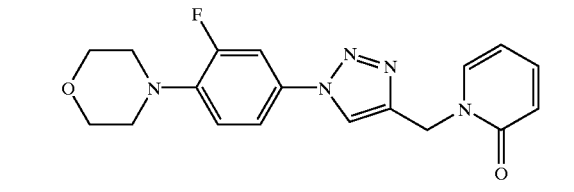
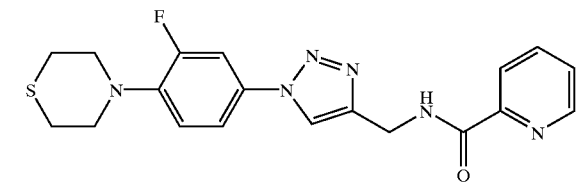
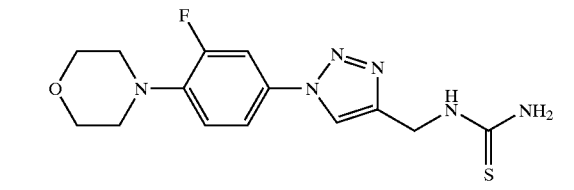

-continued

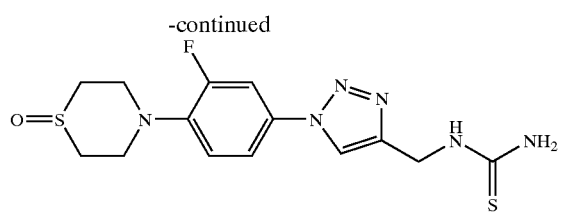

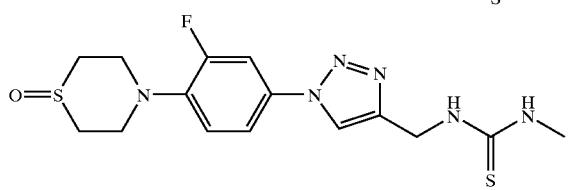

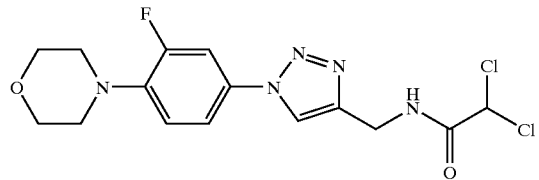

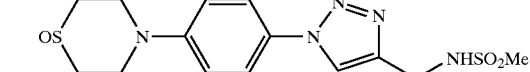

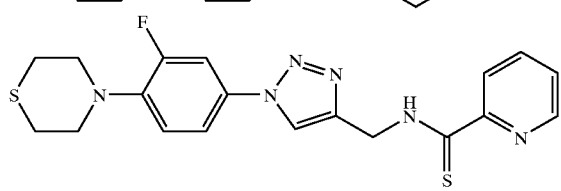

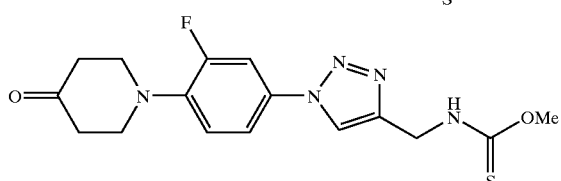

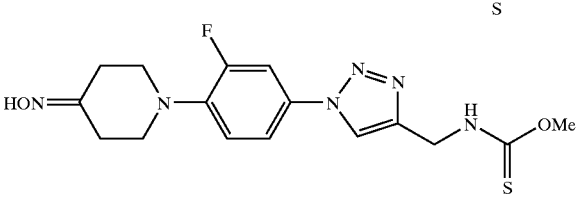

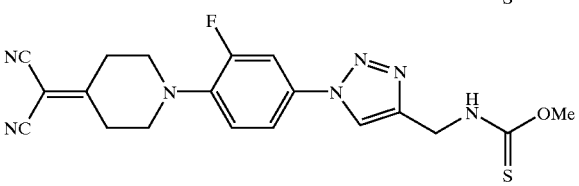

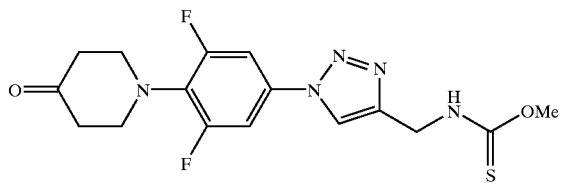

or pharmaceutically acceptable salts thereof.

The present invention also relates to a process for the preparation of the compound of formula (I) where $R^1$ represents azido and all other symbols are as defined earlier, which comprises:

(i) reacting the compound of formula (Ia)

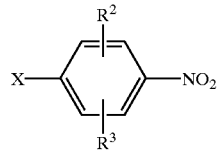

(Ia)

where X represents halogen atom such as fluorine, chlorine, bromine and the like; $R^2$ and $R^3$ are as defined earlier, with a compound of formula (Ib)

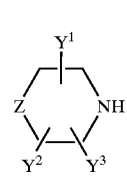

(Ib)

where Z, $Y^1$, $Y^2$ and $Y^3$ are as defined earlier, to produce a compound of formula (Ic)

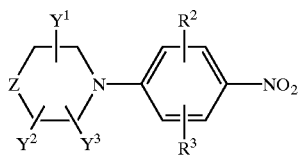

(Ic)

where Z, $Y^1$, $Y^2$, $Y^3$, $R^2$ and $R^3$ are as defined earlier, (ii) reducing the compund of formula (Ic) by using reducing agent to a compound of formula (Id)

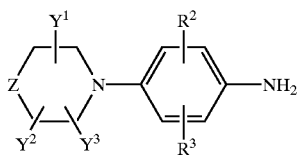

(Id)

where Z, $Y^1$, $Y^2$, $Y^3$, $R^2$ and $R^3$ are as defined earlier (iii) converting the compound of formula (Id) to a compound of formula (Ie)

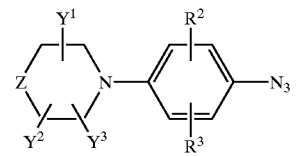

(Ie)

where Z, $Y^1$, $Y^2$, $Y^3$, $R^2$ and $R^3$ are as defined earlier (iv) converting the compound of formula (Ie) to a compound of formula (If)

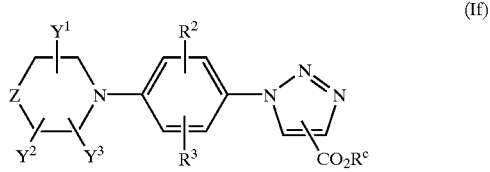

(If)

where $R^c$ represents substituted or unsubstituted ($C_1$–$C_{10}$) alkyl group such as methyl, ethyl, n-propyl, iso-propyl and the like; Z, $Y^1$, $Y^2$, $Y^3$, $R^2$ and $R^3$ are as defined earlier, (v) reducing the compound of fonnula (If), to give a compound of formula (I)

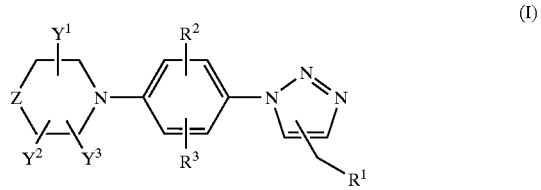

(I)

where $R^1$ represents hydroxy group; Z, $Y^1$, $Y^2$, $Y^3$, $R^2$ and $R^3$ are as defined earlier, (vi) converting the compound of formula (I), where $R^1$ represents hydroxy group, to a compound of formula (I), where $R^1$ represents $OR^5$ wherein $R^5$ represents substituted or unsubstituted $S(O)_2(C_1$–$C_{10})$alkyl or $S(O)_2$aryl group and all other symbols are as defined earlier, and (vii) converting the compound of formula (I) where $R^1$ represents $OR^5$ wherein $R^5$ represents substituted or unsubstituted $S(O)_2(C_1$–$C_{10})$alkyl or $S(O)_2$aryl group, to a compound of formula (I) where $R^1$ represents azido group and all other symbols are as defined earlier. The compound of formula (Ic) may be prepared by reacting a compound of fomula (Ia) with a compound of formula (Ib) by using a base such as KOH, NaOH, $K_2CO_3$, $Na_2CO_3$, NaH, KH, trietliylamine, diisopropylethyl amine and the like. The reaction may be carried out using a solvent such as DMSO, DMF, THF, acetonitrile, chloroform, nitrobenzene and the like or mixtures thereof. The reaction may be carried out in inert atmosphere, which may be maintained using inert gases such as $N_2$ or Ar. The reaction may be carried out at a temperature in the range of 20 to 100° C., preferably at a temperature in the range of ambient-80° C. The reaction time may range from 1 to 15 h, preferably from 6 to 12 h.

The reduction of a compound of formula (Ic) to produce a compound of formula (Id) may be carried out in the presence of reducing agents such as $NiCl_2/NaBH_4$, lithium aluminium hydride (LAH), gaseous hydrogen and a catalyst such as Ru, Pd, Rh, Pt, Ni on solid beads such as charcoal, alumina, asbestos and the like. The reduction may be carried out in the presence of a solvent such as dioxanc, acetic acid, ethyl acetate, THF, alcohol such as methanol, ethanol and the like or mixtures thereof. A pressure between atmospheric pressure to 60 psi may be used. The reaction may be carried out at a temperature from 0 to 60° C., preferably at 0 to room temperature. The reaction time ranges from 0.5 to 48 h, preferably in the range of 0.5 to 5 h. The reduction may also be carried out by employing metal in mineral acids such Sn/HCl, Fe/HCl, Zn/HCl, Zn/$CH_3CO_2H$ and the like.

The compound of formula (Id) may be converted to a compound of formula (Ie) by using $NaNO_2$ in the presence of HCl or $CH_3COOH$ followed by $NaN_3$. The solvent used in the reaction may be selected from methanol, ethanol, ethylacetate, THF, ether, dioxan and the like. The tempera-ture of the reaction may be maintained in the range of –40° C. to boiling temperature, preferably in the range of 0° C. to room temperature. The duration of the reaction may be in the range of 0.5 to 15 h, preferably in the range of 0.5 to 5 h.

The compound of formula (If) may be prepared by heating a compound of formula (Ie) with ($C_1$–$C_6$)alkyl ester of propiolic acid. The solvent used in the reaction may be selected from benzene, toluene, xylene, acetonitrile, THF and the like. The temperature of the reaction may be maintained in the range of 10 to 200° C., preferably in the range of room temperature to the boiling temperature of the solvent. The duration of the reaction may be in the range of 1 to 25 h, preferably 5 to 20 h.

The conversion of compound of formula (If) to a compound of formula (I), where $R^1$ represents hydroxy may be carried out by using reducing agents such as LAH, lithiumborohydride ($LiBH_4$) or $NaBH_4/I_2$. The reaction may be carried out in the presence of a solvent such as methanol, ethanol, THF, $Et_2O$, dioxane and the like, or mixtures thereof. The temperature of the reaction may be in the range of –80 to 100° C., preferably 0° C. to boiling temperature of the solvent. The duration of the reaction may be in the range of 0.5 to 10 h.

The compound of formula (I) where $R^1$ represents OH may be converted to compound of formula (I) where $R^1$ represents $OR^5$ wherein $R^5$ represents substituted or unsubstituted $S(O)_2(C_1$–$C_{10})$alkyl or $S(O)_2$aryl group, by treating with alkylsulfonylchloride or arylsulfonylchloride such as methanesulfonyl chloride, p-toluenesulfonyl chloride and the like. The reaction may be carried out in the presence of chloroform, dichloromethane, THF, dioxane and the like or mixtures thereof The base used in the reaction may be selected from $Et_3N$, diisopropyl ethylamine, $Na_2CO_3$, $K_2CO_3$ and the like. The temperature of the reaction may be maintained in the range of 0 to 50° C., preferably in the range of 0 to room temperature. The duration of the reaction may be in the range of 1 to 12 h, preferably in the range of 1 to 4 h.

The compound of formula (I) where $R^1$ represents $OR^5$ wherein $R^5$ represents substituted or unsubstituted $S(O)_2$ ($C_1$–$C_{10}$)alkyl or $S(O)_2$aryl group may be converted to compound of formula (I) wherein $R^1$ represents azido group, by treating with $NaN_3$. The solvent used in the reaction may be selected from dimethylformamide (DMF), dimethyl sulfoxide (DMSO), methylcyanide, nitromethane and the like. The tempearature of the reaction may be maintained in the range of room temperature to 120° C., preferably room temperature to 80° C. The duration of the reaction may be in the range of 1 to 12 h, preferably 1 to 4 h.

Alternatively, the compound of formula (I) wherein $R^1$ represents hydroxy can be converted to a compound of formula (I) wherein $R^1$ represents azido group without isolating and characterizing the alkylsulfonylor arylsulfonyl intermediate formed.

Another embodiment of the present invention provides an alternative process for the preparation of the compound of formula (I) where $R^1$ represents azido and all other symbols are as defined earlier, which comprises:

(i) converting the compound of formula (Ie)

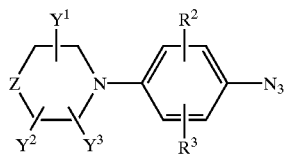

where Z, $Y^1$, $Y^2$, $Y^3$, $R^2$ and $R^3$ are as defined earlier, to a compound of formula (I)

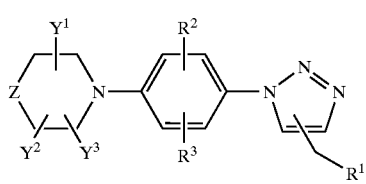

where $R^1$ represents hydroxy; Z, $Y^1$, $Y^2$, $Y^3$, $R^2$ and $R^3$ are as defined earlier and (ii) reacting the compound of formula (I) where $R^1$ represents hydroxy group, with MsCl, triethylamine and sodium azide to a give a compound of formula (I) where $R^1$ represents azido group,

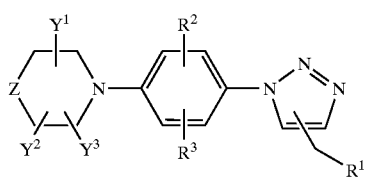

where $R^1$ represents azido; Z, $Y^1$, $Y^2$, $Y^3$, $R^2$ and $R^3$ are as defined earlier.

The compound of formula (Ie) may be converted to a compound of formula (I), where $R^1$ represents hydroxy group, by treating with propargyl alcohol. The solvent used in the reaction may be selected from benzene, toluene, xylene, methylcyanide, THF and the like. The temperature of the reaction may be maintained in the range of 10 to 200° C., preferably room temperature to the boiling temperature of the solvent. The duration of the reaction may be in the range of 1 to 25 h, preferably in the range of 5 to 20 h.

The compound of formula (I) where $R^1$ represents hydroxy group may be converted to a compound of formula (I) where $R^1$ represents azido group was carried out in two steps. In step (1) the compound of formula (I) where $R^1$ represents OH is converted to compound of formula (I) where $R^1$ represents leaving group such as halogen atom, by treating with $CBr_4/PPh_3$, $PBr_3$, $SOCl_2$ and the like. The reaction may be carried out in the presence of chloroform, dichloromethane, THF, dioxane and the like or mixtures thereof. The reaction may be carried out in the presence or absence of a base such as $Et_3N$, diisopropyl ethylamine, $Na_2CO_3$, $K_2CO_3$ and the like. The temperature of the reaction may be maintained in the range of 0 to 80° C., preferably in the range of 0 to 50° C. The duration of the reaction may be in the range of 1-12 h, preferably in the range of 1-4 h. In step (2), the compound of formula (I) where $R^1$ represents halogen atom may be converted to compound of formula (I) where $R^1$ represents azido group by treating with $NaN_3$, $LiN_3$, trialkylsilylazide and the like.

The solvent used in the reaction may be selected from acetone, THF, DMF, dimethyl sulfoxide (DMSO), methylcyanide and the like. The temperature of the reaction may be maintained in the range of room temperature to 120° C., preferably room temperature to 80° C. The duration of the reaction may be in the range of 1 to 12 h, preferably 1 to 4 h.

Yet another embodiment of the present invention provides an alternative process for the preparation of compound of formula (I), where $R^1$ represents azido group, which comprises:

(i) converting the compound of formula (Ie)

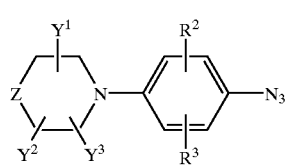

where Z, $Y^1$, $Y^2$, $Y^3$, $R^2$ and $R^3$ are as defined earlier, to a compound of formula (I)

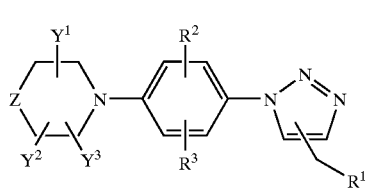

where $R^1$ represents halogen atom such as chlorine, bromine and the like, and all other symbols are as defined earlier and (ii) converting the compound of formula (I) where $R^1$ represents halogen atom such as chlorine, bromine and the like, to a compound of formula (I), wherein $R^1$ represents azido group.

The compound of formula (I), where $R^1$ represents halogen atom such as chlorine, bromine and the like, may be prepared from a compound of formula (Ie) by using propargyl halide such as propargylchloride, propargyl bromide or propargyl iodide. The solvent used in the reaction may be selected from benzene, toluene, xylene, methylcyanide, THF and the like. The temperature of the reaction may be maintained in the range of 10 to 200° C., preferably room temperature to the boiling temperature of the solvent. The duration of the reaction may be in the range of 1 to 25 h, preferably in the range of 5 to 20 h.

The conversion of a compound of formula (I) where $R^1$ represents halogen atom such as chlorine, bromine and the like, to a compound of formula (I) where $R^1$ represents azido group, may be carried out in the presence of one or more equivalents of metal azide such as $LiN_3$, $NaN_3$ or trialkyl silylazide. The reaction may be carried out in the presence of solvent such as THF, acetone, DMF, DMSO and the like or mixtures thereof. The reaction may be carried out in inert atmosphere, which may be maintained using $N_2$ or Ar. The reaction may be carried out at a temperature in the range of ambient temperature to reflux temperature of the solvent, preferably at a temperature in the range of 50 to 80° C. The reaction time may be in the range from 0.5 to 18 h, preferably 1 to 4 h.

Another embodiment of the present invention provides a process for the preparation of compound of formula (I), where $R^1$ represents azido group, Z represents —$S(O)_n$—, where n represents 1 or 2, which comprises:

(i) oxidizing the compound of formula (I),

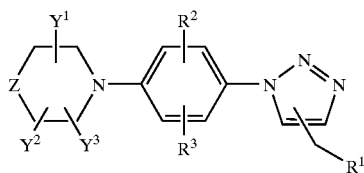
(I)

where R¹ represents azido group; Z represents 'S', to obtain a compound of formula (I) where R¹ represents azido group, Z represents —S(O)$_n$— where n represents 1 or 2; and Y¹, Y², Y³, R² and R³ are as defined earlier.

The conversion of compound of formula (I) where R¹ represents azido group; Z represents 'S', to a compound of formula (I) where R¹ represents azido group, Z represents —S(O)$_n$— where n represents 1 or 2, may be carried out by using oxidizing agents such as m-CPBA, hydrogen peroxide and the like. The solvent used in the reaction may be selected from dichloromethane, chloroform and the like. The temperature of the reaction maybe maintained in the range of −40 to 50° C., preferably in the range of 0° C. to room temperature. The duration of the reaction may be in the range from 0.2 to 10 h, preferably in the range of 0.5 h to 5 h.

Another embodiment of the present invention provides a process for the preparation of compound of formula (I) where R¹ represents NHR⁴ wherein R⁴ represents hydrogen atom, which comprises:

(i) converting the compound of formula (If)

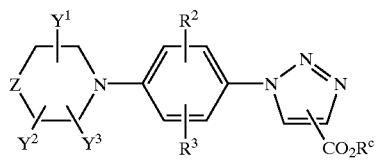
(If)

where R$^c$ represents substituted or unsubstituted ($C_1$–$C_{10}$) alkyl group such as methyl, ethyl, n-propyl, iso-propyl and the like; and all other symbols are as defined earlier, to a compound of formula (Ig)

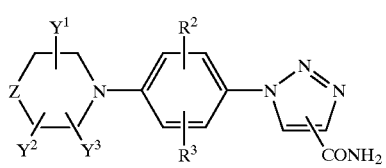
(Ig)

where all symbols are as defined earlier and (ii) reducing the compound of formula (Ig), to produce a compound of formula (I) where R¹ represents NHR⁴ wherein R⁴ represents hydrogen atom and all other symbols are as defined earlier.

The conversion of compound of formula (If) to a compound of formula (Ig) may be carried out in the presence of ammonia solution in water or alcohol. The temperature of the reaction may be in the range of −40 to 50° C., preferably of 0° C. to room temperature. The duration of the reaction may be in the range of 0.5 to 12 h, preferably 0.5 to 4 h.

The reduction of compound of formula (Ig) to a compound of formula (I), where R¹ represents NHR⁴ wherein R⁴ represents hydrogen atom, may be carried out by using borane complex in THF, diethylether, SMe₂ or amine. The solvent used in the reaction may be selected from THF, diethylether, dioxane and the like. The temperature of the reaction may be in the range of −20 to 70° C., preferably 0 to boiling temperature of the solvent. The duration of the reaction may be in the range of 1 to 15 h, preferably 1 to 6 h.

Yet another embodiment of the present invention provides an alternative process for the preparation of compound of formula (I) where R¹ represents NHR⁴ wherein R⁴ represents hydrogen atom, which comprises:

(i) reducing the compound of formula (I) wherein R¹ represents azido group, to produce compound of formula (I)

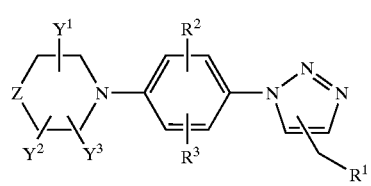
(I)

where R¹ represents NHR⁴ wherein R⁴ represents hydrogen atom; Y¹, Y², Y³, R², R³ and Z are as defined earlier.

The reduction of a compound of formula (I) where R¹ represents azido group, to produce a compound of formula (I) where R¹ represents NHR⁴ wherein R⁴ represents hydrogen atom, may be carried out in the presence of gaseous hydrogen and a catalyst such as Ru, Pd, Rh, Pt, Ni on solid beads such as charcoal, alumina, asbestos and the like. The reduction may be carried out in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature in the range of 25 to 60° C., preferably at room temperature. The duration of the reaction may be in the range of 2 to 48 h. The reduction may also be carried out by employing PPh₃ in water.

Another embodiment of the present invention provides a process for the preparation of compound of formula (I) where R¹ represents hydroxy group, which comprises:

(i) converting the compound of formula (Ie),

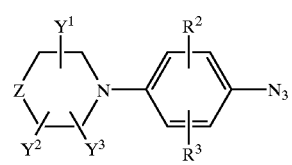
(Ie)

where Z, Y¹, Y², Y³, R² and R³ are as defined earlier, to obtain a compound of formula (I),

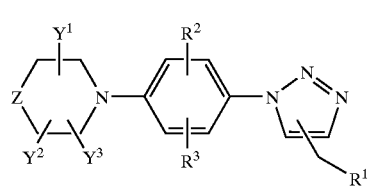
(I)

where R¹ represents OR⁵ wherein R⁵ represents substituted or unsubstituted ($C_1$–$C_{10}$)acyl group, and all other symbols are as defined earlier and (ii) hydrolysis of the compound of formula (I) where $R^1$ represents $OR^5$ wherein $R^5$ is as defined above, to a compound of formula (I), where $R^1$ represents hydroxy group and all other symbols are as defined earlier.

The conversion of compound of formula (Ie) to a compound of formula (I) where $R^1$ represents $OR^5$ wherein $R^5$ is as defined above, may be carried out in the presence of esters (($C_1$–$C_{10}$)alkyl or aryl)of propargyl alcohol. The solvent used in the reaction maybe selected from benzene, toluene, xylene, methylcyanide, tetrahydrofuran (THF) and the like. The temperature of the reaction may be maintained in the range of 10 to 200° C., preferably room temperature to the boiling temperature of the solvent. The duration of the reaction may be in the range of 1 to 25 h, preferably in the range of 5 to 20 h.

The hydrolysis of compound of formula (I) where $R^1$ represents $OR^5$ wherein $R^5$ is as defined above, to a compound of fonnula (I), where $R^1$ represents hydroxy group, may be carried out by using conventional ester hydrolysis procedures.

Yet another embodiment of the present invention provides a process for the preparation of compound of formula (I), where $R^1$ represents $NHR^4$, wherein $R^4$ represents substituted or unsubstituted acetyl group and all other symbols are as defined earlier, from a compound of formula (I) where $R^1$ represents azido group,

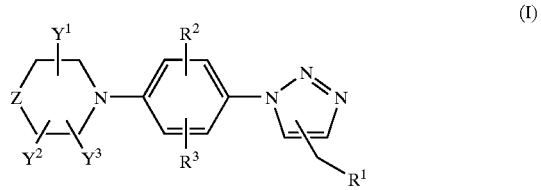
(I)

where $Z$, $Y^1$, $Y^2$, $Y^3$, $R^2$ and $R^3$ are as defined earlier.

The compound of formula (I), where $R^1$ represents $NHR^4$, wherein $R^4$ represents substituted or unsubstituted acetyl group may be prepared from compound of formula (I), where $R^1$ represents azido group may be carried out by using thiolacetic acid with or without using solvent such as THF, dimethylaminopyridine (DMF), toluene and the like. The reaction may be carried out at a temperature in the range of 25 to 40° C., preferably at room temperature. The duration of the reaction may be in the range from 3 to 24 h, preferably from 4 to 12 h.

Still another embodiment of the present invention provides a process for the preparation of compound of formula (I), where $R^1$ represents $NHR^4$, where $R^4$ represents substituted or unsubstituted —C(=S)—$R^{4a}$, wherein $R^{4a}$ represents ($C_1$–$C_{10}$)alkyl, halo($C_1$–$C_{10}$)alkyl, aryl, heteroaryl, —C(=O)—($C_1$–$C_{10}$)alkoxy, —C(=O)—($C_1$–$C_{10}$)alkoxy, —C(=O)-aryloxy, —C(=S)—($C_1$–$C_{10}$)alkyl or —C(=S)-aryl; from compound of formula (I), where $R^1$ represents $NHR^4$, where $R^4$ represents substituted or unsubstituted —C(=O)—$R^{4a}$, wherein $R^{4a}$ represents ($C_1$–$C_{10}$)alkyl, halo($C_1$–$C_{10}$)atkyl, aryl, heteroaryl, —C(=O)—($C_1$–$C_{10}$) alkoxy, —C(=O)-aryloxy, —C(=S)—($C_1$–$C_{10}$)alkyl or —C(=S)-aryl

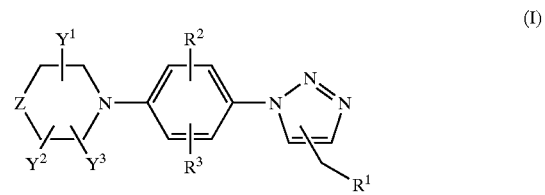
(I)

where all symbols are as defined earlier.

The compound of formula (I), where $R^1$ represents $NHR^4$, wherein $R^4$ represents substituted or unsubstituted —(=S)—$R^{4a}$, from compound of formula (I), where $R^1$ represents $NHR^4$, wherein $R^4$ represents substituted or unsubstituted —C(=O)—$R^{4a}$, wherein $R^{4a}$ is as defined above, may be carried out by taking a solution of the amide and Lawesson's reagent (2,4-bis(methoxyphenyl)-1,3-dithia-2,4-diphosphetane-2,4-disulfide) in dry dioxane, toluene, THF, DMF and the like. The reaction may be carried out at a temperature in the range of room temperature to 130° C., preferably in the range of 55 to 90° C. The duration of the reaction may be in the range from 3 to 24 h, preferably from 3 to 10 h.

Another embodiment of the present invention provides a process for the preparation of compound of formula (I), where $R^1$ represents $NHR^4$, wherein $R^4$ represents substituted or unsubstituted —C(=S)—$OR^{4b}$, wherein $R^{4b}$ represents ($C_1$–$C_{10}$)alkyl, cyclo($C_3$–$C_{10}$)alkyl, aryl, ($C_2$–$C_{10}$) alkenyl or —C(=O)—($C_1$–$C_{10}$)alkyl group, which comprises:

(i) reacting compound of formula (I)

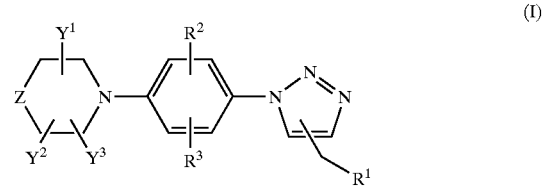
(I)

where $R^1$ represents azido group; and all other symbols are as defined earlier, with triphenylphosphine/water or $H_2$—Pd/C, to produce a compound of formula (I), where $R^1$ represents $NHR^4$, wherein $R^4$ represents hydrogen atom and all other symbols are as defined earlier, (ii) reacting compound of formula (I), where $R^1$ represents $NHR^4$, wherein $R^4$ represents hydrogen atom, with thiophosgene or carbon disulfide and chloromethylformate, in the presence of a base to produce a compound of formula (I)

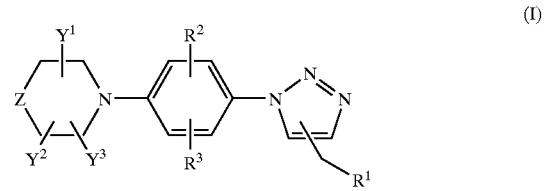
(I)

where $R^1$ represents isothiocyanate group; and all symbols are as defined earlier, (iii) converting compound of formula (I) where $R^1$ represents isothiocynate group, to a compound of formula (I), where $R^1$ represents $NHR^4$, wherein $R^4$ represents substituted or unsubstituted —C(=S)—$OR^{4b}$, wherein $R^{4b}$ is as defined above and all other symbols are as defined earlier.

The conversion of compound of formula (I), where $R^1$ represents azido to a compound of formula (I), where $R^1$ represents $NHR^4$, wherein $R^4$ represents hydrogen atom may be carried out in the presence of gaseous hydrogen and a catalyst such as Ru, Pd, Rh, Pt, Ni on solid beads such as charcoal, alumina, asbestos and the like. The reduction may be conducted in the presence of a solvent such as dioxane, acetic acid, ethyl acetate, tetrahydrofuran (THF), alcohol such as methanol, ethanol, propanol, isopropanot and the like or mixtures thereof. A pressure between atmospheric pressure to 60 psi may be used. The reaction may be carried out at a temperature in the range of 25 to 60° C., preferably in the range of room temperature to 80° C. The duration of the reaction may be in the range of 2 to 48 h, preferably in the range of 5 to 15 h. The reduction may also be carried out by employing $PPh_3$ and water.

The compound of formula (I), where $R^1$ represents $NHR^4$, wherein $R^4$ represents hydrogen atom may be converted to a compound of formula (I) where $R^1$ represents isothiocyanate group, by using thiophosgene or carbon disulfide and chloromctlhylformate in the presence of a base such as $Et_3N$, $K_2CO_3$, NaOH and the like. The reaction may be carried out in the presence of a solvent such as $CH_2Cl_2$, $CH_3CN$, $CHCl_3$, DMF, THF and the like. The reaction may be carried at a temperature in the range of 0 to 60° C., preferably at 0° C. The reaction may be carried out in an inert atmosphere using argon or any other inert gas. The duration of the reaction may be in the range of 1 to 24 h, preferably 2 to 10 h.

The conversion of compound of formula (I) where $R^1$ represents isothiocyanate group, to a compound of formula (I), where $R^1$ represents $NHR^4$, wherein $R^4$ represents substituted or unsubstituted —C(=S)—$OR^{4b}$, wherein $R^{4b}$ is as defined above, may be carried out by using respective alcohol such as methanol, ethanol, propanol, cyclohexanol and the like, in the absence or presence of a base such as NaH, KH and the like. The reaction may be carried out in the presence of a solvent such as THF, toluene, DMF and the like. The reaction may be carried out at a temperature in the range of room temperature to 130° C., preferably at reflux temperature of the solvent used. The duration of the reaction may be in the range of 6 to 24 h.

Another embodiment of the present invention provides a process for the preparation of compound of formula (I), where $R^1$ represents $NHR^4$, where $R^4$ represents substituted or unsubstituted groups selected from —C(=S)—$NH_2$, —C(=S)—NH—($C_1$-$C_{10}$)alkyl, —C(=S)—N—(($C_1$-$C_{10}$)alkyl)$_2$, —C(=S)—NH—($C_2$-$C_{10}$)alkenyl, C(=S)—NH—C(=O)-aryl, —C(=S)—NH-aralkyl, —C(=S)—NH-heteroaralkyl or —C(=S)—N(R'R"), wherein R' and R" groups together form a substituted or unsubstituted 5 or 6 membered cyclic structures containing nitrogen and optionally one or two additional hetero atoms selected from oxygen, nitrogen or sulfur; from a compound of formula (I) where $R^1$ represents isothiocyanate group,

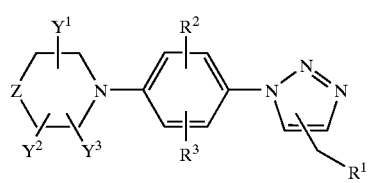

(I)

where all symbols are as defined earlier.

The compound of formula (I), whcre $R^1$ represents $NHR^4$, wherein $R^4$ represents substituted or unsubstituted —C(=S)—$NH_2$, may be prepared by passing ammonia gas into a solution of compound of formula (I) where $R^1$ represents isothiocyanate group, in the presence of a solvent such as THF, toluene, and the like. The reaction may be carried out at a temperature in the range of –10° C. to room temperature, preferably at –10° C. The duration of the reaction may be in the range from 20 min to 4 h, preferably 30 min.

The compound of formula (I), where $R^1$ represents $NHR^4$, wherein $R^4$ represents substituted or unsubstituted groups selected from —C(=S)—NH—($C_1$-$C_{10}$)alkyl, —C(=S)—N—(($C_1$-$C_{10}$)alkyl)$_2$, —C(=S)—NH—($C_2$-$C_{10}$)alkenyl, C(=S)—NH—C(=O)-aryl, —C(=S)—NH-aralkyl, —C(=S)—NH-heteroaralkyl or —C(=S)—N(R'R"), wherein R' and R" groups together form a substituted or unsubstituted 5 or 6 membered cyclic structures containing nitrogen and optionally one or two additional hetero atoms selected from oxygen, nitrogen or sulfur, may be carried out by treating a compound of formula (I) where $R^1$ represents isothiocyanate group with appropriate amine such as methylamine, ethylamine, diemthylamine, diethylamine, benzylamine, aniline, proline, morplioline, thiomorpholine, pyridiylmethylamine and the like, in the presence of a solvent such as THF, DMF, toluene, and the like. The reaction may be carried out at a temperature in the range of room temperature to 140° C., preferably at room temperature to 100° C. The duration of the reaction may be in the range of 0.5 to 24 h, preferably 0.5 to 12 h.

Yet another embodiment of the present invention provides a process for the preparation of compound of formula (I), where $R^1$ represents $NHR^4$, wherein $R^4$ represents substituted or unsubstituted —C(=S)—$SR^{4c}$, wherein $R^{4c}$ represents ($C_1$-$C_{10}$)alkyl group, from compound of formula (I), where $R^1$ represents $NHR^4$, wherein $R^4$ represents hydrogen atom,

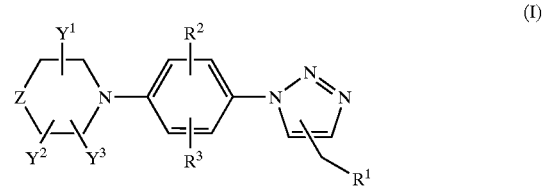

(I)

where all other symbols are as defined earlier.

The compound of formula (I), where $R^1$ represents $NHR^4$, wherein $R^4$ represents substituted or unsubstituted —C(=S)—$SR^{4c}$, wherein $R^{4c}$ is as defined above, may be prepared from compound of formula (I), where $R^1$ represents $NHR^4$, wherein $R^4$ represents hydrogen atom, by using $CS_2$ in the presence of a base such as $Et_3N$, diisopropyl ethylamine, $K_2CO_3$, NaH, t-BuOK and the like. The reaction nay be carried out in the presence of alkyl halide such as methyliodide, ethylbromide, propylbromide and the like. The solvent used in the reaction may be selected from ethanol, methanol, isopropanol, THF, diethylether, acetonitrile and the like, or mixtures thereof. The reaction may be carried out at a temperature in the range of room temperature to 60° C., preferably at room temperature. The duration of the reaction may be in the range of 6 to 24 h.

Another embodiment of the present invention provides a process for the preparation of compound of formula (I), where $R^1$ represents $NHR^4$, wherein $R^4$ represents substituted or unsubstituted —C(=S)—NH—$R^{4d}$, wherein $R^{4d}$ represents —C(=O)-aryl group, from compound of formula (I), where $R^1$ represents $NHR^4$, wherein $R^4$ represents hydrogen atom,

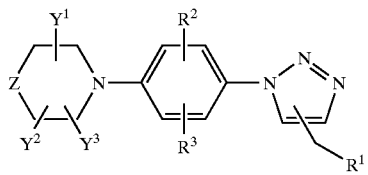

where all other symbols are as defined earlier.

The compound of formula (I), where $R^1$ represents $NHR^4$, wherein $R^4$ represents substituted or unsubstituted —C(=S)—NH—$R^{4d}$ wherein $R^{4d}$ is as defined above, may be prepared from compound of formula (I), where where $R^1$ represents $NHR^4$ wherein $R^4$ represents hydrogen atom by using benzoylisothiocyanate. The solvent used in the reaction may be selected from acetone, ethanol, methanol, isopropanol, THF, diethylether, methylcyanide and the like. The temperature of the reaction may be maintained in the range of 0 to 80° C., preferably in the range of room temperature to 60° C. The duration of the reaction may be in the range of 1 to 20 h, preferably in the range of 1 to 10 h.

Yet another embodiment of the present invention provides a process for the preparation of compound of formula (I), where $R^1$ represents $NHR^4$, wherein $R^4$ represents substituted or unsubstituted —C(=O)-heteroaryl, from a compound of formula (I), where $R^1$ represents $NHR^4$, wherein $R^4$ represents hydrogen atom,

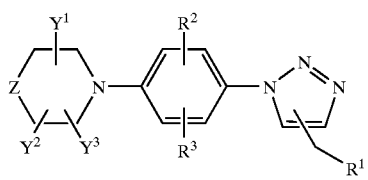

where all other symbols are as defined earlier.

The compound of fomula (I), where $R^1$ represents $NHR^4$, wherein $R^4$ represents substituted or unsubstituted —C(=O)-heteroaryl, may be prepared from compound of formula (I), where $R^1$ represents $NHR^4$, wherein $R^4$ represents hydrogen atom by treating with corresponding heteroaroyl acid chloride and base such such as pyridine, triethylamine or diisopropylamine. The reaction may also be carried out by using corresponding heteroaryl acid and dicyclohexylcarbodiimide (DCC) in the presence of dimethylaminopyridine (DMAP). The solvent used in the reaction may be selected from acetonitrile, THF, methylcyanide, $Et_2O$ and the like. The temperature of the reaction may be maintained in the range of −5 to 100° C., preferably in the range of 0 to 80° C. The duration of the reaction may be in the range of 1 to 15 h, preferably in the range of 2 to 12 h.

Another embodiment of the present invention provides a process for the preparation of compound of formula (I), where $R^1$ represents $OR^5$, wherein $R^5$ represents substituted or unsubstituted group selected from heteroaryl or $R^1$ represents $N(R^6)_2$, wherein —$(R^6)_2$ together represent a substituted or unsubstituted 5 or 6 membered heterocycle containing nitrogen and optionally having one or two additional hetero atoms selected from nitrogen, oxygen or sulfur, from a compound of formula (I), where $R^1$ represents $OR^5$, wherein $R^5$ represents substituted or unsubstituted group selected from $S(O)_2(C_1-C_{10})$alkyl or $S(O)_2$aryl group,

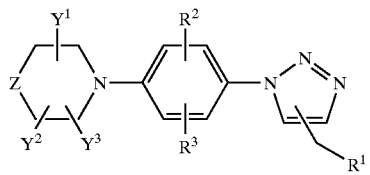

where all other symbols are as defined earlier.

The compound of fomula (I), where $R^1$ represents $OR^5$, wherein $R^5$ represents heteroaryl or $R^1$ represents $N(R^6)_2$, wherein —$(R^6)_2$ together represent a substituted or unsubstituted 5 or 6 heterocycle containing nitrogen and optionally having one or two additional hetero atoms, may be prepared from compound of formula (I), where $R^1$ represents represents $OR^5$, wherein $R^5$ represents a substituted or unsubstituted $S(O)_2(C_1-C_{10})$alkyl or $S(O)_2$aryl group, by using 2-pyridinol. The solvent used in the reaction may be selected from DMF, THF, diethylether, methyl cyanide and the like. The base used in the reaction may be selected from NaH, $K_2CO_3$, t-BuOK and the like. The temperature of the reaction may be in the range of 0 to 150° C., preferably in the range of room temperature to 90° C. The duration of the reaction may be in the range of 0.5 to 10 h, preferably in the range of 1 to 6 h.

Still another embodiment of the present invention provides a process for the preparation of compound of formula (I), where $R^1$ represents $NHR^4$ where $R^4$ represents substituted or unsubstituted —C(=O)—$R^{4c}$, wherein $R^{4c}$ represents $(C_1-C_{10})$alkyl, $(C_1-C_{10})$alkoxy, $(C_2-C_{10})$alkenyl, halo$(C_1-C_{10})$alkyl, aryl, aryloxy, lieteroaryl, $(C_2-C_{10})$alkenyloxy, $(C_1-C_{10})$alkylcarbonyl, arylcarbonyl, aryloxycarbonyl, $(C_1-C_{10})$alkoxycarbonyl, $(C_1-C_{10})$alkylthiocarbonyl or $(C_1-C_{10})$arylthiocarbonyl; from a compound of formula (I), where $R^1$ represents $NHR^4$, wherein $R^4$ represents hydrogen atom,

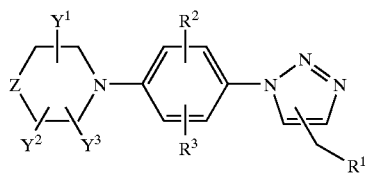

where all other symbols are as defined earlier.

The compound of formula (I), where $R^1$ represents $NHR^4$, wherein $R^4$ represents substituted or unsubstituted —C(=O)—$R^{4e}$, wherein $R^{4e}$ is as defined above, may be prepared from compound of formula (I), where R represents $NHR^4$, wherein $R^4$ represents hydrogen atom, by treating with appropriate acid halide such as acetyl chloride, propionyl chloride and the like; alkylchloroformate like methylchloroformate, cthylchlorofonnate and the like; aralkylchloroformate like benzylchloroformate and the like; or anhydride of the corresponding acid such as acetic anhydride. The reaction may be carried out in the presence of a solvent such as $CH_2Cl_2$, $CHCl_3$, toluene, THF and the like or mixtures thereof. The reaction may also be carried out in the presence of a base like $Et_3N$, diisopropyl ethylamine, pyridine, $K_2CO_3$, NaH, t-BuOK and the like. The temperature of the reaction may be maintained in the range of −20 to 60° C., preferably in the range of 0 to room temperature. The duration of the reaction may be in the range of 1 to 12 h, preferably from 1 to 4 h.

Another embodiment of the present invention provides a process for the preparation of compound of formula (I), where $R^1$ represents $OR^5$, wherein $R^5$ represents substituted or unsubstituted group selected from —C(=S)—S—$(C_1-C_{10})$alkyl group, from a compound of formula (I), where $R^1$ represents $OR^5$, wherein $R^5$ represents hydrogen atom,

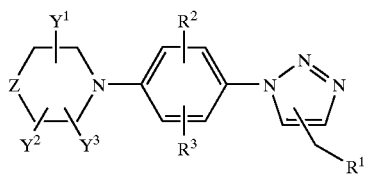

(I)

where all other symbols are as defined earlier.

The compound of formula (I), where $R^1$ represents $OR^4$, wherein $R^4$ represents substituted or unsubstituted group selected from —C(=S)—S—$(C_1-C_{10})$alkyl group, may be prepared from compound of formula (I), where $R^1$ represents $OR^5$, wherein $R^5$ represents hydrogen atom by treating with a base such as pyridine, $Et_3N$, $K_2CO_3$, NaOMe, t-BuOK, NaH and the like. The solvent used in the reaction may be selected from THF, acetonitrile, DMF and the like. The reaction may be carried out in the presence of reagents $CS_2$ and alkyl halide. The temperature of the reaction may be maintained in the range of –20 to 80° C., preferably in the range of 0 to room temperature. The duration of the reaction may be in the range of 0.5 to 10 h, preferably in the range of 1 to 5 h.

Yet another embodiment of the present invention provides a process for the preparation of compound of formula (I) where $R^1$ represents $NHR^4$ where $R^4$ represents substituted or unsubstituted —C(=NH)—$NH_2$, by reacting a compound of formula (I), where $R^1$ represents $NHR^4$ wherein $R^4$ represents hydrogen atom, with di-tert-butoxy carbonyl thiourea,

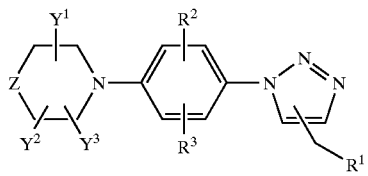

(I)

where all other symbols are as defined earlier.

The compound of formula (I) where $R^1$ represents $NHR^4$ where $R^4$ represents substituted or unsubstituted group selected from —C(=NH)—$NH_2$, may be prepared by reacting the compound of formula (I), where $R^1$ represents $NHR^4$ where $R^4$ represents hydrogen atom, with di-tert-butoxy carbonyl thiourea in two steps. In the first step, the reaction may be carried out in the presence of solvents such as DMF, acetone, THF, dichloromethane and the like. The base used in the reaction may be selected from triethylamine, diisopropylethylamine, pyridine and the like. The temperature of the reaction may be in the range of 0 to 120° C., preferably in the range of 0 to 90° C. The duration of the reaction may be in the range of 0.2 to 15 h, preferably in the range of 0.5 to 10 h. In the second step, the compound obtained in the first step may be reacted with trifluoroacetic acid in the presence of a solvent such as dichloromethane, chloroform, THF and the like. The temperature of the reaction may be in the range of 0 to 110° C., preferably in the range of 0 to 90° C. The duration of the reaction may be in the range of 0.5 to 60 h, preferably in the range of 0.5 to 54 h.

Another embodiment of the present invention provides an alternative process for the preparation of compound of formula (I) where $R^1$ represents $NHR^4$ where $R^4$ represents—substituted or unsubstituted group selected from —C(=NH)—$NH_2$, by reacting a compound of formula (I), where $R^1$ represents $NHR^4$ wherein $R^4$ represents substituted or unsubstituted group selected from —$S(O)_2$$(C_1-C_{10})$alkyl or —$S(O)_2$aryl group, with guanidine hydrochloride,

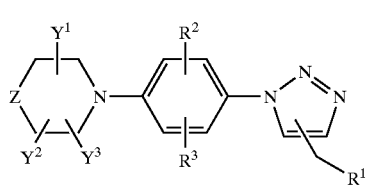

(I)

where all other symbols are as defined earlier.

The compound of formula (I) where $R^1$ represents $NHR^4$ where $R^4$ represents substituted or unsubstituted group selected from —C(=NH)—$NH_2$, may be prepared by reacting the compound of formula (I), where $R^1$ represents $NHR^4$ wherein $R^4$ represents substituted or unsubstituted group selected from —$S(O)_2(C_1-C_{10})$alkyl or —$S(O)_2$aryl group, with guanidine hydrochloride. The solvent used in the reaction may he seleceted form t-butyl alcohol. The base used in the reaction may be selected from NaH, KH, sodium hexamethyldisilazide (Na-HMDS) and the like. The temperature of the reaction may be in the range of 0° C. to boiling temperature of the solvent used. The duration of the reaction may be in the range of 1 to 30 h, preferably in the range of 1 to 24 h.

Still another embodiment of the present invention provides a process for the preparation of compound of formula (I) where $R^1$ represents $NHR^4$ where $R^4$ represents substituted or unsubstituted group selected from —C(=NH)—$(C_1-C_{10})$alkyl or —C(=NH)-aryl, which comprises:

(i) reacting the compound of formula (I)

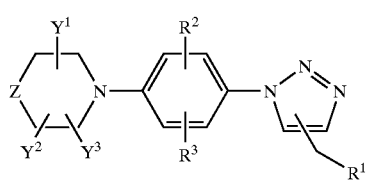

(I)

where $R^1$ reprsents $NHR^4$, wherein $R^4$ represents —C(S)—$NH_2$ and all other symbols are as defined earlier, with di tert-butoxy carbonyl ether (($BOC)_2O$), to produce a compound of formula (I)

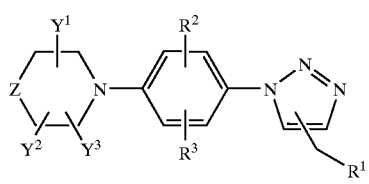

(I)

where $R^1$ represents $NHR^4$, wherein $R^4$ represents —C(=S)—$NH_2$ group substituted with tert-butoxy carbonyl group and all symbols are as defined earlier and (ii) reacting the above compound of formula (I), with a compound of formula (Ii)

$$R^7—NH_2 \quad (Ii)$$

where $R^7$ represents substituted or unsubstituted ($C_1$-$C_{10}$) alkyl or aryl group, to produce a compound of formula (I) where $R^1$ represents $NHR^4$ where $R^4$ represents substituted or unsubstituted group selected from —C(=NH)—($C_1$-$C_{10}$)alkyl or —C(=NH)-aryl group and all other symbols are as defined earlier.

The conversion of the compound of formula (I) where $R^1$ represents $NHR^4$, wherein $R^4$ represents —C(=S)—$NH_2$, to a compound of formula (I), where $R^1$ represents $NHR^4$, wherein $R^4$ represents —C(=S)—$NH_2$ group substituted with tert-butoxy carbonyl group may be carried out by reacting with $(BOC)_2O$, in the presence of solvent such as tHF, diethylether and the like. The base used in the reaction may be selected from NaH, KH, Na-HMDS and the like. The temperature of the reaction may be in the range of 0 to boiling temperature of the solvent. The duration of the reaction may be in the range of 0.5 to 14 h, preferably in the range of 0.5 to 10 h.

The conversion of the compound of formula (I), where $R^1$ represents $NHR^4$, wherein $R^4$ represents —C(=S)—$NH_2$ group substituted with tert-butoxy carbonyl group, to a compound of formula (I) may be carried out by reacting with the compound of formula (Ii) in two steps. In the first step, the reaction may be carried out in the presence of a solvent such as DMF, THF, chloroform, dichloromethane and the like. The base used in the reaction may be selected from triethylamine, diisopropylethylamine, pyridine and the like. The temperature of the reaction may be in the range of 0 to 120° C., preferably in the range of 0 to 90° C. The duration of the reaction may be in the range of 0.5 to 24 h, preferably in the range of 0.5 to 20 h. In the second step, the compound obtained in the first step may be reacted with trifluoroacetic acid in the presence of a solvent such as dichloromethane, chloroform, THF and the like. The temperature of the reaction may be in the range of 0 to 10° C., preferably in the range of 0 to 90° C. The duration of the reaction may be in the range of 0.5 to 60 h, preferably in the range of 0.5 to 54 h.

Another embodiment of the present invention provides a process for the preparation of compound of formula (I), Z represents —$S(O)_n$—, where n represents 1 or 2, which comprises:

(i) oxidizing the compound of formula (I),

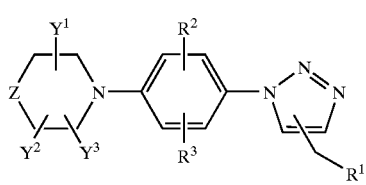

(I)

where Z represents 'S', to obtain a compound of formula (I) where Z represents —$S(O)_n$—, where n represents 1 or 2; and $Y^1$, $Y^2$, $Y^3$, $R^1$, $R^2$ and $R^3$ are as defined earlier.

The conversion of compound of formula (I) where Z represents 'S', to a compound of formula (I) where Z represents —$S(O)_n$— where n represents 1 or 2, by using m-chloroperoxybenzoic acid (m-CPBA), hydrogen peroxide and the like. The solvent used in the reaction may be selected from $CH_2Cl_2$, $CHCl_3$, THF and the like. The temperature of the reaction may be maintained in the range of −5 to 60° C., preferably in the range of 0° C. to room temperature. The duration of the reaction may be in the range of 0.2 to 8 h, preferably in the range of 0.5 to 5 h.

Yet another embodiment of the present invention provides a process for the preparation of a compound of formula (I) where $R^1$ represents halogen, from compound of formula (I) where $R^1$ represents hydroxy group,

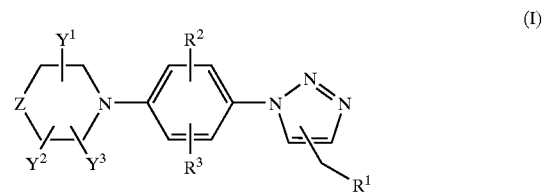

(I)

where all other symbols are as defined above.

The compound of formula (I) where $R^1$ represents halogen is prepared from compound of formula (I) where $R^1$ represents hydroxy group may be carried out by treating with $SOCl_2$, $PCl_5$, $PBr_3$, tetrahalomethane group such as $CBr_4$, $CCl_4$ and the like, in the presence of $PPh_3$, $P(alkyl)_3$ and the like. The reaction may be carried out in the presence of a solvent such as dry dichloromethane, chloroform, tetrachloromethane, benzene, dimethyl formamide (DMF), dimethylsulfoxide (DMSO), THF and the like. The temperature of the reaction may be maintained in the range of 0 to 60° C., preferably at room temperature. The duration of the reaction may be in the range of 0.5 to 24 h, preferably 1 to 13 h.

Still another embodiment of the present invention provides a process for the preparation of a compound of formula (I) where $R^1$ represents 'SH',

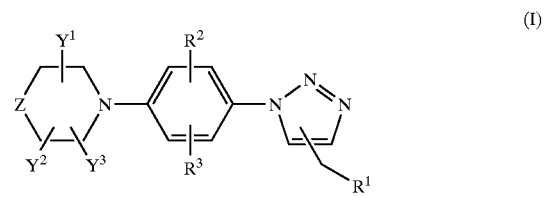

(I)

where all other symbols are as defined above, which comprises:

(i) reacting the compound of formula (I) where $R^1$ represents halogen atom, to produce a compound of formula (Ih),

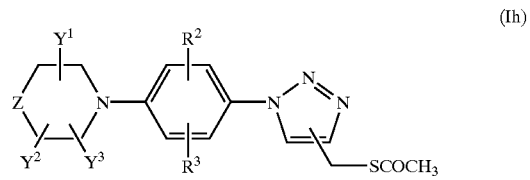

(Ih)

where all other symbols are as defined earlier, with a base and thiolacetic acid, (ii) reacting the compound of formula (Ih), to produce a compound of formula (I) where $R^1$ represents 'SH' group and all other symbols are as defined earlier, with base.

The compound of formula (Ih) is prepared from compound of formula (I) where $R^1$ represents halogen atom may be prepared by using thiolacetic acid in the presence of a base such as triethylamine, di-isopropylamine, di-isopropylethylamine, pyridine, piperidine, DMAP, 1,8- diazabicyclo[5.4.0]undec-7-ene (DBU), lithium diisopropylamide (LDA), potassium bis-(trimethyl silyl)amide, BuLi, $Na_2CO_3$, $K_2CO_3$, NaOH, KOH, NaOMe, NaOEt, NaOiPr, t-BuOK, NaH, KH and the like. The solvent used in the reaction may be seleceted from THF, benzene, dioxane and the like. The temperature of the reaction may be maintained in the range of room temperature to reflux temperature, preferably at reflux temperature. The duration of the reaction may be in the range of 2 to 24 h, preferably 6 h.

The compound of formula (I), where $R^1$ represents 'SH' group may be prepared from a compound of formula (Ih) by reacting with a base such as $K_2CO_3$, NaOH, KOH, BuLi and the like. The reaction may be carried out at a temperature in the range of room temperature to reflux temprature. The duration of the reaction may be in the range of 1 to 24 h.

Still yet another embodiment of the present invention provides a process for the preparation of compound of formula (I), where $R^1$ represent $NHR^4$ wherein $R^4$ represents substituted or unsubstituted —$S(O)_2(C_1-C_{10})$alkyl or —$S(O)_2$aryl group, from a compound of formula (I) where $R^1$ represents $NHR^4$ where $R^4$ represents hydrogen atom, (i) reacting the compound of formula (I),

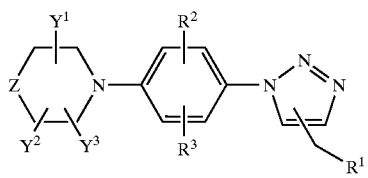

(I)

where $R^1$ represents $NHR^4$ where $R^4$ represents hydrogen atom and all other symbols are as defined in the description, to a compound of formula (I), where $R^1$ represents $NHR^4$, wherein $R^4$ represents substituted or unsubstituted group selected from —$S(O)_2$—$(C_1-C_{10})$alkyl or —$S(O)_2$-aryl group and all other symbols are as defined in the description, to a compound of formula (I).

The conversion of compound of formula (I), where $R^1$ represents $NHR^4$ where $R^4$ represents hydrogen atom, to a compound of formula (I), where $R^1$ represents $NHR^4$, wherein $R^4$ represents substituted or unsubstituted group selected from —$S(O)_2$—$(C_1-C_{10})$alkyl or —$S(O)_2$-aryl group, may be carried out by treating with alkylsulfonylchloride or arylsulfonylchloride such as methanesulfonyl chloride, p-toluenesulfonyl chloride and the like. The solvent used may be selected from dichloromethane, tetrahydrofuran, acetonitrile, dimethylformamide, dimethylsulfoxide and the like. The temperature of the reaction may be in the range of 0 to 50° C., for a duration of 1 to 6 h.

Another embodiment of the present invention provides a novel intermediate of the formula (Ie),

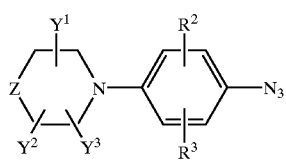

(Ie)

where Z, $Y^1$, $Y^2$, $Y^3$, $R^2$ and $R^3$ are as defined earlier.

Yet another embodiment of the present invention provides a process for the preparation of novel intermediate of formula (Ie), which comprises:

(i) reacting the compound of formula (Ia),

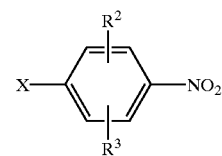

(Ia)

where X represents halogen atom such as fluorine, chlorine, bromine and the like; $R^2$ and $R^3$ are as defined earlier, with a compound of formula (Ib)

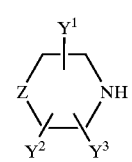

(Ib)

where Z, $Y^1$, $Y^2$ and $Y^3$ are as defined earlier, to produce a compound of formula (Ic)

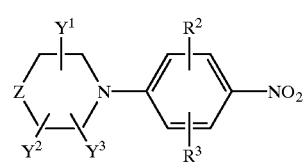

(Ic)

where Z, $Y^1$, $Y^2$, $Y^3$, $R^2$ and $R^3$ are as defined earlier, (ii) reducing the compound of formula (Ic), by using reducing agent to a compound of

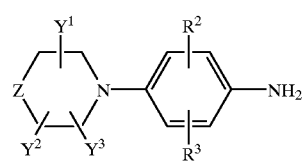

(Id)

where Z, $Y^1$, $Y^2$, $Y^3$, $R^2$ and $R^3$ are as defined earlier, and (iii) converting the compound of formula (Id), to a compound of formula (Ie)

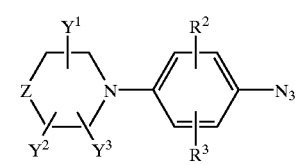

(Ie)

where Z, $Y^1$, $Y^2$, $Y^3$, $R^2$ and $R^3$ are as defined earlier.

The compound of formula (Ic) may be prepared by reacting a compound of formula (Ia) with a compound of formula (Ib) by using a base such as KOH, NaOH, $K_2CO_3$, $Na_2CO_3$, NaH, KH, triethylamine, diisopropylethyl amine and the like. The reaction may be carried out using a solvent such as DMSO, DMF, THF, acetonitrile, chloroform, nitrobenzene and the like or mixtures thereof. The reaction may be carried out in inert atmosphere, which may be maintained using inert gases such as $N_2$ or Ar. The reaction may be carried out at a temperature in the range of 20 to 100°

C., preferably at a temperature in the range of ambient −80° C. The reaction time may range from 1 to 15 h, preferably from 6 to 12 h.

The reduction of a compound of formula (Ic) to produce a compound of formula (Id) may be carried out in the presence of reducing agents such as $NiCl_2/NaBH_4$, lithium aluminium hydride (LAH), gaseous hydrogen and a catalyst such as Ru, Pd, Rh, Pt, Ni on solid beads such as charcoal, alumina, asbestos and the like. The reduction may be carried out in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature from 0 to 60° C., preferably at 0 to room temperature. The reaction time ranges from 0.5 to 48 h, preferably in the range of 0.5 to 5 h. The reduction may also be carried out by employing metal in mineral acids such $Sn/HCl$, $Fe/HCl$, $Zn/HCl$, $Zn/CH_3CO_2H$ and the like.

The compound of formula (Id) may be converted to a compound of formula (Ie) by using $NaNO_2$ in the presence of HCl or $CH_3COOH$ followed by $NaN_3$. The solvent used in the reaction may be selected from methanol, ethanol, ethylacetate, THF, ether, dioxan and the like. The temperature of the reaction may be maintained in the range of −40° C. to boiling temperature, preferably in the range of 0° C. to room temperature. The duration of the reaction may be in the range of 0.5 to 15 h, preferably in the range of 0.5 to 5 h.

Another embodiment of the present invention provides a novel intermediate of the formula (If),

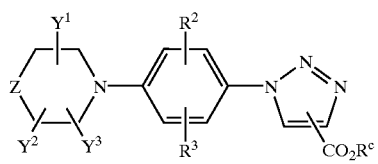

where $R^1$ represents substituted or unsubstituted $(C_1-C_{10})$ alkyl group such as methyl, ethyl, n-propyl, iso-propyl and the like; Z, $Y^1$, $Y^2$, $Y^3$, $R^2$ and $R^3$ are as defined earlier.

Yet another embodiment of the present invention provides a process for the preparation of novel intermediate of formula (If), which comprises:

(i) reacting the compound of formula (Ia),

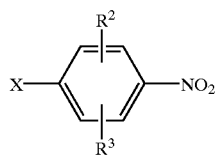

where X represents halogen atom such as fluorine, chlorine, bromine and the like; $R^2$ and $R^3$ are as defined earlier, with a compound of formula (Ib)

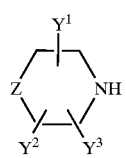

where Z, $Y^1$, $Y^2$ and $Y^3$ are as defined earlier, to produce a compound of formula (Ic)

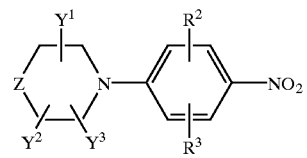

where Z, $Y^1$, $Y^2$, $Y^3$, $R^2$ and $R^3$ are as defined earlier, (ii) reducing the compound of formula (Ic), by using reducing agent to a compound of formula (Id)

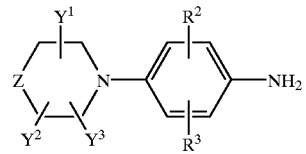

where Z, $Y^1$, $Y^2$, $Y^3$, $R^2$ and $R^3$ are as defined earlier, (iii) converting the compound of formula (Id), to a compound of formula (Ie)

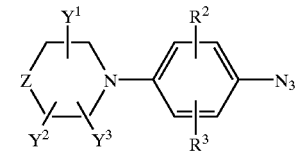

where Z, $Y^1$, $Y^2$, $Y^3$, $R^2$ and $R^3$ are as defined earlier and (iv) converting the compoundof formula (Ie),

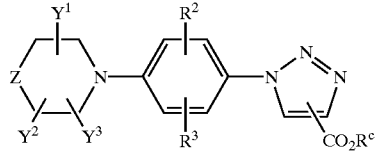

where $R^c$ represents substituted or unsubstituted $(C_1-C_{10})$ alkyl group such as methyl, ethyl, n-propyl, iso-propyl and the like; Z, $Y^1$, $Y^2$, $Y^3$, $R^2$ and $R^3$ are as defined earlier, to a compound of formula (If).

The compound of formula (Ic) may be prepared by reacting a compound of formula (Ia) with a compound of formula (Ib) by using a base such as KOH, NaOH, $K_2CO_3$, $Na_2CO_3$, NaH, KH, triethylamine, diisopropylethyl amine and the like. The reaction may be carried out using a solvent such as DMSO, DMF, THF, acetonitrile, chloroform, nitrobenzene and the like or mixtures thereof. The reaction may be carried out in inert atmosphere, which may be maintained using inert gases such as $N_2$ or Ar. The reaction may be carried out at a temperature in the range of 20 to 100° C., preferably at a temperature in the range of ambient −80° C. The reaction time may range from 1 to 15 h, preferably from 6 to 12 h.

The reduction of a compound of formula (Ic) to produce a compound of formula (Id) may be carried out in the presence of reducing agents such as $NiCl_2/NaBH_4$, lithium aluminium hydride (LAH), gaseous hydrogen and a catalyst such as Ru, Pd, Rh, Pt, Ni on solid beads such as charcoal, alumina, asbestos and the like. The reduction may be carried out in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature from 0 to 60° C., preferably at 0 to room temperature. The reaction time ranges from 0.5 to 48 h, preferably in the range of 0.5 to 5 h. The reduction may also be carried out by employing metal in mineral acids such Sn/HCl, Fe/HCl, Zn/HCl, Zn/$CH_3CO_2H$ and the like.

The compound of fomula (Id) may be converted to a compound of formula (Ie) by using $NaNO_2$ in the presence of HCl or $CH_3COOH$ followed by $NaN_3$. The solvent used in the reaction may be selected from methanol, ethanol, ethylacetate, THF, ether, dioxan and the like. The temperature of the reaction may be maintained in the range of –40° C. to boiling temperature, preferably in the range of 0° C. to room temperature. The duration of the reaction may be in the range of 0.5 to 15 h, preferably in the range of 0.5 to 5 h.

The compound of formula (If) may be prepared by heating a compound of formula (Ie) with esters (($C_1$-$C_{10}$) alkyl or aryl). The solvent used in the reaction may be selected from benzene, toluene, xylene, methylcyanide, THF and the like. The terriperature of the reaction may be maintained in the range of 0 to 200° C., preferably in the range of room temperature to boiling temperature of the solvent. The duration of the reaction may be in the range of 2 to 25 h, preferably 3 to 15 h.

Another embodiment of the present invention provides a novel intermediate of the formula (Ig),

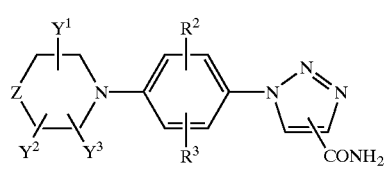

where all symbols are as defined earlier.

Yet another embodiment of the present invention provides a process for the preparation of novel intermediate of formula (Ig), which comprises:

(i) converting a compound of formula (If)

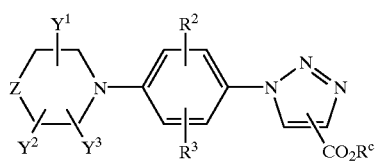

where $R^c$ represents substituted or unsubstituted ($C_1$-$C_{10}$) alkyl group such as methyl, ethyl, propyl and the like; and all other symbols are as defined earlier, to produce a compound of formula (Ig) and

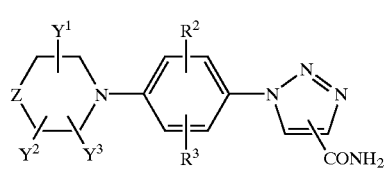

where all symbols are as defined earlier.

The conversion of compound of formula (If) to a compound of formula (Ig) may be carried out in the presence of ammonia solution in water or alcohol. The temperature of the reaction may be in the range of –40 to 50° C., preferably of 0° C. to room temperature. The duration of the reaction may be in the range of 0.5 to 12 h, preferably 0.5 to 4 h.

Another embodiment of the present invention provides a novel intermediate of the formula (Ij),

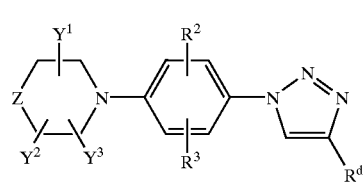

where $R^d$ represents substituted or unsubstituted groups selected from —($C_1$-$C_{10}$)alkyl, —$CO_2R^c$, —$CH_2OH$, —$CH_2NH_2$, —$CH_2N(Pthalimide)$, —$CH_2NH$—C(=S)S—O($C_1$-$C_{10}$)alkyl or —$CH_2NH$—C(=O)—($C_1$-$C_{10}$)alkyl and all other symbols are as defined earlier.

The compound of formula (Ij) represents the compounds of formula (I), when $R^d$ represents substituted or unsubstituted groups selected from —($C_1$-$C_{10}$)alkyl, —$CH_2OH$, —$CH_2NH_2$, —$CH_2N(Pthalimide)$, —$CH_2NH$—C(=S)S—O($C_1$-$C_{10}$)alkyl, —$CH_2NH$—C(=O)($C_1$-$C_{10}$)alkyl.

Still yet another embodiment of the present invention provides a process for the preparation of novel intermediate of formula (Ij), which comprises:

(i) converting the compound of formula (Ie),

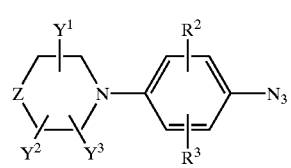

where Z, $Y^1$, $Y^2$, $Y^3$, $R^2$ and $R^3$ are as defined earlier, with $$\equiv\!-\!R^d \qquad\qquad (Ih)$$

where $R^d$ is as defined above, to a compound of formula (Ij)

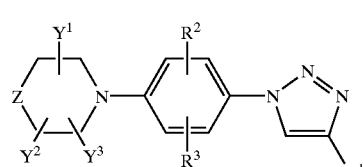

where Z, $Y^1$, $Y^2$, $Y^3$, $R^d$, $R^2$ and $R^3$ are as defined earlier.

The compound of formula (Ij) may be prepared by reacting the compound of formula (Ie) with a compound of formula (Ih), in the presence of a base such as triethylamine, ethyldiisopropylamine, DABCO and the like. The reaction may be carried out in the presence of a solvent such as dichloromethane, chloroform, tetrahydrofuran, dimethylformamide, dimethylsulfoxide, acetonitrile and the like. The reaction may be carried out in the presence of Cu (1)I.

It is appreciated that in any of the above-mentioned reactions, any reactive group in the substrate molecule may be protected according to conventional chemical practice. Suitable protecting groups in any of the above mentioned reactions are tertiarybutyldimethylsilyl, methoxyrnethyl, triphenyl methyl, benzyloxycarbonyl, tetrahydropyran (THP) etc, to protect hydroxyl or phenolic hydroxy group; N-tert-butoxycarhonyl (N-Boc), N-benzyloxycarbonyl (N-Cbz), N-9-fluorenyl methoxy carbonyl (—N-FMOC), benzophenoneimine, propargyloxy carbonyl (POC) etc, for protection of amino or amino group, acetal protection for aldehyde, ketal protection for ketone and the like. The methods of formation and removal of such protecting groups are those conventional methods appropriate to the molecule being protected.

Regioisomers are isomers that differ by their functional groups. The regioisomers of compound of formula (I) may be prepared by modifying the reaction conditions, use of reagents like acid to base or base to acid or by reaction with free base hydrazine instead of its salt with diketone. The molar proportion also can change the regiosiomer formation.

The enantiomers may be prepared by using reactants in their single enantiomeric form in the process wherever applicable or by conducting the reaction in the presence of reagents or catalysts in their single enantiomeric form. The single enantiomers may also be prepared by resolving the racemic mixture by conventional methods. The stereoisomers of the compounds forming part of this invention may be prepared by using reactants in their single enantiomeric form in the process wherever possible or by conducting the reaction in the presence of reagents or catalysts in their single enantiomer fonn or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). Where appropriate the compounds of formula (I) maybe resolved by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

The pharmaceutically acceptable salts are prepared by reacting the compounds of formula (I) wherever applicable with 1 to 4 equivalents of a base such as sodium hydroxide, sodium metlioxide, sodium hydride, potassium t-butoxide, calcium hydroxide, magnesium hydroxide and the like, in the presence of a solvent like ether, THF, methanol, t-butanol, dioxane, isopropanol, ethanol etc. Mixture of solvents may be used. Organic bases like lysine, arginine, diethanolamine, choline, troniethamine, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonie acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in the presence of a solvent like ethyl acetate, ether, alcohols, acetone, THF, dioxane etc. Mixture of solvent may also be used. The salts of amino acid groups and other groups may be prepared by reacting the compounds of formula (I) with the respective groups in the presence of a solvent like alcohols, ketones, ether etc. Mixture of solvents may be used.

Various polymorphs of a compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Heating or melting the compound followed by gradual or fast cooling may also obtain polymorphs. The presence of polymorphs may be determined by solid probe nmr spectroscopy, IR spectroscopy, differential scanning calorimetry, powder X-ray diffraction or such other techniques.

The present invention also provides pharmaceutical compositions, containing compounds of the general formula (I), as defined above, their derivatives, their analogs, their tautomeric forms, their stereoisomers, their polymorphs, their pharmaceutically acceptable salts or their pharmaceutically acceptable solvates in combination with the usual pharmaceutically employed carriers, diluents and die like. The pharmaceutical compositions according to this invention can be used for the treatment of bacterial infections, They can also be used for the treatment of bacterial infections associated with multidrug resistance. The pharmaceutical compositions according to this invention can also be administered prophylatically for the prevention of bacterial infections in a patient at risk of developing a bacterial infection. Such patients include but are not limited to patients who are pre- or post-surgical, immunocompromised, or hospitalized and can be used for the treatment/prevention of bacterial infections associated with multidrug resistance.

Pharmaceutically acceptable solvates of compound of formula (I) forning part of this invention may be prepared by conventional methods such as dissolving the compounds of formula (I) in the presence of a solvent such as water, methanol, ethanol etc., preferably water and recrystallizing by using different crystallization techniques.

The regioisomers of compound of formula (I) may be prepared by modifying the reaction conditions, use of reagents like acid to base or base to acid or by reaction with free base hydrazine instead of its salt with diketone. The molar proportion also can change the regioisomer formation.

The phannaceutical compositions may be in the forms normally employed, such as tablets, capsules, powders, syrups, solutions, suspensions and the like, may contain flavorants, sweeteners etc. in suitable solid or liquid carriers or dilucnts, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

Suitable pharmaceutically acceptable carriers include solid fillers or diluents and sterile aqueous or organic solutions. The active compounds will be present in such pharmaceutical compositions in the amounts sufficient to provide the desired dosage in the range as described above. Thus, for oral administration, the compounds can be combined with a suitable solid, liquid carrier or diluent toform capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

In addition to the compounds of formula (I) the phannaceutical compositions of the present invention may also contain or be co-administered with one or more known drugs selected from other clinically useful antibacterial agents such as β-lactams or aminoglycosides. These may include penicillins such as oxacillin or flucloxacillin and carbapenems such as meropenem or imiphenem to broaden the therapeutic effectiveness against, for example, methicillin-resistant staphylococci. Compounds of the formula (I) of the present invention may also contain or be co-admistered with bactericidal/permeability-increasing protein product (BPI) or efflux pump inhibitors to improve activity against gram negative bacteria and bacteria resistant to antimicrobial agents.

The compounds of the formula (I) as defined above are clinically administered to mammals, including human beings, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.5 mg/kg to about 50 mg/kg body weight of the subject per (lay administered singly or as a divided dose. However, the optimum dosage whether for prevention or treatment for the individual subject being treated will be determined by the person responsible for treatment, generally smaller doses being administered initially and thereafter increments made to determine the most suitable dosage.

An effective amount means that amount of a drug or pharmaceutical agent that will elicit the biological or medical response of a tissue, system, animal or human that is being sought.

The invention is explained in detail in the examples given below which are provided by way of illustration only and therefore should not be construed to limit the scope of the invention.

PREPARATION 1

4-(2,6-Difluoro-4-nitrophenyl)morpholine

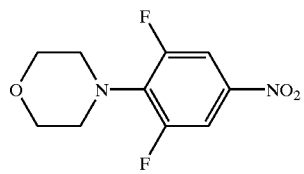

Morpholine (1.2 g, 14.12 mmol) was added to a stirring solution of 3,4,5-trifluoronitro benzene (1 g, 5.65 mmol) in acetonitrile (15 mL) and the reaction mixture was refluxed for 5 h. A viscous liquid was obtained upon concentration, which was then poured into crushed ice. The solid thus obtained was filtered off and dried under reduced pressure to obtain the title compound (1.2 g, 88%).

$^1$HMR (CDCl$_3$): δ 7.90–7.70 (m, 2H), 3.90–3.70 (m, 4H), 3.50–3.30 (m, 4H).

MS (m/e): 245 (M$^+$+1), 230, 215.

PREPARATION 2

4-(2-Fluoro-4-nitrophenyl)morpholine

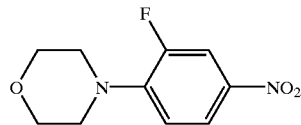

The title compound (1.2 g, 84%) was obtained from 3,4-difluoro nitrobenzene (1.0 g, 6.29 mmol) and morpholine (1.0 g, 12.5 mmol) by a procedure as described in Preparation 1.

$^1$H NMR (CDCl$_3$): δ 8.05–7.80 (m, 2H), 6.90 (t, J=8.8 Hz, 1H), 3.95–3.80 (m, 4H), 3.35–3.20 (m, 4H).

MS (m/e): 226 (M$^+$), 168, 138.

PREPARATION 3

4-(2,6-Difluoro-4-nitrophenyl)thiomorpholine

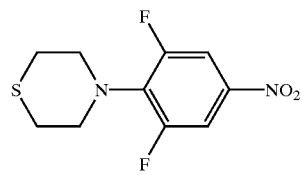

Thiomorpholine (728 mg, 7.06 mmol) was added to a stirring solution of 3,4,5-trifluoronitro benzene (500 mg, 2.82 mmol) in acetonitrile (15 mL) and the reaction mixture was refluxed for 5 h. Evaporation of the solvent in a rotavapor under reduced pressure left a pasty mass which was dissolved in ethyl acetate (50 mL). Ethyl acetate portion was washed with water (30 mL×2) followed by brine (30 mL) and dried over sodium sulfate. Removal of volatiles yielded the title compound as yellow solid (650 mg, 85%).

$^1$H NMR (CDCl$_3$): δ 7.90–7.70 (m, 2H), 3.60–3.40 (m, 4H), 2.80–2.60 (m, 4H).

MS (m/e): 261 (M$^+$+1), 186.

PREPARATION 4

4-(2-Fluoro-4-nitrophenyl)thiomorpholine

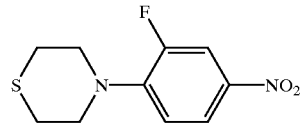

The title compound (650 mg, 86%) was obtained from thiomorpholine (810 g, 7.86 mmol) and 3,4-difluoronitrobenzene (500 mg, 3.4 mmol) by a procedure as described in Preparation 3.

$^1$H NMR (CDCl$_3$): δ 8.05–7.80 (m, 2H), 6.90 (t, J=8.8 Hz, 1H), 3.70–3.50 (m, 4H), 2.90–2.70 (m, 4H).

MS (m/e): 243 (M$^+$+1), 168.

PREPARATION 5

1-(2-Fluoro-4-nitro-phenyl)-piperidin-4-one

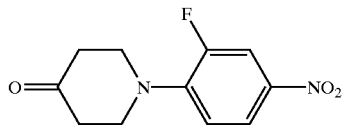

To a stirred solution of 4-piperidinone (9.7 g, 63 mmol) and dry potassium carbonate (21.6 g, 157 mmol) in DMF (30 ml) was added 3,4-difluoro nitrobenzene (10 g, 63 mmol) and reaction mixture was heated to 90° C. for 3 h. The reaction mixture was poured into ice-water arid extracted with ethyl acetate (100 ml×2). Combined organic layer was washed with water followed by brine and dried over sodium sulfate. Evaporation of volatiles and purification of the resulting residue by silica gel column chromatography (ethyl acetate/pet. ether, 1:4) yielded the title compound (7 g, 50%).

$^1$H NMR (CDCl$_3$): δ 8.10–7.91 (m, 2H), 6.97 (t, J=8.7 Hz, 1H), 3.61 (t, J=6.1 Hz, 4H), 2.62 (t, J=6.1 Hz, 4H).

MS (m/e): 239 (M$^+$+1), 168.

PREPARATION 6

3,5-Difluoro-4-morpbolin-4-yl-plienylamine

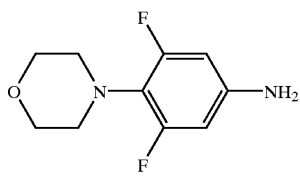

Nickel chloride hexahydrate (2.32 g, 9.83 mmol) was added to a solution of 4-(2,6-difluoro-4-nitrophenyl)morpholine (1.2 g, 4.92 mmol), obtained in Preparation 1, in methanol (50 mL). NaBH$_4$ (749 mg, 19.6 mmol) was added to the reaction mixture in portions and was allowed to stir at room temperature for 0.5 h. It was diluted with ethyl acetate (100 mL) and the organic portion was washed with water (60 mL×2) followed by brine (50 mL) and dried over sodium sulfate. Evaporation of the volatiles produced the title compound (0.95 g, 90%).

$^1$H NMR (CDCl$_3$): δ 6.30–6.10 (m, 2H), 3.90–3.70 (m, 4H), 3.10–2.90 (m, 4H).

MS (m/e): 215 (M$^+$+1)

PREPARATION 7

3-Fluoro-4-morpbolin-4-yl-phenylamine

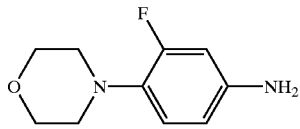

The title compound (0.96 g, 96%) was obtained from 4-(2-fluoro-4-nitrophenyl)morpholine (1.2 g, 5.30 mmol), as prepared in Prepartion 2, by a procedure as described in Preparation 6.

$^1$H NMR (CDCl$_3$): δ 7.0–6.80 (m, 1H), 6.50–6.30 (m, 2H), 3.90–3.70 (br s, 4H), 3.10–2.90 (br s, 4H).

MS (m/e): 197 (M$^+$+1).

PREPARATION 8

3,5-Difluoro-4-thiomorpholin-4-yl-phenylamine

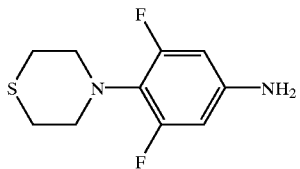

Sodium borohydride (285 mg, 7.5 mmol) was added to a stirring solution of NiCl$_2$.6H$_2$O (1.16 g, 5.0 mmol) and 4-(2,6-difluoro-4-nitrophenyl)thiomorpholine, obtain in Preparation 3, in methanol (30 mL). The reaction mixture was diluted with ethyl acetate (50 mL) after 0.5 h and the organic portion was washed with water (30 mL×2) followed by brine (30 mL) and dried over sodium sulfate. Evaporation of the volatiles yielded the title compound as light brown solid (400 mg, 70%).

$^1$H NMR (CDCl$_3$): δ 6.30–6.10 (m, 2H), 3.40–3.20 (m, 4H), 2.80–2.60 (m, 4H).

MS (m/e): 231 (M$^+$+1), 156.

PREPARATION 9

3-Fluoro-4-thiomorpholin-4-yl-phenylamine

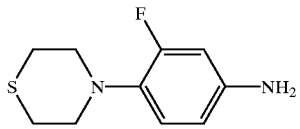

The title compound (0.41 g, 71%) was obtained from 4-(2-fluoro-4-nitrophenyl)thiomorpliolinie (0.5 g, 2.06 mmol), as reported in Prepartion 4, by a similar procedure ast described in Preparation 8.

$^1$H NMR (CDCl$_3$): δ 6.80 (t, J=9.04 Hz, 1H), 6.50–6.30 (m, 2H), 3.30–3.10 (m, 4H), 2.80–2.70 (m, 4H).

MS (m/e): 213 (M$^+$+1), 212, 138.

PREPARATION 10

1-(4-Amino-2-fluoro-plienyl)-piperidin-4-one

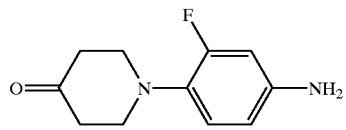

Iron powder (16.4 g, 294 mmol) was slowly added to an ice-cold solution of 1-(2-fluoro-4-nitro-phenyl)-piperidin-4-one (7 g, 29.4 mmol), obtained in Preparation 5, in ethanolic HCl (50 ml) at 0° C. and stirred at the same temperature for 2 h. The reaction mixture was basified by the addition of sodium carbonate and pH of the solution was brought to 8. It was then diluted with ethyl acetate (100 ml) and the aqueous layer was separated. The aqueous layer was further extracted with ethyl acetate (100 ml×2). Combined organic extract was washed with water followed by brine and dried over sodium sulfate. Removal of volatiles left a pasty mass (7 g), which was used for the next step.

$^1$H NMR (CDCl$_3$): δ 6.91 (t, J=8.6 Hz, 1H), 6.49–6.30 (m, 2H), 3.30 (t, J=5.8 Hz, 4H), 2.61 (t, J=5.8 Hz, 4H).

MS (m/e): 209 (M$^+$+1).

PREPARATION 11

4-(4-Azido-2,6-difluorophenyl)morpholine

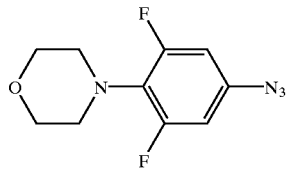

Sodium nitrite (0.91 g, 13.3 mmol) was added to an ice-cooled solution of 3,5-difluoro-4-morpholin-4-yl-phenylamine (0.95 g, 4.4 mmol), obtained in Preparation 6, in 6N HCl (30 mL) and the resulting yellow solution was stirred at 0° C. for 2 h. To this mixture was added an aqueous solution containing sodium azide (0.575 g, 8.86 mmol) and sodium acetate (57.5 g, 88.6 mmol). The reaction mixture was then extracted with ethyl acetate (50 mL×2) and the combined extracts were washed with 5% sodium bicarbonate solution followed by brine and dried over sodium sulfate. Evaporation of volatiles yielded the title compound as brown solid (1 g, 96%).

$^1$HNMR (CDCl$_3$): δ 6.70–6.50 (m, 2H), 3.90–3.70 (m, 4H), 3.20–3.02 (4H).

MS (m/e): 241 (M$^+$+1), 212 (—N$_2$), 154, 91.

PREPARATION 12

4-(4-Azido-2-fluorophenyl)morpholine

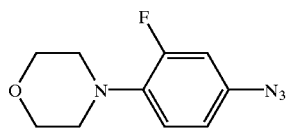

The title compound (1.03 g, 91%) was obtained from 3-fluoro-4-morpholin-4-yl-phenylamine (1 g, 5.10 mmol), as reported in Preparation 7, by a procedure as described in Preparation 11.

$^1$H NMR (CDCl$_3$): δ 6.98 (t, J=8.7 Hz, 1H), 6.80–6.70 (m, 2H), 4.01–3.80 (m, 4H), 3.20–3.01 (m, 4H).

MS (m/e): 223 (M$^+$+1), 195.

PREPARATION 13

4-(4-Azido-2,6-difluorophenyl)thiomorpholine

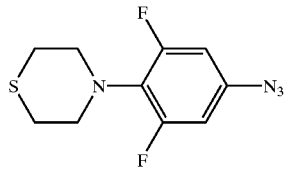

The title compound (2.0 g, 90%) was obtained from 3,5-difluoro-4-thiomorpholin-4-yl-phenylamine (2.0 g, 8.7 mmol), as reported in Preparation 8, by a procedure as described in Preparation 11.

$^1$H NMR (CDCl$_3$): δ 6.60–6.40 (m, 2H), 3.40–3.20 (m, 4H), 2.80–2.60 (m, 4H).

MS (m/e): 257 (M$^+$+1), 228 (—N$_2$), 154.

PREPARATION 14

4-(4-Azido-2-fluorophenyl)thiomorpholine

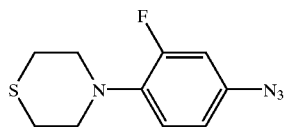

The title compound (2.1 g, 93%) was obtained from 3-fluoro-4-thiomorpholin-4-yl-phenylamine (2 g, 9.4 mmol), as reported in Preparation 9, by a procedure as described in Preparation 11.

$^1$H NMR (CDCl$_3$): δ 7.00–6.90 (t, J=8.9 Hz, 1H), 6.90–6.80 (m, 2H), 3.40–3.20 (m, 4), 2.90–2.70 (m, 4H).

MS (m/e): 239 (M$^+$+1), 210 (—N$_2$).

PREPARATION 15

1-(4-Azido-2-fluoro-phenyl)-piperidin-4-one

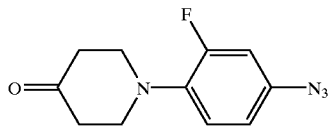

Sodium nitrite (9.9 g, 144 mmol) was added to an ice-cooled solution of 1-(4-amino-2-fluoro-phenyl)-piperidin-4-one (15 g, 72 mmol), obtained in Preparation 10, in 6 N HCl (60 ml) and the resulting solution was stirred at 0° C. for 0.5 h. An aqueous solution of sodium azide (9.4 g, 144 mmol) and sodium acetate (118 g, 1.44 mol) was then added. The reaction mixture was extracted with ethyl acetate (100 ml×2) and the combined extracts were washed with 5% sodium bicarbonate solution followed by brine and dried over sodium sulfate. Removal of volatiles left a crude product, which was purified by silica gel column chromatography (ethyl acetate/pet. ether, 1:1) to obtain the title azide (10 g, 63%).

$^1$H NMR (CDCl$_3$): δ 6.91 (t, J=8.6 Hz, 1H), 6.77 (d, J=10.4 Hz, 2H), 3.36 (t, J=5.9 Hz, 4H), 2.60 (t, J=5.9 Hz, 4H).

MS (m/e): 235 (M$^+$+1), 219, 206.

PREPARATION 16

1-(2,6-Difluoro-4-nitrophenyl)-piperidin-4-one

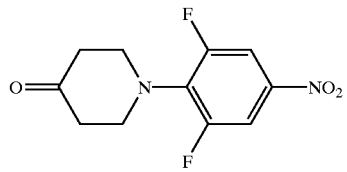

To a suspension of anhydrous potassium carbonate (11.80 g, 85.90 mmol) in DMF (30 ml) was added a solution of 4-piperidinone (7.20 g, 47.2 mmol) in DMF (5 ml) followed by the addition of 3,4,5-trifluoronitrobenzene (7.00 g, 42.8 mmol) and stirred at room temperature for 3 h. The reaction mixture was poured onto ice water and the resulting solid was filtered off. Drying the solid under vacuum yielded the title compound as yellow powder (4.50 g, 45%).

$^1$H NMR (CDCl$_3$): δ 7.70 (d, J=9.4 Hz, 2H), 3.57 (t, J=5.9 Hz, 4H), 2.54 (t, J=5.9 Hz, 4Hz).

MS (m/e): 257 (M$^+$+1), 95.

PREPARATION 17

1-(4-Amino-2,6-difluorophenyl)-piperidin-4-one

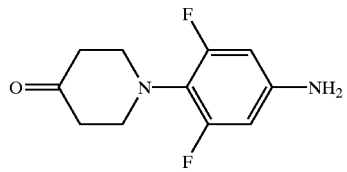

1-(2,6-Difluoro-4-nitrophenyl)-piperidin-4-one (4.50 g, 17.57 mniol), obtained in Preparation 16, was added to a warm (95° C.) solution of ammonium chloride (18.60 g, 351.50 mmol) in ethanol (40 ml) and water (20 ml) followed by the addition of iron powder (2.95 g, 52.7 inmol) in portions over 0.5 h and stirred at the same temperature for additional 0.5 h. The reaction mixture was extracted with ethylacetate (2×250 ml). The combined extract was washed with water followed by brine and dried over sodium sulfate. Evaporation of volatiles on rotavapor yielded the title compound as viscous liquid (4.00 g, 63%).

$^1$H NMR (CDCl$_3$): δ 6.18 (d, J=10.4 Hz, 2H), 3.36 (t, J=1.7 Hz, 4H), 2.55 (t, J=5.7 Hz, 4H).

MS (m/e): 227 (M$^+$+1), 209, 183.

PREPARATION 18

1-Azido-2,6-difluorophenyl)-piperidin-4-one

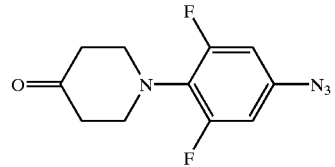

Sodium nitrite (2.40 g, 35.30 mmol) was added to an ice cooled solution of 1-(4-amino-2,6-difluorophenyl)-piperidin-4-one (4.00 g, 17.69 mmol), obtained in Preparation 17, in 6 N HCl (10 ml) and the resulting solution was stirred at 0° C. for 0.5 h. The reaction mixture was quenched with an aqueous solution of sodium azide (2.30 g, 35.3 mmol) and sodium acetate (29.0 g, 353 mmol). The reaction mixture was extracted with ethylacetate (100 ml×2) and the combined extract was washed with water followed by brine. The ethylacetate extract was dried over sodium sulfate and concentrated under reduced pressure. The resulting residue was purified by column chromatography (ethylacetate/pet ether; 1:9) to yield the title compound (2.20 g, 55%).

$^1$H NMR (CDCl$_3$): δ 6.55 (d, J=9.4 Hz, 2H), 3.43 (t, J=5.9 Hz, 4H), 2.57 (t, J=5.9 Hz, 4H).

MS (m/e): 253 (M$^+$+1), 224, 212.

PREPARATION 19

Prop-2-ynyl-thiocarbamie acid 0-methyl ester

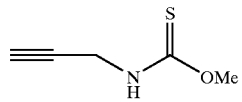

To an ice cooled solution of propargyl amine (10 g, 182 mmol) and tricthyl amine (38 ml, 273 mmol) in THF (300 ml) was added a solution of carbon disulfide (13.8 ml, 218 mmol) in THF, over a period of 0.5 h. A solution of ethylchloroformate (17.4 ml, 182 mmol) in THF was then added to the reaction mixture. The reaction mixture was allowed to stir at room temperature for 15 min. Then the reaction mixture was filtered off and the filtrate was concentrated at 35° C. under reduced pressure. The resulting residue was diluted with methanol (200 ml) and the solution was refluxed for 2 h. Evaporation of volatiles left a pasty mass, which was purified by passing through a silica gel column (pet. ether/ethylacetate, 1:9) to obtain the title compound as white solid (13.6 g, 56%). Mp. 70–72° C.

$^1$H NMR (CDCl$_3$): δ 6.65 & 6.30 (2 bs, 1H, rotamers in a ration of 1:4), 4.35–4.25 (m, 2H), 4.04 and 3.96 (2s, 3H, rotamers in the ration of 1:4), 2.25 (t, J=2.4 Hz, 1H).

MS (m/e): 130 (M$^+$+1), 129, 114.

PREPARATION 20

1-(3,5-Difluoro-4-morpholin-4-yl-phenyl)-1H-[1,2,3]triazole-4-carboxylic acid ethyl ester

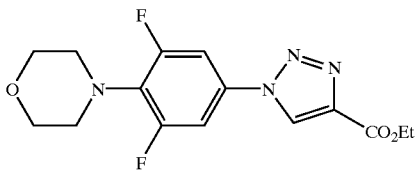

A solution of 4-(4-azido-2,6-difluorophenyl)morpholine (1 g, 4.16 mmol), obtained in Preparation 11, and ethyl propiolate (1.2 g, 12.5 mmol) in benzene (50 mL) was refluxed for 16 h. The precipitate of the required isomer was collected after the reaction mixture was cooled down to room temperature to yield the title compound (0.8 g, 60%).

$^1$H NMR (CDCl$_3$): δ 8.42 (s, 1H), 7.40–7.30 (m, 2H), 4.60–4.40 (q, J=7.3 Hz, 2H), 3.90–3.70 (m, 4H), 3.40–3.20 (br s, 4H), 1.44 (t, J=7.3 Hz, 3H).

MS (m/e): 339 (M$^+$+1).

PREPARATION 21

1-(3-Fluoro-4-morpholin-4-yl-phenyl)-1H-[1,2,3]triazole-4-carboxylic acid ethyl ester

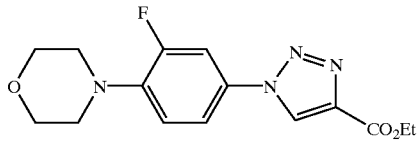

The title compound (0.9 g, 60%) was obtained from 4-(4-azido-2-fluorophenyl)morpholine (1.03 g, 4.63 mmol), as reported in preparation 12, by a procedure as described in Preparation 20.

$^1$H NMR (CDCl$_3$): δ 8.44 (s, 1H), 7.60–7.40 (m, 2H), 7.06 (t, J=8.7 Hz, 1H), 4.50 (q, J=7.3 Hz, 2H), 4.00–3.80 (m, 4H), 3.30–3.10 (m, 4H), 1.44 (t, J=7.3 Hz, 3H).

MS (m/e): 321 (M$^+$+1), 234, 162.

PREPARATION 22

1-(3,5-Difluoro-4-thiomorpholin-4-yl-phenyl)-1H-[1,2,3]triazole-4-carboxylic acid ethyl ester

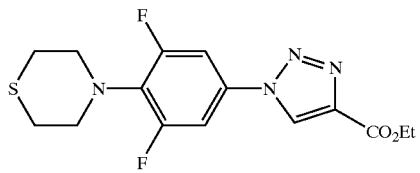

To a stirring solution of 4-(4-azido-2,6-difluorophenyl)thiomorpholine (1 g, 3.9 mmol), obtained in Preparation 13, in acetonitrile (10 mL) was. added ethyl propiolate (0.45 mL, 3.9 mmol) followed by N-ethyldiisopropyl amine (10 mL). Cuprous iodide (0.74 g, 3.9 mmol) was then added to the reaction mixture in portion while the title compound started precipitating out. The precipitation was completed within 10 min. and it was allowed to stir for additional 10 min. The precipitate was collected on a buchner funnel, which was purified by column chromatography on silica gel to yield the tilte compound as yellow solid (1.24 g, 90%).

$^1$H NMR (DMSO-d$_6$): δ 9.49 (s, 1H), 7.83 (d, J=9.7 Hz, 2H), 4.37 (q, J=7.3 Hz, 2H), 3.52–3.24 (m, 4H), 2.81–2.62 (m, 4H), 1.34 (t, J=7.3 Hz, 3H).

MS (m/e): 355 (M$^+$+1), 181.

PREPARATION 23

1-(3-Fluoro-4-morpholin-4-yl-phenyl)-1H-[1,2,3]triazole-4-carboxylic acid ethyl ester

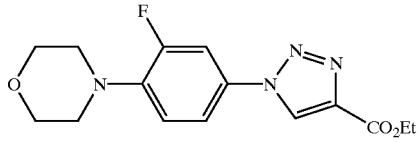

The title compound (1.26 g, 88%) was obtained from 4-(4-azido-2-fluorophenyl)morpholine (1 g, 4.6 mmol), as reported in Preparation 12, by a procedure as described in Preparation 22. The spectral data is in good agreement with the compound reported in Preparation 21.

EXAMPLE 1

[1-(3,5-Difluoro-4-morpholin-4-yl-phenyl)-1H-[1,2,3]triazol-4-yl]-methanol

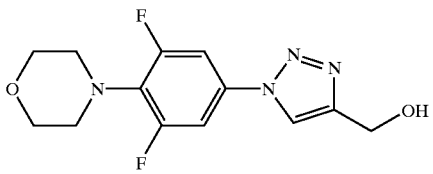

A solution of 1-(3,5-difluoro-4-morpholin-4-yl-phenyl)-1H-[1,2,3]triazole-4-carboxylic acid ethyl ester (0.8 g, 2.3 mmol), obtained in preparation 20, in anhydrous THF (30 mL) was treated with lithium borohydride (0.1 g, 4.73 mmol) and the reaction mixture was allowed to stir at room temperature for 18 h. The reaction mixture was then extracted with ethyl acetate (70 mL×2) after the addition of saturated ammonium chloride solution (10 mL). Combined ethyl acetate portion was washed with brine and dried over sodium sulfate. Evaporation of solvent afforded an oil, which was purified by silica gel column chromatography (eluent CHCl$_3$/MeOH, 95/5) to yield the title compound as white solid (0.6 g, 80%).

$^1$H NMR (CDCl$_3$): δ 8.16 (s, 1H), 7.50–7.30 (m, 2H), 5.01 (br s, 1H), 4.79 (s, 2H), 3.90–3.70 (m, 4H), 3.30–3.10 (m, 4H).

MS (m/e): 297 (M$^+$+1), 289, 268, 251.

EXAMPLES 2

[1-(3-Fluoro-4-morpholin-4-yl-phenyl)-1H-[1,2,3]triazol-4-yl]-methanol

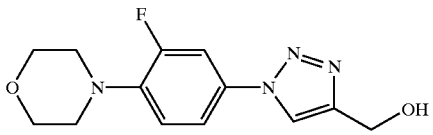

The title compound (0.69 g, 86%) was obtained from 1-(3-Fluoro-4-morpholin-4-yl-phenyl)-1H-[1,2,3]triazole-4-carboxylic acid ethyl ester (0.9 g, 2.8 mmol), as reported in Preparation 21, by a procedure as described in Example 1. Mp. 198° C.

$^1$H NMR (CDCl$_3$): δ 8.26 (s, 1H), 7.70–7.50 (m, 2H), 7.10 (t, J=8.8 Hz, 1H), 5.17 (t, J=5.4 Hz, 1H), 4.73 (d, J=5.4 Hz, 2H), 3.95–3.80 (m, 4H), 3.20–3.01 (m, 4H).

MS (m/e): 278 (M$^+$), 250, 233, 192, 175.

EXAMPLE 3

1-(3,5-Difluoro-4-thiomorpholin-4-yl-phenyl)-1H-[1,2,3]triazol-4-yl]-methanol & [3-(3,5-Difluoro-4-thiomorpliolin-4-yl-phenyl)-3H-[1,2,3]triazol-5-yl]-methanol

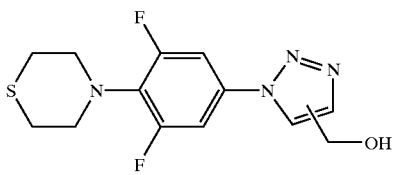

A solution of 4-(4-azido-2,6-difluorophenyl)thiomorpholine (2.0 g, 7.8 mmol), obtained in Preparation 13, and propargyl alcohol (1.3 g, 23.4 mmol) in toluene (75 mL) was refluxed for 15 h. Evaporation of toluene left a pasty mass (2.2 g) containing both the regioisomers.

MS (m/e) 313 (M⁺+1).

EXAMPLE 4

[1-(3-Fluoro-4-thiomorpholin-4-yl-phenyl)-1H-[1,2,3]triazol-4-yl]-methanol & [3-(3-Fluoro-4-thiomorpholin-4-yl-phenyl)-3H-[1,2,3]triazol-5-yl]-methanol

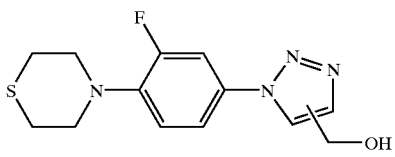

A solution of 4-(4-azido-2-fluorophenyl)thiomorpholine (2.0 g, 8.4 mmol), obtained in Preparation 14, and propargyl alcohol (1.4 g, 25.2 mmol) in toluene (75 mL) was refluxed for 15 h. Evaporation of toluene left a pasty mass (2.2 g) containing both the regioisomcrs.

MS (m/e) 295 (M⁺+1).

EXAMPLE 5

[1-(3,5-Difluoro-4-thiomorpholin-4-yl-phenyl)-1H-[1,2,3]triazol-4-yl]-methanol

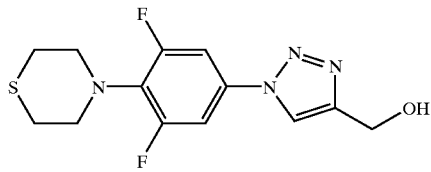

To a suspension of lithium aluminum hydride (161 mg, 4.24 mmol) in dry THF (10 mL) was added a solution of 1-(3,5-difluoro-4-thiomorpholin-4-yl-phellyl)-1H-[1,2,3]triazole-4-carboxylic acid ethyl ester (1.0 g, 2.8 mmol), obtained in Preparation 22, in THF (10 mL) at 0° C. and stirred for 0.5 h. The reaction mixture was then quenched with saturated solution of sodium sulfate and filtered. The residue was washed with ethyl acetate and the combined filtrate was concentrated to yield the title alcohol (0.7 g, 88%).

¹H NMR (DMSO-d₆): δ 8.71 (s, 1H), 7.73 (d, J=9.7 Hz, 2H), 5.38 (br s, 1H), 4.60 (s, 2H), 3.45–3.24 (br s, 4H), 2.81–2.62 (m, 4H).

MS (m/e): 313 (M⁺+1), 295, 181, 130.

EXAMPLE 6

1-[2-Fluoro-4-(4-hydroxymethyl-[1,2,3]triazol-1-yl)-phenyl]-piperidin-4-one & 1-[2-Fluoro-4-(5-hydroxymethyl-[1,2,3]triazol-1-yl)-phenyl]-piperidin-4-one

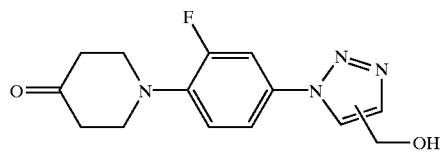

1-(4-Azido-2-fluoro-phenyl)-piperidin-4-one (10 g, 45 mmol), obtained in Preparation 15, was refluxed with propargyl alcohol (7.7 g, 138 mmol) in toluene (1 L) for 16 h. The resultant mixture of regioisomeric alcohols was subjected to the next reaction after removal of toluene.

MS (m/e): 291 (M⁺+1).

EXAMPLE 7

Methanesulfonic acid 1-(3,5-difluoro-4-morpholin-4-yl-phenyl)-1H-[1,2,3]triazol-4-ylmethyl ester

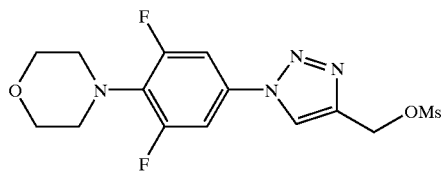

Methanesulfonyl chloride (0.1 mL, 2.23 mmol) was added dropwise to a solution of [1-(3,5-diflluoro-4-morpholin-4-yl-phenyl)-1H-[1,2,3]triazol-4-yl]-methanol (0.6 g, 2.02 mmol), obtained in Example 1, and Et₃N (0.6 mL, 4.4 mmol) in CH₂Cl₂ (30 mL) at 0° C. After stirring for 45 min the reaction mixture was washed successively with water, aqueous NaHCO₃ and brine and dried over sodium sulfate. Evaporation of volatiles left the title compound as oily liquid (0.7 g, 93%).

EXAMPLE 8

Methanesulfonic acid 1-(3-fluoro-4-morpholin-4-yl-phenyl)-1H-[1,2,3]triazol-4-ylmethyl ester

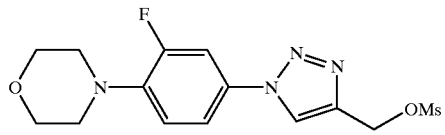

The title compound (0.8 g, 90%) was obtained from [1-(3-fluoro-4-morpholin-4-yl-phenyl)-1H-[1,2,3]triazol-4-yl]-methanol (0.67 g, 3.76 mmol), as reported in Example 2, by a procedure as described in Example 7.

EXAMPLE 9

Methanesulfonic acid 1-(3,5-difluoro-4-thiomorpholin-4-yl-phenyl)-1H-[1,2,3]triazol-4-ylmethyl ester & Methanesulfonic acid 3-(3,5-difuoro-4-thiomorpholin-4-yl-phenyl)-3H-[1,2,3]triazol-5-ylmethyl ester

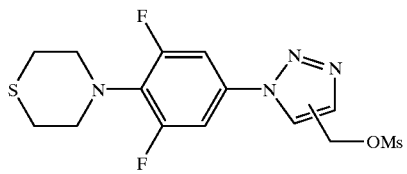

The title compounds (2.2 g, 81%) were obtained from a mixture of [1-(3,5-difluoro-4-thiomorpholin-4-yl-phenyl)-1H-[1,2,3]triazol-4-yl]-methanol & [3-(3,5-difluoro-4-thiomorpholin-4-yl-phenyl)-3H-[1,2,3]triazol-5-yl]-methanol (2.2 g), as reported in Example 3, by a procedure as described in Example 7.

EXAMPLE 10

Methanesulfonic acid 1-(3-fluoro-4-thiomorpholin-4-yl-phenyl)-1H-[1,2,3]triazol-4-ylmethyl ester & Methanesulfonlic acid 1-(3-fluoro-4-thiomorpholin-4-yl-phenyl)-3H-[1,2,3itriazol-5-ylmethyl ester

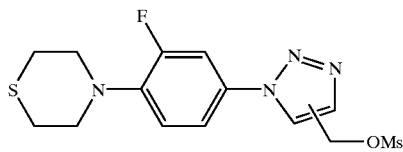

The title compounds (2.2 g, 79%) were obtained from a mixture of [1-(3-fluoro-4-thiomorpholin-4-yl-phenyl)-1H-[1,2,3]triazol-4-yl]-methanol & [3-(3-fluoro-4-thiomorpholin-4-yl-phenyl)-3H-[1,2,3]triazol-5-yl]-methanol (2.2 g), as reported in Example 4, by a procedure as described in Example 7.

EXAMPLE 11

4-[4-(4-Azidomethyl-[1,2,3]triazol-1-yl)-2,6-difluorophenyl]-morpholine

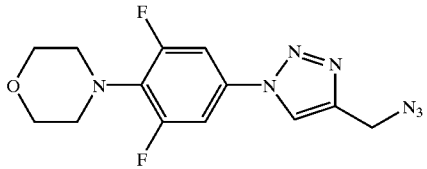

A solution of methanesulfonic acid 1-(3,5-difluoro-4-morpholin-4-yl-phenyl)-1H-[1,2,3]triazol-4-ylmethyl ester (0.7 g, 1.87 mmol), obtained in Example 7, and sodium azide (0.3 g, 5.61 mmol) in dimethylformamide (30 mL) was stirred at 60° C. for 3 h. The residue obtained after evaporation of DMF, under reduced pressure, was dissolved in ethyl acetate and the resulting solution was washed with water followed by brine and dried over sodium sulfate. Evaporation of solvent produced the title compound as light brown solid (0.5 g, 83%).

$^1$H NMR (CDCl$_3$): δ 7.89 (s, 1H), 7.40–7.20 (m, 2H), 4.57 (s, 2H), 3.90–3.70 (m, 4H), 3.35–3.20 (m, 4H).

MS (m/e): 322 (M$^+$+1), 294 (—N$_2$), 251.

EXAMPLE 12

4-[4-(4-Azidomethyl-[1,2,3]triazol-1-yl)-2-fluorophenyl]-morpholine

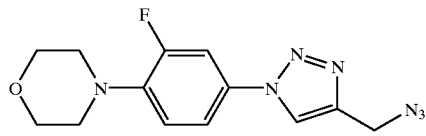

The title compound (0.54 g, 82%) was obtained from methanesulfonic acid 1-(3-fluoro-4-morpholin-4-yl-phenyl)-1H-[1,2,3]triazol-4-ylmethyl ester (0.8 g, 2.16 mmol), as reported in Example 8, by a procedure as described in Example 11. Mp. 90° C.

$^1$H NMR (CDCl$_3$): δ 7.90 (s, 1H), 7.60–7.40 (m, 2H), 7.10 (t, J=8.8 Hz, 1H), 4.50 (s, 2H), 4.02–3.80 (m, 4H), 3.20–3.10 (m, 4H).

MS (m/e): 304 (M$^+$+1), 278 (—N$_2$).

EXAMPLE 13

4-[4-(4-Azidomethyl-[1,2,3]triazol-1-yl)-2,6-difluorophenyl[thiomorpboline (13A) & 4-[4-(5-Azidomethyl-[1,2,3]triazol-1-yl)-2,6-difluorophenyl]thiomorpholine (13B)

13A
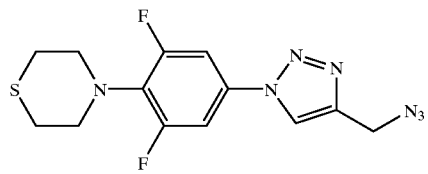

13B
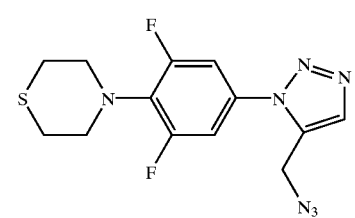

Sodium azide (1.10 g, 16.90 mmol) was added to the mixture of methanesulfonic acid 1-(3,5-difluoro-4-thiomorpholin-4-yl-phenyl)-1H-[1,2,3]triazol-4-ylmethyl ester and methanesulfonic acid 3-(3,5-(difluoro-4-thiomorpholin-4-yl-phenyl)-3H-[1,2,3]triazol-5-ylmethyl ester, obtained in Example 9, in DMF (10 mL) and heated to 90° C. for 1 h. The reaction mixture was cooled to room temperature and diluted with ethyl acetate (200 mL). The solution was washed with water (100 mL×2) followed by brine (50 mL) and dried over sodium sulfate. Removal of volatiles and purification of the residual material by silica gel column chromatography (eluent, 1:9–3:7 ethyl acetate/hexane) yielded compounds 1-[3,5-difluoro-4-(4-thiomorpholinyl)phenyl]-1H-1,2,3-triazol-4-ylmethyl azide (13A) (800 mg, 45%) followed by 1-[3,5-difluoro-4-(4-thiomorpholinyl)phenyl]-1H-1,2,3-triazol-5-ylmethyl azide (13B) (850 mg, 50%).

Compound (13A):

$^1$H NMR (CDCl$_3$): δ 7.88 (s, 1H), 7.40–7.20 (m, 2H), 4.50 (s, 2H), 3.50–3.30 (m, 4H), 2.90–2.70 (m, 4H).

MS (m/e): 338 (M$^+$+1), 310 (—N$_2$), 267.

EXAMPLE 14

4-[4-(4-Azidomethyl-[1,2,3]triazol-1-yl)-2-fluoro-phenyl]thiomorpholine (14A) & 4-[4-(5-Azidomethyl-[1,2,3]triazol-1-yl)-2-fluoro-phenyl]thiomorpholine (14B)

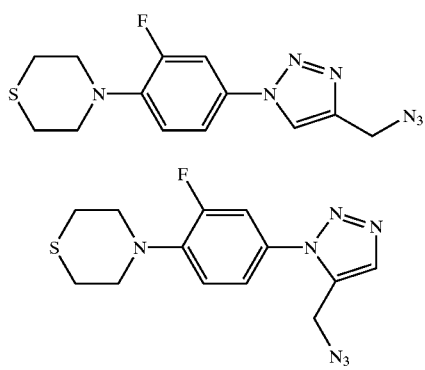

The title azides, 1-[3-fluoro-4-(4-thiomorpholinyl)phenyl]-1H-1,2,3-triazol-4-ylmethyl azide (14A) (800 mg, 45%) and 1-[3-fluoro-4-(4-thiomorpholinyl)phenyl]-1H-1,2,3-triazol-5-ylmethyl azide (14B) (850 mg, 50%), were obtained from a mixture of mesylates (2.2 g), as reported in Example 10, by a procedure as described in Example 13.

Compound (14A):

$^1$H NMR (CDCl$_3$): δ 7.90 (s, 1H), 7.60–7.40 (m, 2H), 7.10 (t, J=8.6 Hz, 1H), 4.50 (s, 2H), 3.50–3.30 (m, 4H), 2.90–2.70 (m, 4H).

MS (m/e): 320 (M$^+$+1), 292 (—N$_2$), 249.

EXAMPLE 15

C-[1-(3,5-Difluoro-4-morpholin-4-yl-phenyl)-1H-[1,2,3]triazol-4-yl]-methylamine

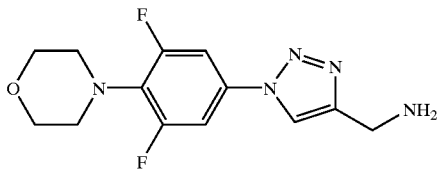

A solution of 4-[4-(4-azidomethyl-[1,2,3]triazol-1-yl)-2,6-di fluorophenyl]-morpholine (0.5 g, 1.55 mmol), obtained in Example 11, and triphenylphosphine (0.45 g, 1.71 mmol) in THF (25 mL) was stirred at room temperature for 4 h. It was then warmed to 40° C. after the addition of 2 mL of water and allowed to stir at the same temperature for 16 h. The reaction mixture was diluted with water and extracted with ethyl acetate (30 mL×2). The combined ethyl acetate extract was washed with water followed by brine and dried over sodium sulfate. Evaporation of volatiles and purification of the resulting residue by silica gel column chromatography (CHCl$_3$/MeOH, 9:1) yielded the title compound as pale yellow crystals (0.3 g, 66%).

$^1$H NMR (CDCl$_3$): δ 7.94 (s, 1H), 7.40–7.20 (m, 2H), 4.77 (s, 2H), 3.90–3.70 (m, 4H), 3.30–3.10 (m, 4H).

MS (m/e): 296 (M$^+$+1), 251, 238.

EXAMPLE 16

2-[1-(3-Fluoro-4-morpholin-4-yl-phenyl)-1H-[1,2,3]triazol-4-ylmethyl]-isoindole-1,3-dione

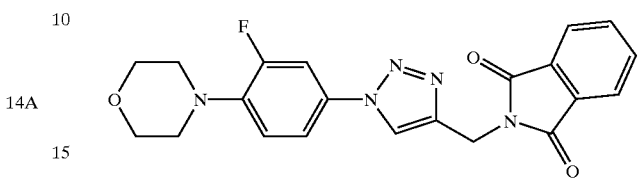

To a stirring solution of 4-(4-azido-2-fluorophenyl)morpholine (1 g, 4.6 mmol), as reported in Preparation 12, in acetonitrile (20 mL) was added 2-(2-propynyl)-isoindolene-1,3-dione (0.85 g, 4.6 mmol) followed by N-ethyldiisopropyl amine (10 mL). Cuprous iodide (0.87 g, 4.6 mmol) was then added to the reaction mixture in portion while the title compound started precipitating out. The precipitation was completed within 10 min. and it was allowed to stir for additional 10 min. The precipitate was collected on a buchner funnel and washed with acetonitrile (2 mL). The light yellow compound (1.54 g, 85%) was obtained.

$^1$H NMR (CDCl$_3$): δ 8.72 (s, 1H), 7.98–7.82 (m, 4H), 7.79–7.58 (m, 2H), 7.17 (t, J=8.9 Hz, 1H), 4.93 (s, 2H), 3.76 (br s, 4H), 3.07 (br s, 4H).

MS (m/e): 408 (M$^+$+1), 379, 130.

EXAMPLE 17

C-[1-(3-Fluoro-4-morpholin-4-yl-phenyl)-1H-[1,2,3]triazol4-yl]-methylamine

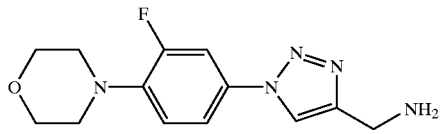

To a stirring solution of 2-[1-(3-fluoro-4-morpholin-4-yl-phenyl)-1H-[1,2,3]triazol-4-ylmethyl]-isoindole-1,3-dione (1.0 g, 2.46 mmol), obtained in the Example 16, in methanol (10 mL) was added hydrazine hydrate (7.4 mL, 14.3 mmol) and refluxed for 8 h. The reaction mixture was allowed to stand at room temperature overnight. The precipitate formed was filtered off and the filtrate was concentrated. Title amine (440 mg, 65%) was obtained after purification by silica gel column chromatography.

$^1$H NMR (CDCl$_3$): δ 7.82 (s, 1H), 7.60–7.40 (m, 2H), 7.10–6.95 (t, J=8.7 Hz, 1H), 4.07 (s, 2H), 4.01–3.80 (m, 4H), 3.30–3.10 (m, 4H).

MS (m/e): 278 (M$^+$+1). OR

Alternatively, the title compound (0.36 g, 80%) was obtained from 4-[4-(4-azidomethyl-[1,2,3]triazol-1-yl)-2-fluorophenyl]-morpholine (0.5 g, 1.65 mmol), as reported in Example 12, and triphenylphosphine (0.53 g, 1.82 mmol) by a procedure as described in Example 15.

EXAMPLE 18

C-[1-(3,5-Difluoro-4-thiomorpholin-4-yl-phenyl)-1H-1,2,3]triazol4-yl]-methylamine

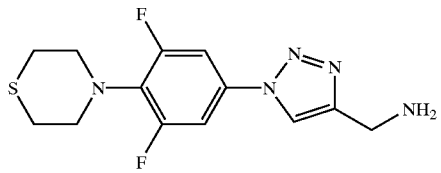

The title compound (0.33 g, 70%) was obtained from 4-[4-(4-azidomethyl-[1,2,3]triazol-1-yl)-2,6-difluorophenyl]-triomorpholine (0.53 g, 1.55 mmol), as reported in Example 13, and triphenylphosphine (0.45 g, 1.71 mmol) by a procedure as described in Example 15.

$^1$H NMR (CDCl$_3$): δ 7.95 (s, 1H), 7.40–7.20 (m, 2H), 4.80 (s, 2H), 3.55–3.35 (m, 4H), 2.90–2.70 (m, 4H).

MS (m/e): 312 (M$^+$+1), 267, 254.

EXAMPLE 19

C-[1-(3-Fluoro-4-thiomorpholin-4-yl-phenyl)-1H-[1,2,3]triazol-4-yl]-methylamine

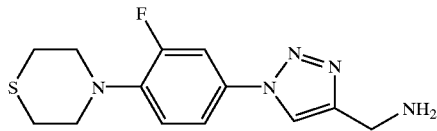

The title compound (0.7 g, 76%) was obtained from 4-[4-(4-azidomethyl-[1,2,3]triazol-1-yl)-2-fluorophenyl]thiomorpholine (0.8 g, 2.5 mmol), as reported in Example 14, and triphenylphosphine (0.8 g, 2.76 mmol) by a procedure as described in Example 15.

$^1$H NMR (CDCl$_3$): δ 7.83 (s, 1H), 7.55–7.35 (m, 2H), 7.10–6.95 (t, J=8.8 Hz, 1H), 4.08 (s, 2H), 3.50–3.30 (m, 4H), 2.90–2.70 (m, 4H).

MS (m/e): 294 (M$^+$+1).

EXAMPLE 20

4-[4-(4-Azidomethyl-[1,2,3]triazol-1-yl)-2,6-difluorophenyl]-thiomorpholine-1-oxide

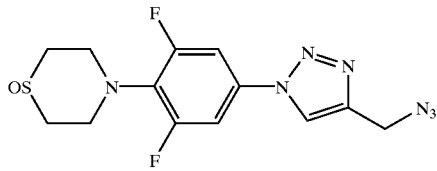

m-Chloroperoxybenzoic acid (75%, 545 mg, 2.36 mmol) was added to a solution of 4-[4-(4-azidomethyl-[1,2,3]triazol-1-yl)-2,6-difluoro-phenyl]-thiomorpholine (800 mg mmol), obtained in Example 13, in dichloromethane (10 mL) at 0° C. and allowed to stir for 1 h. The reaction mixture was then diluted with dichloromethane (20 mL) and a solution of sodium sulfite was added. Aqueous layer was separated and the dichloromethane layer was washed with water followed by brine and dried over sodium sulfate. Removal of volatiles produced the title sulfoxide (800 mg, 95%).

$^1$H NMR (CDCl$_3$): δ 7.90 (s, 1H), 7.40–7.20 (m, 2H), 4.60 (s, 2H), 4,20–4.00 (m, 2H), 3.40–3.20 (m, 2H), 3.10–2.90 (m, 4H).

MS (m/e): 354 (M$^+$+1).

EXAMPLE 21

4-[4-(4-Azidomethyl-[1,2,3]triazol-1-yl)-2,6-difluorophenyl]-thiomorpholine-1,1-dioxide

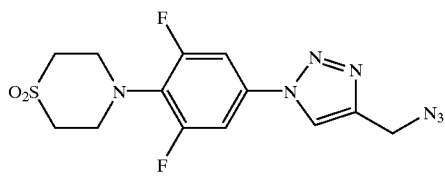

The title compound (810 mg, 92%) was obtained from 4-[4-(4-azidomethyl-[1,2,3]triazol-1-yl)-2,6-difuorophenyl]thiomorpholine (800 mg, 2.36 mmol), as reported in Example 13, and m-chloroperoxybenzoic acid (75%, 1.1 g, 4.72 mmol) by a procedure as described in Example 20.

$^1$H NMR (CDCl$_3$): δ 7.93 (s, 1H), 7.50–7.02 (m, 2H), 4.60 (s, 2H), 3.80–3.60 (m, 4H), 3.30–3.10 (m, 4H).

MS (m/e): 370 (M$^+$+1), 342, 299, 157.

EXAMPLE 22

4-[4-(4-Azidomethyl-[1,2,3]triazol-1-yl)-2-fluorophenyl]-thiomorpholine 1-oxide

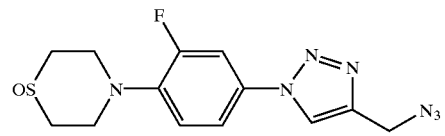

The title compound (800 mg, 95%) was obtained from 4-[4-(4-azidomethyl-[1,2,3]triazol-1-yl)-2-fluorophenyl]thiomorpholine (800 mg, 2.5 mmol), as reported in Example 14, and m-chloroperoxybenzoic acid (75%, 591 g, 2.5 mmol) by a procedure as described in Example 20.

$^1$H NMR (CDCl$_3$): δ 7.96 (s, 1H), 7.60–7.40 (m, 2H), 7.30–7.10 (t, J=8.8 Hz, 1H), 4.60 (s, 2H), 4.00–3.80 (m, 2H), 3.50–3.30 (m, 2H), 3.10–2.90 (m, 4H).

MS (m/e): 336 (M$^+$+1), 265, 175.

EXAMPLE 23

4-[4-(4-Azidomethyl-[1,2,3]triazol-1-yl)-2-fluorophenyl]-thiomorpholinie-1,1-dioxide

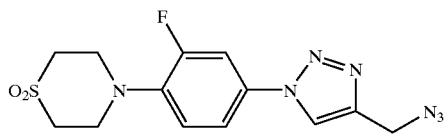

The title compound (192 mg, 90%) was obtained from 4-[4-(4-azidomethyl-[1,2,3]triazol-1-yl)-2-fluoro-phenyl]-thiomorpholine (800 mg, 2.5 mmol), as reported in Example 14, and m-chloroperoxybenzoic acid (75%, 1.2 g, 5.0 mmol) by a procedure as described in Example 20.

$^1$H NMR (CDCl$_3$): δ 7.90 (s, 1H), 7.50–7.40 (m, 2H), 7.10 (t, J=8.8 Hz, 1H), 4.60 (s, 2H), 3.80–3.60 (m, 4H), 3.40–3.20 (m, 4H).

MS (m/e): 352 (M$^+$+1), 281, 157.

EXAMPLE 24

1-[4-(4-Azidomethyl-[1,2,3]triazol-1-yl)-2-fluoro-phenyl]-piperidin-4-one & 1-[4-(5-Azidomethyl-[1,2,3]triazol-1-yl)-2-fluoro-phenyl]-piperidin-4-one

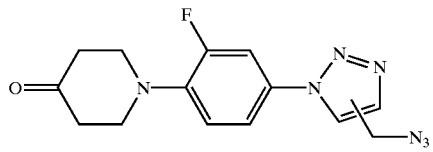

To a solution of 1-[2-Fluoro-4-(4-hydroxymethyl-[1,2,3]triazol-1-yl)-phenyl]-piperidin-4-one and 1-[2-Fluoro-4-(5-hydroxymethyl-[1,2,3]triazol-1-yl)-phenyl]-piperidin-4-one, (10 gm, 34 mmol), obtained in example 6, in dichloromethane (300 ml) was added triethylamine (7 g, 69 mmol) followed by the addition of methanesulfonyl chloride (5.8 g, 52 mmol) at 0° C. and stirred for 1 h. The reaction mixture was then washed with water followed by brine and dried over sodium sulfate. Evaporation of dichloromethane left a pasty mass that was dissolved in DMF (50 ml). The solution thus obtained was heated to 90° C. along with sodium azide (4.2 g, 65 mmol) for 2 h. It was then poured into ice-water and extracted with ethyl acetate (100 ml×2). Combined organic portion was washed with water and dried over sodium sulfate. Removal of volatiles gave a mixture of title azides (6 g).

MS (m/e): 316 (M$^+$+1), 315, 288, 245.

EXAMPLE 25

8-[4-(4-Azidomethyl-[1,2,3]triazol-1-yl)-2-fluoro-phenyl]-1,4-dioxa-8-aza-spiro[4.5]decane

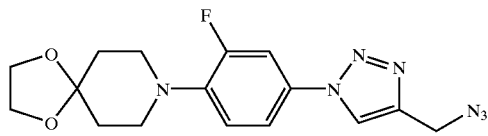

A solution of ethylene glycol (0.147 g, 2.38 mmol) and 1-[4-(4-Azidomethyl-[1,2,3]triazol-1-yl)-2-fluoro-phenyl]-piperidin-4-one and 1-[4-(5-Azidomethyl-[1,2,3]triazol-1-yl)-2-fluoro-phenyl]-piperidin-4-one (0.5 g, 1.58 mmol), obtained in example 24, in toluene (20 ml) was refluxed along with catalytic amount of p-toluenesulphoric acid using Dean-Stark apparatus for 3 h. The reaction mixture was then diluted with ethyl acetate (50 ml) and the organic portion was washed with water followed by brine and dried over sodium sulfate. Upon concentration a residue was obtained, which was purified by column chromatography (ethyl acetate/pet. ether, 1:1) to obtain isomerically pure title compound (0.1 g, 1 8%).

$^1$H NMR (CDCl$_3$): δ 7.92 (s, 1H), 7.49–7.41 (m, 3H), 4.60 (s, 2H), 4.02 (s, 4H), 3.30 (t, J=5.3 Hz, 4H), 1.96 (t, J=5.3 Hz, 4H).

MS (m/e): 360 (M$^+$+1), 334, 332, 311, 289, 257, 195.

EXAMPLE 26

4-[4-(4-Azidomethyl-[1,2,3]triazol-1-yl)-2-fluoro-phenyl]-1lambda*4*-thiomorpholin-1-ylideneamine

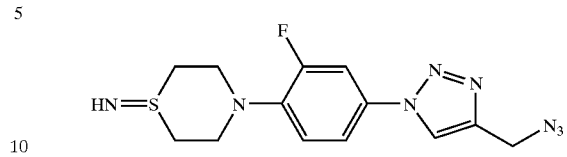

To a stirring solution of 4-[4-(4-azidomethyl-[1,2,3]triazol-1-yl)-2-fluoro-phenyl]-thiomorpholine (1 g, 3.13 mmol), obtained in Example 14 and sodium azide (0.3 g, 4.7 mmol) in chloroform (50 ml) was added conc. H$_2$SO$_4$ (2 ml) and warmed to 50° C. for 20 h. The reaction mixture was then poured into ice-water and basified with NaHCO$_3$ to neutral pH. Aqueous layer was extracted with ethyl acetate (100 ml×2) and the organic portion was dried over sodium sulfate. Removal of volatiles yielded the title compound (450 mg, 43%).

$^1$H NMR (CDCl$_3$): δ 7.89 (s, 1H), 7.58–7.40 (m, 2H), 7.21 (t, J=8.6 Hz, 1H), 4.60 (s, 2H), 4.01–3.80 (m, 2H), 3.49–3.30 (m, 2H), 3.11–2.88 (m, 4H).

MS (m/e): 335 (M$^+$+1), 307 (—N$_2$), 291, 244, 217, 188, 161.

EXAMPLE 27

C-{1-[3-Fluoro-4-(1-oxo-1lambda*4*-thiomorpholin-4-yl)-phenyl]-1H-[1,2,3]triazol-4-yl}-methylamine

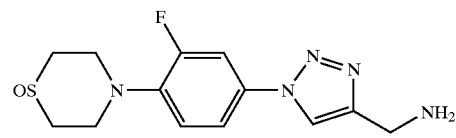

The title compound (510 mg, 70%) was obtained from 4-[4-(4-azidomethyl-[1,2,3]triazol-1-yl)-2-fluorophenyl]-thiomorpholine 1-oxide (0.8 g, 2.38 mmol), as reported in Example 22, and triphenylphosphine (0.76 mg, 2.62 mmol), by a procedure as described in Example 15.

$^1$H NMR (CDCl$_3$): δ 8.60 (s, 1H), 7.95–7.60 (m, 2H), 7.36 (t, J=8.8 Hz, 1H), 3.85 (s, 2H), 3.60–3.50 (m, 2H), 3.40–2.80 (m, 6H).

MS (m/e): 310 (M$^+$+1), 264, 218.

EXAMPLE 28

C-{1-[3,5-Difluoro-4-(1-oxo-1lambda*4*-thiomorpholin-4-yl)-phenyl]-1H-[1,2,3]triazol-4-yl}-methylamine

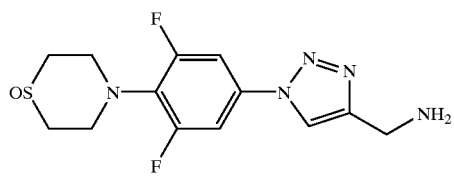

The title compound (555 mg, 75%) was obtained from 4-[4-(4-azidomethyl-[1,2,3]triazol-1-yl)-2,6- difluorophenyl)-thiomorpholine-1-oxide (800 mg, 2.26 mmol), as reported in Example 20, and triphenylpliosphine (653 mg, 2.49 mmol) by a procedure as described in Example 15. Mp. 190° C.

¹H NMR (CDCl₃+DMSO-d₆): δ 8.35 (s, 1H), 7.60–7.40 (m, 2H), 4.03 (s, 2H), 3.40–3.20 (m, 4H), 3.10–2.90 (m, 4H).

MS (m/e): 328 (M⁺+1), 283, 208.

EXAMPLE 29

C-{1-[4-(1,1-Dioxo-1lambda*6*-thiomorpholin-4-yl)-3,5-difluoro-phenyl]-1H-[1,2,3]triazol-4-yl}-methylamine

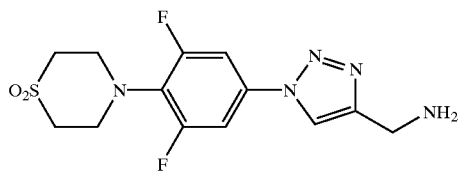

The title compound (499 mg, 67%) was obtained from 4-[4-(4-azidomethyl-[1,2,3]triazol-1-yl)-2,6-difluorophenyl]-thiomorpholine-1,1-dioxide (800 mg, 2.17 mmol), as reported in Example 21, and triphenylphosphinc (0.7 g, 2.39 mmol) by a procedure as described in Example 15.

¹H NMR (CDCl₃+DMSO-d₆): δ 7.87 (s, 1H), 7.70–7.50 (m, 2H), 4.04 (s, 2H), 3.80–3.60 (br. s, 4H), 3.40–3.20 (m, 4H).

MS (m/e): 344 (M⁺+1), 299, 286, 279.

EXAMPLE 30

C-{1-[4-(1,1-Dioxo-1lambda*6*-thiomorpholin-4-yl)-3-fluoro-phenyl]-1H-[1,2,3]triazol-4-yl}-methylamine

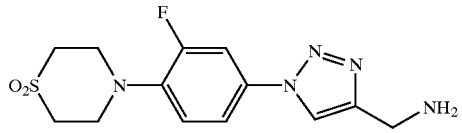

The title compound (476 mg, 67%) was obtained from 4-[4-(4-azidomethyl-[1,2,3]triazol-1-yl)-2-fluorophenyl]-thiomorpholine-1,1-dioxide (800 mg, 2.28 mmol), as reported in Example 23, and triphenylphosphine (0.73 g, 2.5 mmol) by a procedure as described in Example 15.

¹H NMR (CDCl₃+DMSO-d₆): δ 8.40 (s, 1H), 7.75–7.50 (m, 2H), 7.20 (t, J=8.8 Hz, 1H), 4.00 (br s, 2H), 3.61 (br s, 4H), 3.50–3.10 (m, 4H).

MS (m/e): 326 (M⁺+1), 297, 281, 268.

EXAMPLE 31

C-{1-[4-(1,4-Dioxa-8-aza-spiro[4.5]dec-8-yl)-3-fluoro-phenyl]-1H-1,2,3]triazol-4-yl}-methylamine

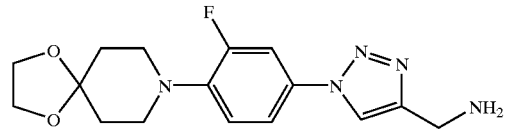

A solution of 8-[4-(4-azidomethyl-[1,2,3]triazol-1-yl)-2-fluoro-phenyl]-1,4-dioxa-8-aza-spiro[4.5]decane (2 g, 5.57 mmol), obtained in Example 25, and triphenylphosphine (1.6 g, 6.12 mmol) in THF (50 ml) was stirred at room temperature for 4 h. The reaction mixture was then warmed to 40° C. after the addition of 2 ml of water and allowed to stir at the same temperature for 16 h. The reaction mixture was diluted with water and extracted with ethyl acetate (100 ml×2). Combined ethyl acetate extract was washed with water followed by brine and dried over sodium sulfate. Evaporation of volatiles and purification of the resulting residue by silica gel column chromatography (MeOH/CHCl₃, 1:16) yielded the title amine (1.5 g, 83%).

¹H NMR (CDCl₃): δ 8.62 (s, 1H), 7.79–7.61 (m, 2H), 7.20 (t, J=8.6 Hz, 1H), 3.90 (s, 4H), 3.81 (s, 2H), 3.19 (br s, 4H), 1.80 (br s, 4H).

MS (m/e): 334(M⁺+1), 332, 305, 289, 276, 232, 163.

EXAMPLE 32

4-[4-(4-Aminomethvl-[1,2,3]triazol-1-yl)-2-fluoro-phenyl]-1-imino-1lambda*4*-thiomorpholine

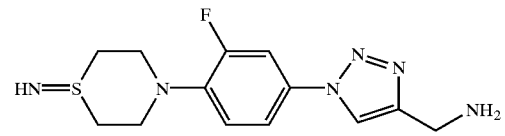

A solution of the 4-[4-(4-azidomethyl-[1,2,3]triazol-1-yl)-2-fluoro-phenyl]-1lambda*4*-thiomorpholin-1-ylideneamine (0.45 g, 1.35 mmol), obtained in Example 26, and triphenylphosphine (0.39 g, 1.48 mmol) in THF (10 ml) were stirred at room temperature for 4 h. It was then warmed to 40° C. after the addition of 2 ml of water and allowed to stir at the same temperature for 16 h. The reaction mixture was then diluted with water and extracted with ethyl acetate (30 ml×2). Combined ethyl acetate extract was washed with water followed by brine and dried over sodium sulfate. Evaporation of volatiles and purification of the resulting residue by silica gel column chromatography (MeOH/CHCl₃, 3:7) yielded the title amine (0.28 g, 66%).

¹H NMR (CDCl₃): δ 8.60 (s, 1H), 7.79–7.60 (m, 2H), 7.35 (t, J=9.1 Hz, 1H), 3.88 (s, 2H), 3.70–3.49 (m, 2H), 3.40–3.20 (m, 2H), 3.18–2.78 (m, 4H).

MS (m/e): 310 (M⁺+2), 295, 264.

EXAMPLE 33

4-[2,6-Difluoro-4-(4-isothiocyanatomethyl-[1,2,3]triazol-1-yl)-phenyl]-morpholine

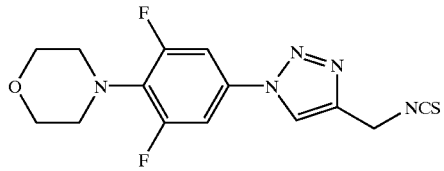

To a suspension of satd. NaHCO$_3$ solution (10 mL) and C-[1-(3,5-difluoro-4-morpholin-4-yl-phenyl)-1H-[1,2,3]triazol-4-yl]-methylamine (0.2 g, 0.68 mmol), obtained in Example 15, in chloroform (10 mL) was added thiophosgene (62 μL 0.74 mmol) and stirred for 30 min. The reaction mixture was then diluted with chloroform (20 mL) and the chloroform portion was washed with water followed by brine and dried over sodium sulfate. Upon concentration the title compound was obtained as light brown solid (0.2 g, 70%).

EXAMPLE 34

4-[2-Fluoro-4-(4-isothiocyanatomethyl-[1,2,3]triazol-1-yl)-phenyl]-morpholine

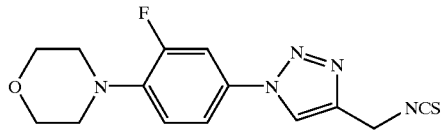

The title compound (0.16 g, 70%) was obtained from C-[1-(3-fluoro-4-morpholin-4-yl-phenyl)-1H-[1,2,3]triazol-4-yl]-methylamine (0.2 g, 0.72 mmol), as reported in Example 17, and thiophosgene (66 μL 0.79 mmol) by a procedure as described in Example 33.

EXAMPLE 35

4-[2,6-Difluoro-4-(4-isothiocyanatomethyl-[1,2,3]triazol-1-yl)-phenyl]-thiomorpholine

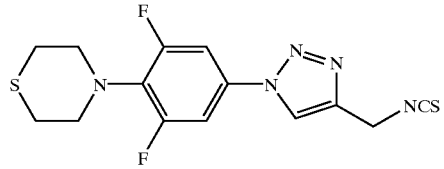

The title compound (0.21 g, 70%) was obtained from C-[1-(3,5-difluoro-4-thiomorpholin-4-yl-phenyl)-1H-[1,2,3]triazol-4-yl]-methylamine (0.22 g, 0.68 mmol), as reported in Example 18, and thiophosgene (62 μL 0.74 mmol) by a procedure as described in Example 33.

EXAMPLE 36

4-[2-Fluoro-4-(4-isothiocyanatomethyl-[1,2,3]triazol-1-yl)-phenyl]-thiomorpholine

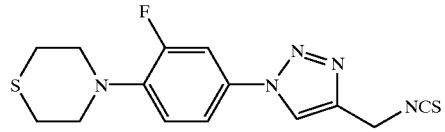

The title compound (0.175 g, 75%) was obtained from C-[1-(3-fluoro-4-thiomorpholin-4-yl-phenyl)-1H-[1,2,3]triazol-4-yl]-methylamine (0.2 g, 0.68 mmol), as reported in Example 19, and thiophosgene (62 μL, 0.74 mmol) by a procedure as described in Example 33.

EXAMPLE 37

4-[2-Fluoro-4-(4-isothiocyanatomethyl-[1,2,3]triazol-1-yl)-phenyl]-thiomorpholine1-oxide

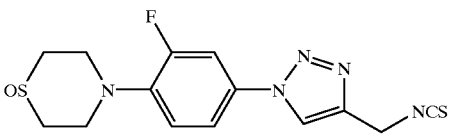

The title compound (0.48 g, 85%) was obtained from C-{1-[3-fluoro-4-(1-oxo-1lambda*4*-thiomorpholin-4-yl)-phenyl]-1H-[1,2,3]triazol-4-yl}-methylamine (500 mg), as reported in Example 27, and thiophosgene (137 μL 1.8 mmol) by a procedure as described in Example 33.

EXAMPLE 38

4-[2,6-Difluoro-4-(4-isothiocyanatomethyl-[1,2,3]triazol-1-yl)-phenyl]-thiomorpholine 1-oxide

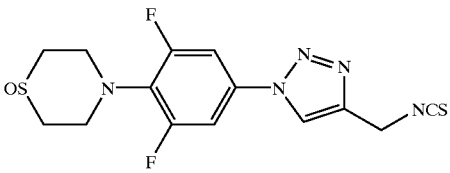

The title compound (0.48 g, 85%) was obtained from C-{1-[3,5-difluoro-4-(1-oxo-1lambda*4*-thiomorpholin-4-yl)-phenyl]-1H-[1,2,3]triazol-4-yl }-methylamine (500 mg, 1.5 mmol), as reported in Example 28, and thiophosgene (128 μL 1.55 mmol) by a procedure as described in Example 33.

$^1$H NMR (CDCl$_3$): δ 8.01 (s, 1H), 7.40–7.20 (m, 2H), 4.90 (s, 2H), 4.20–4.00 (m, 2H), 3.40–3.20 (m, 2H), 3.10–2.90 (m, 4H).

MS (m/e): 370 (M$^+$+1), 352, 283, 193.

EXAMPLE 39

4-[2,6-Difluoro-4-(4-isotbiocyanatomethyl-[1,2,3]triazol-1-yl)-phenyl]-thiomorpholine 1,1-dioxide

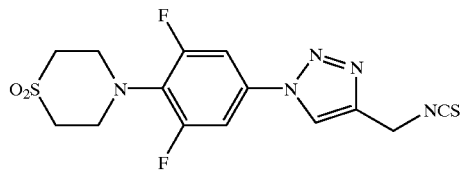

The title compound (0.27 g, 80%) was obtained from C-{1-[4-(1,1-dioxo-1lambda*6*-thiomorpholin-4-yl)-3,5-difluoro-phenyl]-1H-[1,2,3]triazol-4-yl}-methylamine (0.3 g, 0.874 mmol), as reported in Example 29, and thiophosgene (79 μL 0.96 mmol) by a procedure as described in Example 33.

$^1$H NMR (CDCl$_3$): δ 8.00 (s, 1H), 7.50–7.30 (m, 2H), 4.95 (s, 2H), 3.80–3.60 (br s, 4H), 3.30–3.10 (m, 4H).

MS (m/e): 386 (M$^+$+1), 319, 299, 279, 201.

EXAMPLE 40

4-[2-Fluoro-4-(4-isothiocyanatomethyl-[1,2,3]triazol-1-yl)-phenyl]-thiomorpholine 1,1-dioxide

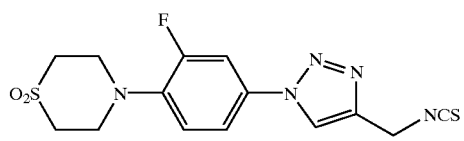

The title compound (0.271 g, 80%) was obtained from C-{1-[4-(1,1-dioxo-1lambda*6*-thiomorpholin-4-yl)-3-fluoro-phenyl]-1H-[1,2,3]triazol-4-yl}-metlylamine (0.3 g, 0.923 mmol), as reported in Example 30, and thiophosgene (84 μL 1.02 mmol) by a procedure as described in Example 33.

EXAMPLE 41

N-[1-(3,5-Difluoro-4-morpholin-4-yk-phenyl)-1H-[1,2,3]triazol-4-ylmethyl]-acetamid

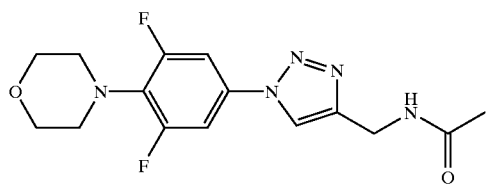

A solution of 4-[4-(4-azidomethyl-[1,2,3]triazol-1-yl)-2,6-difluoro-phenyl]-morpholine (0.3 g, 0.93 mmol), obtained in Example 11, in thiolaceticacid (3 mL) was stirred at room temperature for 15 h. The reaction mixture was adsorbed on silica gel and purified by column chromatography with ethyl acetate as eluent to produce the title compound as crystalline white solid (0.28 g, 80%). Mp. 218° C.

$^1$H NMR (CDCl$_3$): δ 7.93 (s, 1H), 7.30–7.20 (m, 2H), 6.26 (br s, 1H), 4.56 (d, J=5.9 Hz, 2H), 3.90–3.80 (m, 4H), 3.35–3.20 (m, 4H), 2.02 (s, 3H).

MS (m/e): 338 (M$^+$+1), 309, 266, 213.

EXAMPLE 42

N-[1-(3-Fluoro-4-morpholin-4-yl-phenyl)-1H-[1,2,3]triazol-4-ylmethyl]-acetamide

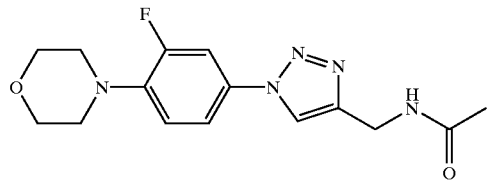

The title compound (0.47 g, 75%) was obtained from 4-[4-(4-azidomethyl-[1,2,3]triazol-1-yl)-2-fluoro-phenyl]-morpholine (0.6 g, 1.98 mmol), as reported in Example 12, by a procedure as described in Example 41. Mp. 218° C.

$^1$H NMR (CDCl$_3$+DMSO-d$_6$): δ 8.05 (s, 1H), 7.80 (br s, 1H), 7.60–7.40 (m, 2H), 7.05 (t, J=8.8 Hz, 1H), 4.52 (d, J=5.9 Hz, 2H), 3.95–3.80 (m, 4H), 3.30–3.10 (m, 4H), 2.01 (s, 3H).

MS (m/e): 320 (M$^+$+1), 291.

EXAMPLE 43

N-[1-(3,5-Difluoro-4-thiioniorpholin-4-yl-phenyl)-1H-[1,2,3]triazol-4-ylmethyl]-acetamide

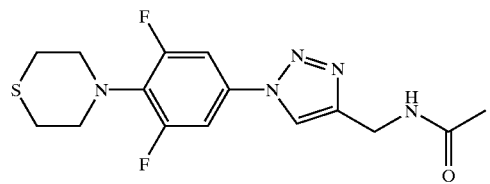

The title compound (0.29 g, 80%) was obtained from 4-[4-(4-azidomethyl-[[1,2,3]triazol-1-yl)-2,6-difluoro-phenyl]-thiomorpholine (0.32 g, 0.93 mmol), as reported in Example 13, by a procedure as described in Example 41. Mp. 210° C.

$^1$H NMR (CDCl$_3$): δ 7.94 (s, 1H), 7.30–7.20 (m, 2H), 6.90 (br s, 1H), 4.54 (d, J=5.6 Hz, 2H), 3.50–3.53 (m, 4H), 2.90–2.70 (m, 4H), 2.01 (s, 3H).

MS (m/e): 354 (M$^+$+1), 325, 229.

EXAMPLE 44

N-{1-[3,5-Difluoro-4-(1-oxo-1lambda*4*-thiomorpholin-4-yl)-phenyl]-1H-[1,2,3]triazol-4-ylmethyl}-acetamide

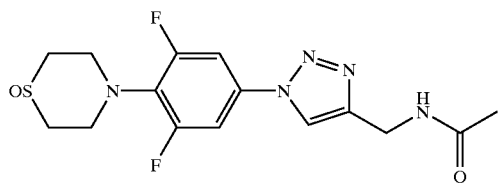

The title compound (0.146 g, 70%) was obtained from 4-[4-(4-azidomethyl-[1,2,3]triazol-1-yl)-2,6-difluoro-phenyl]-thiomorpholine 1-oxide (0.2 g, 0.56 mmol), as reported in Example 20, by a procedure as described in Example 41. Mp. 203° C.

¹H NMR (CDCl₃): δ 7.97 (s, 1H), 7.60–7.40 (m, 2H), 6.50 (br s, 1H), 4.57 (d, J=5.9 Hz, 2H), 3.95–3.75 (m, 2H), 3.50–3.30 (m, 2H), 3.10–2.90 (m, 4H), 2.03 (s, 3H).

MS (m/e): 370 (M⁺+1).

EXAMPLE 45

N-{1-[4-(1,1-Dioxo-1lambda*6*-thiomorpholin-4-yl)-3,5-difluoro-phenyl]-1H-[1,2,3]triazol-4-ylmethyl}-acetamide

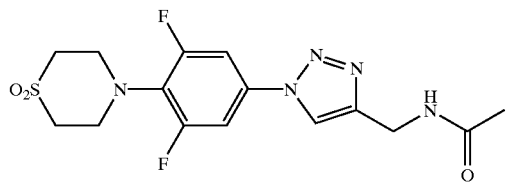

The title compound (0.146 g, 70%) was obtained from 4-[4-(4-azidomethyl-[1,2,3]triazol-1-yl)-2,6-difluoro-phenyl]-thiomorpholine 1,1-dioxide (0.2 g, 0.542 mmol), as reported in Example 21, by a procedure as described in Example 41. Mp. 197° C.

¹H NMR (CDCl₃): δ 8.01 (s, 1H), 7.60–7.50 (m, 2H), 6.52 (br s, 1H), 4.58 (d, J=5.9 Hz, 2H), 3.90–3.70 (m, 4H), 3.30–3.10 (m, 4H), 2.05 (s, 3H).

MS (m/e): 386 (M⁺+1).

EXAMPLE 46

N-[1-(3-Fluoro-4-thiomorpholin-4-yl-phenyl)-1H-[1,2,3]triazol-4-ylmethyl]-acetamide

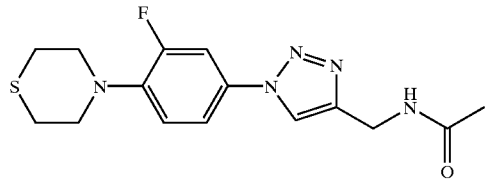

The title compound (0.163 g, 78%) was obtained from 4-[4-(4-azidomethyl-[1,2,3]triazol-1-yl)-2-fluoro-phenyl]-thiomorpholine (0.2 g, 0.626 mmol), as reported in Example 14, by a procedure as described in Example 41. Mp. 207° C.

¹H NMR (CDCl₃): δ 8.20 (s, 1H), 7.60–7.40 (m, 2H), 7.15 (t, J=8.8 Hz, 1H), 4.57 (d, J=5.9 Hz, 2H), 3.90–3.70 (m, 2H), 3.30–3.10 (m, 2H), 2.90–2.70 (m, 2H), 2.01 (s, 3H).

MS (m/e): 336 (M⁺+1).

EXAMPLE 47

N-{1-[3-Fluoro-4-(1-oxo-1lambda*4*-thiomorpholin-4-yl)-phenyl]-1H-[1,2,3]triazol-4-ylmethyl}-acetamide

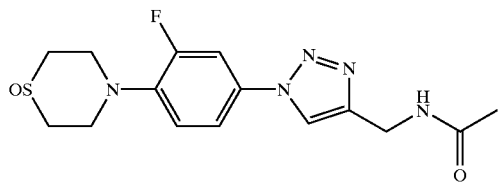

The title compound (0.252 g, 80%) was obtained from 4-[4-(4-azidomethyl-[1,2,3]triazol-1-yl)-2-fluoro-phenyl]-thiomorpholine 1-oxide (0.3 g, 0.89 mmol), as reported in Example 22, by a procedure as described in Example 41. Mp. 210° C.

¹H NMR (CDCl₃): δ 7.97 (s, 1H), 7.60–7.40 (m, 2H), 7.20–7.10 (t, J=8.6 Hz, 1H), 6.60–6.40 (br s, 1H), 4.57 (d, J=5.9 Hz, 2H), 3.90–3.70 (m, 2H), 3.50–3.30 (m, 2H), 3.10–2.90 (m, 4H), 2.03 (s, 3H).

MS (m/e): 352 (M⁺+1), 336, 306, 264.

EXAMPLE 48

{1-[3-Fluoro-4-(1-oxo-1lamhda*4*-thiomorpholin-4-yl)-phenyl]-1H-[1,2,3]triazol-4-ylmethyl}-carbamic acid methyl ester

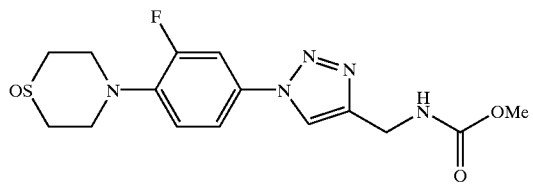

To a stirring solution of C-{1-[3-fluoro-4-(1-oxo-1lambda*4*-thiomorpholin-4-yl)-phenyl]-1H-[1,2,3]triazol-4-yl}-methylamine (300 mg, 0.97 mmol), obtained in Example 27, in dichloroinethane (15 mL) was added N-ethyl diisopropylamine (276 mg, 2.13 mmol) at 0° C. followed by the addition of methylchloroformate (109 mg, 1.16 mmol) and allowed to stir at the same temperature for 2 h. The reaction mixture was diluted with ethyl acetate (70 mL) and the organic portion was washed with water followed by brine and dried over sodium sulfate. Upon concentration and purification by silica gel column chromatography (methanol/chloroform, 1:19), the title compound was obtained as white powder (140 mg, 40%). Mp.218° C.

¹H NMR (DMSO-d₆): δ 8.62 (s, 1H), 7.90–7.61 (m, 2H), 7.35 (t, J=8.6 Hz, 1H), 4.31 (d, J=5.9 Hz, 2H), 3.82–3.61 (m, 2H), 3.60 (s, 3H), 3.50–3.31 (m, 2H), 3.11–2.80 (m, 4H).

MS (m/e): 368 (M⁺+1), 336, 276.

EXAMPLE 49

N-{1-[4-(1,1-Dioxo-1lambda*6*-thiomorpholin-4-yl)-3-fluoro-phenyl]-1H-[1,2,3]triazol-4-ylmethyl}-acetamide

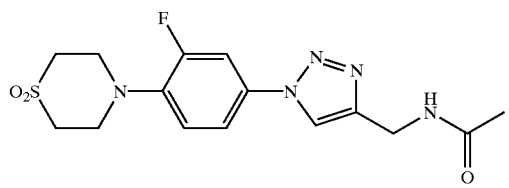

The title compound (0.225 g, 72%) was obtained from 4-[4-(4-azidomethyl-[1,2,3]triazol-1-yl)-2-fluoro-phenyl]-thiomorpholine 1,1-dioxide (0.3 g, 0.85 mmol), as reported in Example 23, by a procedure as described in Example 41. Mp. 198° C.

$^1$H NMR (CDCl$_3$): δ 8.01 (s, 1H), 7.60–7.40 (m, 2H), 7.05 (t, J=8.8 Hz, 1H), 4.58 (d, J=5.9 Hz, 2H), 3.90–3.70 (m, 4H), 3.30–3.10 (m, 4H), 2.02 (s, 3H).

MS (m/e): 368 (M$^+$+1).

EXAMPLE 50

N-{1-[3-Fluoro-4-(1-oxo-1lambda*4*-thiomorpholin-4-yl)-phenyl]-1H-[1,2,3]triazol-4-ylmethyl}-formamide

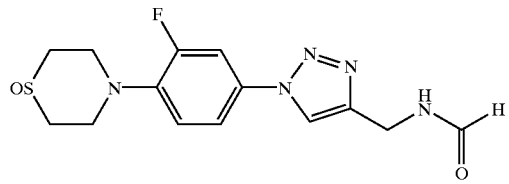

A solution of C-{1-[3-fluoro-4-(1-oxo-1lambda*4*-thiomorpholin-4-yl)-phenyl]-1H-[1,2,3]triazol-4-yl}-methylamine (100 mg, 0.32 mmol), obtained in Example 27, in acetonitrile (5 mL) and ammonium formate (82 mg, 1.3 mmol) was refluxed for 20 h. The reaction mixture was absorbed on silica gel and purified by column chromatography (ethyl acctate/pet. ether, 1:1) to obtain the title compound (87 mg, 80%). Mp. 182–184° C.

$^1$H NMR (CDCl$_3$+DMSO-d$_6$): δ 8.52 (br s, 1H), 8.01 (s, 1H), 7.82–7.61 (m, 2H), 7.25 (t, J=9.1 Hz, 1H), 4.55 (d, J=5.4 Hz, 2H), 3.80 (t, J=11.7 Hz, 2H), 3.52–3.30 (m, 2H), 3.20–2.80 (m, 4H).

MS (m/e): 338 (M$^+$+1).

EXAMPLE 51

N-[1-(3,5-Difluoro-4-morpholin-4-yl-phenyl)-1H-[1,2,3]triazol-4-ylmethyl]-thioacetamide

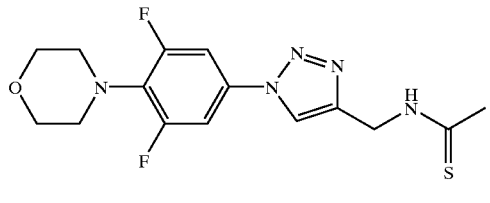

A solution of N-[1-(3,5-difluoro-4-morpholin-4-yl-phenyl)-1H-[1,2,3]triazol-4-ylmethyl]-acetamide (0.2 g, 0.59 mmol), obtained in Example 41, and Lawesson's reagent (0.13 g, 0.33 mmol) in anhydrous dioxane (10 mL) was refluxed for 2 h. The reaction mixture was allowed to cool down to room temperature and extracted with ethyl acetate (20 mL×2) after additon of water (20 mL). Combined ethyl acetate portion was washed with aqueous NaHCO$_3$ solution followed by brine and dried over sodium sulfate. The residue obtained after evaporation of solvent was purified by silica gel column chromatography (EtOAc/CHCl$_3$, 1:1). Yield—0.2 g, 95%. Mp. 190° C.

$^1$H NMR (CDCl$_3$): δ 8.05 (s, 1H), 7.40–7.20 (m, 2H), 5.01 (d, J=5.8 Hz, 2H), 3.90–3.75 (m, 4H), 3.35–3.20 (m, 4H), 2.60 (s, 3H).

MS (m/e): 354 (M$^+$+1), 325, 251.

EXAMPLE 52

N-[1-(3-Fluoro-4-morpholin-4-yl-phenyl)-1H-[1,2,3]triazol-4-ylmethyl]-thioacetamide

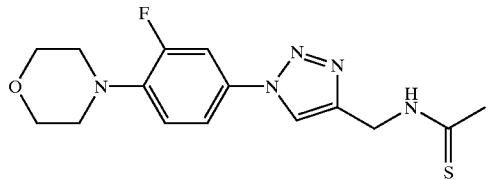

The title compound (0.28 g, 90%) was obtained from N-[1-(3-fluoro-4-morpholin-4-yl-phenyl)-1H-[1,2,3]triazol-4-ylmethyl]-acetamide (0.3 g, 0.94 mmol), as reported in Example 42, and Lawessori's reagent (0.37 g, 0.94 mmol) by a procedure as described in Example 51. Mp. 192° C.

$^1$H NMR (CDCl$_3$): δ 10.35 (br s, 1H), 8.45 (s, 1H), 7.70–7.50 (m, 2H), 7.10 (t, J=8.7 Hz, 1H), 4.89 (d, J=4.9 Hz, 2H), 3.90–3.75 (m, 4H), 3.20–3.05 (m, 4H), 2.50 (s, 3H).

MS (m/e): 335 (M$^+$), 307, 274.

EXAMPLE 53

N-{1-[3-Fluoro-4-(1-oxo-1lambda*4*-thiomorpholin-4-yl)-phenyl]-1H-[1,2,3]triazol-4-ylmethyl}-thioacetamide

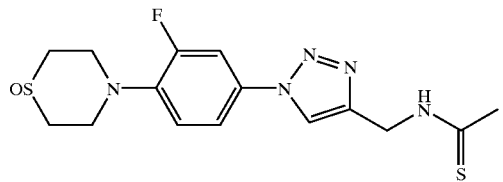

To a stirring solution of C-{1-[3-fluoro-4-(1-oxo-1lambda*4*-thiomorpholin-4-yl)-phenyl]-1H-[1,2,3]triazol-4-yl}-methylamine (0.1 g, 0.32 mmol), obtained in Example 27, in dichloromethane (5 mL) was added triethylamine (72 mg, 0.71 mnol) followed by the addition of ethyldithioacetate (47 mg, 0.39 mmol) and stirred for 24 h. The resulting product was absorbed on silica gel and purifiled by column chromatography (methanol/chloroform, 1:24) to yield of the title compound (30 mg, 25%). Mp. 245° C.

$^1$H NMR (CDCl$_3$+DMSO-d$_6$): δ 10.50 (br s, 1H), 8.71 (s, 1H), 7.90–7.71 (m, 2H), 7.36 (t, J=9.1 Hz, 1H), 4.80 (d, J=5.4 Hz, 2H), 3.65 (t, J=11.5 Hz, 2H), 3.50–3.31 (br s, 2H), 3.20–2.80 (m, 4H), 2.45 (s, 3H).

MS (m/e): 368 (M$^+$+1), 157.

Note: Esters of thiocarbamate acids were obtained as a mixture of rotamers in the ratio of 1:4, which is evident from the $^1$H-NMR spectra.

EXAMPLE 54

1-(3,5-Difluoro-4-morpholin-4-yl-phenyl)-1H-[1,2,3]triazol-4-ylmethyl]-thiocarbamic acid O-methyl ester

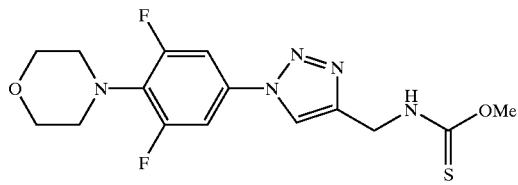

4-[2,6-Difluoro-4-(4-isothiocyanatomethyl-[1,2,3]triazol-1-yl)-phenyl]-morpholine (0.28 g, 0.83 mmol), obtained in Example 33, was refluxed in methanol (15 mL) for 15 h. Evaporation of solvent and purification of the resulting material by silica gel column chromatography (chloroform/ethylacetate, 1/4) yielded the title compound as white solid (150 mg, 60%). Mp. 135° C.

$^1$H NMR (CDCl$_3$): δ 8.04 & 7.80 (2 s, in the ratio of 4:1, rotamers, 1H), 7.40–7.20 (m, 2H), 6.95 (br s, —NH), 4.91 & 4.7 (2 d, in the ratio of 4:1, rotamers, J=5.9 Hz, 2H), 4.1 & 4.0 (2 s, in the ratio of 1:4, rotamers, 3H), 3.90–3.80 (m, 4H), 3.35–3.20 (m, 4H).

MS (m/e): 370 (M$^+$+1), 338, 279, 251.

EXAMPLE 55

[1-(3-Fluoro-4-morpholin-4-yl-phenyl)-1H-[1,2,3]triazol-4-ylmethyl]-thiocarbamic acid O-methyl ester

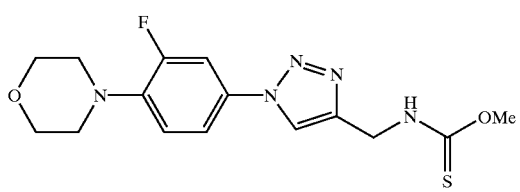

The title compound (0.17 g, 60%) was obtained from 4-[2-fluoro-4-(4-isothiocyanatomethyl-[1,2,3]triazol-1-yl)-phenyl]-morpholine (0.25 g, 0.78 mmol), as reported in Example 34, by a procedure as described in Example 54. Mp. 148° C.

$^1$H NMR (CDCl$_3$+DMSO-d$_6$): δ 8.58 (br s, 1H), 8.15 & 8.00 (2 s, in the ratio of 4:1, rotamers, 1H), 7.60–7.40 (m, 2H), 7.05 (t, J=8.8 Hz, 1H), 4.90 & 4.61 (2 d, in the ratio of 4:1, rotamers, J=5.9 Hz, 2H), 4.11 & 4.00 (2 s, in the ratio of 1:4, rotamers, 3H), 3.95–3.80 (m, 4H), 3.30–3.10 (m, 4H).

MS (m/e): 351 (M$^+$), 319, 233, 175.

EXAMPLE 56

[1-(3,5-Difluoro-4-thiomorpholin-4-yl-phenyl)-1H-[1,2,3]triazol-4-ylmethyl]-thiocarbamic acid O-methyl ester

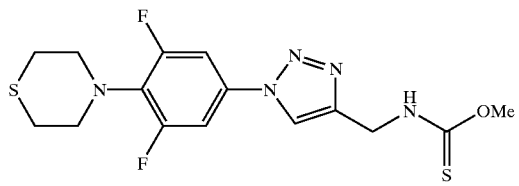

The title compound (0.15 g, 60%) was obtained as white solid from 4-[2,6-difluoro-4-(4-isothiocyanatomethyl-[1,2,3]triazol-1-yl)-phenyl]-thiomorpholine (0.21 g), as reported in Example 35, by a procedure as described in Example 54. Mp. 127° C.

$^1$H NMR (CDCl$_3$): δ 8.03 & 7.80 (2 s, in the ratio of 4:1, rotamers, 1H), 7.40–7.20 (m, 2H), 7.09 (br s, 1H), 4.91 & 4.65 (2 d, in the ratio of 4:1, rotamers, J=5.9 Hz, 2H), 4.10 & 4.01 (2 s, in the ratio of 1:4, rotamers, 3H), 3.55–3.35 (m, 4H), 2.90–2.70 (m, 4H).

MS (m/e): 386 (M$^+$+1), 354, 267.

EXAMPLE 57

1-[3,5-Difluoro-4-(1-oxo-1lambda*4*-thiomorpholin-4-yl)-phenyl]-1H-[1,2,3]triazol-4-ylmethyl}-thiocarbamic acid O-methyl ester

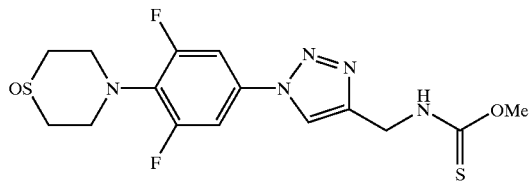

The title compound (0.4 g, 75%) was obtained as white solid from 4-[2,6-difluoro-4-(4-isothiocyanatomethyl-[1,2,3]triazol-1-yl)-phenyl]-thiomorpholine 1-oxide (0.49 g), as reported in Example 38, by a procedure as described in Example 54. Mp. 202° C.

$^1$H NMR (CDCl$_3$): δ 8.08 and 7.80 (2 s, in the ratio of 4:1, rotamers, 1H), 7.40–7.30 (m, 2H), 7.10 (br s, 1H), 4.91 & 4.66 (2 d, in the ratio of 4:1, rotamers, J=5.9 Hz, 2H), 4.20–4.01 (m, 2H), 4.11 & 4.00 (2 s, in the ratio of 1:4, rotamers, 3H), 3.40–3.20 (m, 2H), 3.10–2.90 (m, 4H).

MS (m/e): 402 (M$^+$+1), 370, 149.

EXAMPLE 58

{1-[4-(1,1-Dioxo-1lambda*6*-thiomorpholin-4-yl)-3,5-difluoro-phenyl]-1H-[1,2,3]triazol-4-ylmethyl}-thiocarbamic acid O-methyl ester

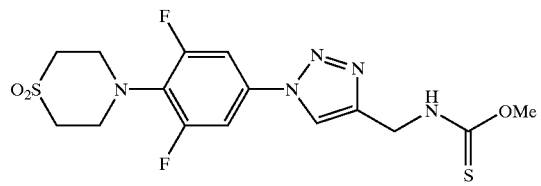

The title compound (0.26 g, 80%) was obtained from 4-[2,6-difluoro-4-(4-isothiocyanatomethyl-[1,2,3]triazol-1-yl)-phenyl]-thiomorpholine 1,1-dioxide (0.27 g), as in Example 39, by a procedure as described in Example 54. Mp. 162° C.

$^1$H NMR (CDCl$_3$): δ 8.08 & 7.81 (2 s, in the ratio of 4:1, rotamers, 1H), 7.36 (d, J=8.6 Hz, 2H), 6.95 (m, 1H), 4.90 & 4.65 (2 d, in the ratio of 4:1, rotamers, J=5.9 Hz, 2H), 4.15 and 4.01 (2 s, in the ratio of 1:4, rotamers, 3H), 3.80–3.60 (m, 4H), 3.30–3.10 (m, 4H).

MS (m/e): 418 (M$^+$+1), 386, 299, 279.

EXAMPLE 59

[1-(3-Fluoro-4-thiomorpholin-4-yl-phenyl)-1H-[1,2,3]triazol-4-ylmethyl]-thiocarbamic acid O-methyl ester

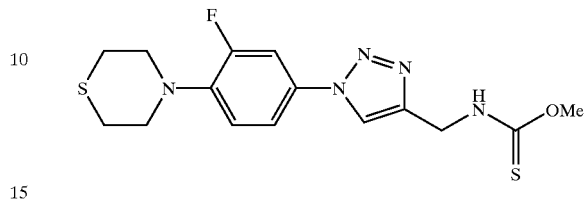

The title compound (0.115 g, 60%) was obtained from 4-[2-fluoro-4-(4-isothiocyanatomethyl-[1,2,3]triazol-1-yl)-phenyl]-thiomorpholine (0.175 g), as reported in Example 36, by a procedure as described in Example 54. Mp.168° C.

$^1$H NMR (CDCl$_3$): δ 9.12 (s, 1H), 8.24 & 8.13 (2 s, in the ratio of 4:1, rotamers, 1H), 7.60–7.41 (m, 2H), 7.12 (t, J=8.8 Hz, 1H), 4.85 & 4.55 (2 d, in the ratio of 4:1, rotamers, J=5.9 Hz, 2H), 4.05 & 3.96 (2 s, in the ratio of 1:4, rotamers, 3H), 3.50–3.30 (m, 4H), 2.90–2.70 (m, 4H).

MS (m/e): 368 (M$^+$+1), 321.

EXAMPLE 60

{1-[3-Fluoro-4-(1-oxo-1lambda*4*-thiomorpholin-4-yl)-phenyl]-1H-[1,2,3]triazol-4-ylmethyl}-thiocarbamic acid O-methyl ester

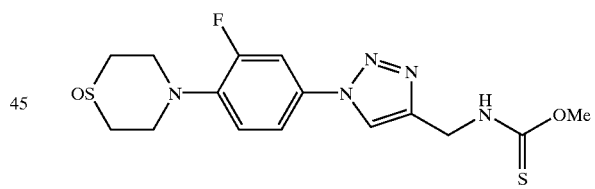

The title compound (0.4 g, 80%) was obtained from 4-[2-fluoro-4-(4-isothiocyanatomethyl-[1,2,3]triazol-1-yl)-phenyl]-thiomorpholine1-oxide, (0.48 g), as reported in Example 37, by a procedure as described in Example 54. Mp.198° C.

$^1$H NMR (CDCl$_3$+DMSO-d$_6$): δ 9.37 (br s, 1H), 8.46 & 8.40 (2 s, in the ratio of 4:1, rotamers, 1H), 7.75–7.50 (dt, J=2.4 & 11.9 Hz, 2H), 7.25 (t, J=8.8 Hz, 1H), 4.82 & 4.61 (2 d, in the ratio of 4:1, rotamers, J=5.9 Hz, 2H), 4.04 & 3.97 (2 s, in the ratio of 1:4, rotamers, 3H), 3.85 (t, J=11.5 Hz, 2H), 3.50–3.20 (m, 2H), 3.20–2.80 (m, 4H).

MS (m/e): 384 (M$^+$+1), 352, 336, 265, 175.

EXAMPLE 61

{1-[4-(1,1-Dioxo-1lambda*6*-thiomorpholin-4-yl)-3-fluoro-phenyl]-1H-[1,2,3]triazol-4-ylmethyl]-thiocarbamic acid O-methyl ester

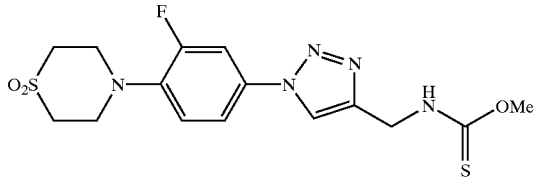

The title compound (0.22 g, 80%) was obtained from 4-[2-fluoro-4-(4-isothiocyanatomethyl-[1,2,3]triazol-1-yl)-phenyl]-thiomorpholine1-oxide (0.27 g), obtained in Example 40, by a procedure as described in Example 54. Mp. 184° C.

$^1$H NMR (CDCl$_3$+DMSO-d$_6$): δ 9.46 (br s, 1H), 8.49 & 8.41 (2 s, in the ratio of 4:1, rotomers, 1H), 7.70–7.60 (m, 2H), 7.25 (t, J=8.8 Hz, 1H), 4.77 & 4.60 (2 d, in the ratio of 4:1, rotamers, J=5.4 Hz, 2H), 4.05 & 3.93 (2 s, in the ratio of 1:4, rotamers, 3H), 3.50–3.50 (m, 4H), 3.20–3.10 (m, 4H).

MS (m/e): 400 (M$^+$+1), 368, 281.

EXAMPLE 62

{1-[4-(1,4-Dioxa-8-aza-spiro[4.5]dec-8-yl)-3-fluoro-phenyl]-1H-[1,2,3]triazol-4-ylmethyl}-thiocarbamic acid O-methyl ester

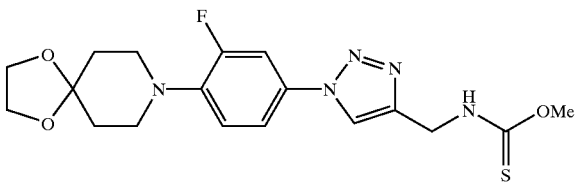

To a solution of C-{-[4-(1,4-dioxa-8-aza-spiro[4.5]dec-8-yl)-3-fluoro-phenyl]-1H-[1,2,3]triazol-4-yl}-methylamine (1.5 g, 4.5 mmol), obtained in Example 31, in THF (50 ml) was added triethylamine (0.68 g, 6.7 mmol) followed by the addition of carbondisulfide (0.5 g, 6.7 mmol) and stirred at room temperature for 16 h. The reaction mixture was quenched with ethylchloroformate (0.73 g, 6.7 mmol) and allowed to stir for additional 2 h. The reaction mixture was then diluted with ethyl acetate (200 ml) and the organic portion was washed with water followed by brine and dried over sodium sulfate. Evaporation of volatiles left a residue, which was refluxed with methanol (60 ml) for 16 h. Upon concentration and purification of the resulting residue by a silica gel column (ethyl acetate/pet. ether, 1:4), the title compound was obtained as cream colour solid (900 mg, 56%). Mp. 135–137° C.

$^1$H NMR (CDCl$_3$): δ 8.05 (s, 1H), 7.50–7.29 (m, 2H), 7.21 (t, J=8.6 Hz, 1H), 7.01 (br s, —NH), 4.88 & 4.69 (2 d, in the ratio of 4:1, rotamers, J=5.9 Hz, 2H), 4.11 & 4.02 (2 s, in the ratio of 1:4, rotamers, 3H), 3.30 (t, J=5.4 Hz, 4H), 1.95 (t, J=5.4 Hz, 4H).

MS (m/e): 408 (M$^+$+1), 376 (M$^+$–OMe), 289, 180.

EXAMPLE 63

{1-[3-Fluoro-4-(1-imino-1lambda*4*-thiomorpholin-4-yl)-phenyl]-1H-[1,2,3]triazol-4-ylmethyl}-thiocarbamic acid O-methyl ester

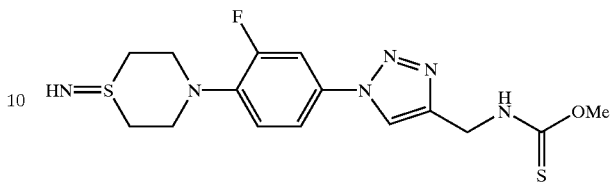

To an ice-cooled solution of the 4-[4-(4-aminomethyl-[1,2,3]triazol-1-yl)-2-fluoro-phenyl]-1-imino-1lambda*4*-thiomorpholine (100 mg, 0.3 mmol), obtained in Example 32 in CHCl$_3$ (10 ml) was added sat. sodium bicarbonate solution followed by thiophosgene (36 μl, 0.33 mmol). The reaction mixture was stirred at room temperature for 0.5 h and then diluted with ethyl acetate (30 ml). The organic portion was washed with water followed by brine and dried over sodium sulfate. Evaporation of volatiles left a residue, which was refluxed with methanol (20 ml) for 20 h. Removal of volatiles and purification of the resulting residue by silica gel column chromatography (CHCl$_3$/MeOH, 1:4) yielded the title compound as white solid (70 mg, 71%). Mp. 198° C.

$^1$H NMR (CDCl$_3$): δ 9.69 (br s, 1H), 8.72 & 8.65 (2 s, in the ratio of 4:1, rotamers, 1H), 7.88–7.65 (m, 2H), 7.40 (t, J=8.9 Hz, 1H), 4.75 & 4.45 (2 d, in the ratio of 4:1, rotamters, J=5.4 Hz, 2H), 4.01 & 3.90 (2 s, in the ratio of 1:4, rotamers, 3H), 3.60 (t, J=11.8 Hz, 2H), 3.49–3.30 (br s, 2H), 3.22–2.80 (m, 4H).

MS (m/e): 382 (M$^+$+1), 291, 249, 104.

EXAMPLE 64

1-[1-(3,5-Difluoro-4-morpholin-4-yl-phenyl)-1H-1,2,3]triazol-4-ylmethyl]-3-methyl-thiourea

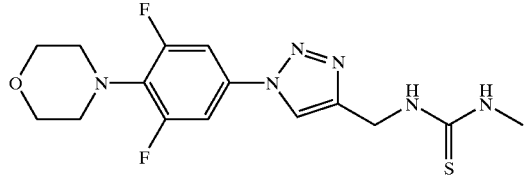

To a solution of 40% methylamine (10 mL) was added 4-[2,6-difluoro-4-(4-isothiocyanatomethyl-[1,2,3]triazol-1-yl)-phenyl]-morpholine (0.2 g), obtained in Example 33, and stirred at room temperature for 30 min. The reaction mixture was neutralized with 1N HCl and diluted with water. Water layer was extracted with ethyl acetate (20 mL×2) and the combined organic layer was washed with brine and dried over sodium sulfate. Upon concentration and purification of the resulting residue by silica gel column chromatography (eluent; chloroform/ethylacetate, 8:2), the title compound was obtained as pale yellow crystals (0.12 g, 50%). Mp. 181° C.

$^1$H NMR (CDCl$_3$): δ 8.09 (s, 1H), 7.40–7.20 (m, 2H), 6.60 (br s, 4H), 6.35 (br s, 1H), 4.93 (d, J=5.4 Hz, 2H), 3.90–3.75 (m, 4H), 3.35–3.20 (m, 4H), 3.01 (d, J=4.9 Hz, 3H).

MS (m/e): 369 (M$^+$+1), 335, 296, 251.

EXAMPLE 65

1-Ethyl-3-{1-[3-fluoro-4-(1-oxo-1lambda*4*-thiomorpholin-4-yl)-phenyl]-1H-[1,2,3]triazol-4-ylmethyl}-thiourea

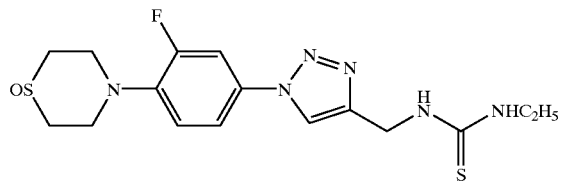

To a stirring solution of C-{1-[3-fluoro-4-(1-oxo-1lambda*4*-thiomorpholin-4-yl)-phenyl]-1H-[1,2,3]triazol-4-yl}-methylamine (0.2 g, 0.65 mmol), obtained in Example 27, in dichloromethane (10 mL) was added triethylamine (143 mg, 1.4 mmol) at 0° C. followed by the addition of ethyl isothiocyanate (112 mg, 1.28 mmol). Reaction mixture was allowed to come to room temperature and stirred at the same temperature for 18 h. Ethyl acetate (50 mL) was added and the organic portion was washed with water followed by brine and dried over sodium sulfate, Upon concentration and purification by silica gel column chromatography (methanol/chloroform, 2:3) was obtained the title compound as white powder (100 mg, 39%). Mp. 204° C.

$^1$H NMR (DMSO-d$_6$): δ 8.61 (s, 1H), 7.92–7.65 (m, 21H), 7.61 (br s, 1H), 7.35 (t, J=8.6 Hz, 1H), 4.80 (d, J=4.9 Hz, 2H), 3.82–3.61 (t, J=9.0 Hz, 2H), 3.51–3.30 (br s, 5H), 3.20–2.80 (m, 4H), 1.07 (t, J=7.2 Hz, 3H).

MS (m/e): 397 (M$^+$+1), 352, 310, 265, 175, 157, 90.

EXAMPLE 66

1-[3-fluoro-4-(4-thiomorpholinyl)phenyl]-1H-1,2,3-triazol-4-ylmethylamino-hydrazinomethanethione

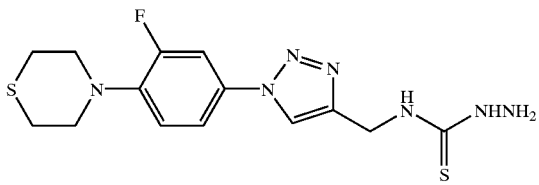

To a stirring solution of C-[1-(3-fluoro-4-thiomorpholin-4-yl-phenyl)-1H-[1,2,3]triazol-4-yl]-methylamine (0.25 g, 0.85 mmol), obtained in Example 19, in DMF (2 mL) was added 4-(4-methylphenyl)-3-thiosemicarbazide (231 mg, 1.27 mmol) and heated to 90° C. for 12 h. Reaction mixture was diluted with ethyl acetate (25 mL) and the organic portion was washed with water followed by brine and dried over sodium sulfate. Upon concentration and purification by silica gel column chromatography (methanol/chloroform, 1:24), the title compound was obtained as cream colored solid (110 mg, 35%). Mp. 174–176° C.

$^1$H NMR (DMSO-d$_6$): δ 8.62 (br s, 2H), 8.11 (s, 1H), 7.85–7.60 (m, 2H), 7.25 (t, J=9.1 Hz, 1H), 4.40 (d, J=5.6 Hz, 2H), 3.50–3.30 (m, 4H), 2.92–2.71 (m, 4H).

MS (m/e): 368 (M$^+$), 322, 293, 248, 174, 148, 104.

EXAMPLE 67

[1-(3-Fluoro-4-morpholin-4-yl-phenyl)-1H-[1,2,3] triazol-4-ylmethyl]-dithiocarbamic acid methyl ester

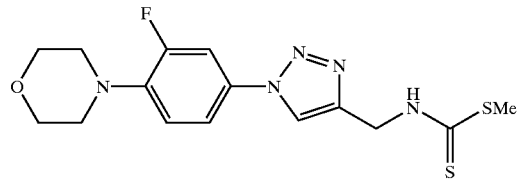

A solution of C-[1-(3-fluoro-4-morpholin-4-yl-phenyl)-1H-[1,2,3]triazol-4-yl]-methylamine (0.3 g, 1.08 mmol), obtained in Example 17, carbon disulfide (0.13 mL, 2.16 mmol) and triethylamine (0.1 mL, 1.08 mmol) in anhydrous THF (20 mL) was allowed to stir at 0° C. for 7 h. The reaction mixture was stirred for additional 0.5 h after the addition of methyl iodide (0.15 g, 1.08 mmol) and then diluted with ethyl acetate (50 ml.). The organic portion was washed with water followed by brine and dried over sodium sulfate. Evaporation of volatiles and purification of the resulting residue by silica gel column chromatography yielded the title compound as white solid (0.35 g, 85%). Mp. 148° C.

$^1$H NMR (CDCl$_3$): δ 8.03 (s, 1H), 7.97 (br s, 1H), 7.55–7.35 (m, 2H), 7.01 (t, J=8.8 Hz, 1H), 5.08 (d, J=5.4 Hz, 2H), 4.00 (s, 3H), 4.01–3.80 (m, 4H), 3.25–3.05 (m, 4H).

MS (m/e): 320 (M–47), 233, 149.

EXAMPLE 68

{1-[3-Fluoro-4-(1-oxo-1lambda*4*-thiomorpholin-4-yl)-phenyl]-1H-[1,2,3]triazol-4-ylmethyl}-dithiocarbamic acid methyl ester

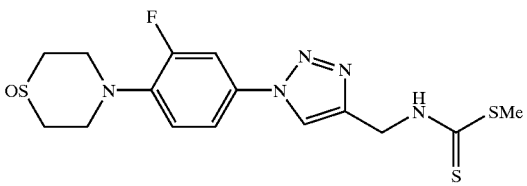

The title compound (0.21 g, 80%) was prepared from C-{1-[3-fluoro-4-(1-oxo-1lambda*4*-thiomorpholin-4-yl)-phenyl]-1H-[1,2,3]triazol-4-yl}-methylamine (0.2 g, 0.65 mmol), obtained in Example 27, by a procedure as described in Example 67. Mp. 184° C.

$^1$H NMR (CDCl$_3$+DMSO-d$_6$): δ 10.26 (br s, 1H), 8.32 (s, 1H), 7.80–7.60 (m, 2H), 7.35 (t, J=8.8 Hz, 1H), 4.95 (d, J=5.9 Hz, 2H), 3.75 (t, J=11.5 Hz, 2H 3.20–2.80 (m, 4H), 2.56 (s, 3H).

MS (m/e): 400 (M$^+$+1), 352,334, 265, 175.

EXAMPLE 69

{1-[4-(1,1-Dioxo-1lambda*6*-thiomorpholin-4-yl)-3-fluoro-phenyl]-1H-[1,2,3]triazol-4-ylmethyl}-dithiocarbamic acid methyl ester

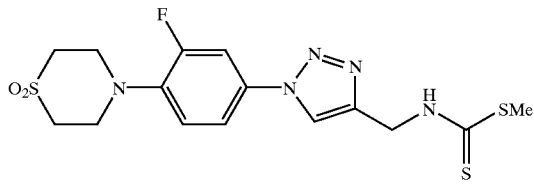

The title compound (0.20 g, 80%) was obtained from C-{1-[4-(1,1-dioxo-1lambda*6*-thiomorpholin-4-yl)-3-fluoro-phenyl]-1H-[1,2,3]triazol-4-yl}-methylamine (0.2 g, 0.48 mmol), obtained in Example 30, by a procedure as described in Example 67. Mp. 139–140° C.

$^1$H NMR (CDCl$_3$): δ 7.98 (s, 1H), 7.60–7.40 (m, 211), 7.13 (t, J=8.8 Hz, 1H), 4.94 (s, 2H), 3.80–3.60 (m, 4H), 3.35–3.15 (m, 4H), 1.59 (s, 3H).

MS (m/e): 368 (M$^+$—SCH$_3$), 281.

EXAMPLE 70

1-Benzoyl-3-[1-(3-fluoro-4-morpholin-4-yl-phenyl)-1H-[1,2,3]trlazol-4-ylmethyl]-thiourea

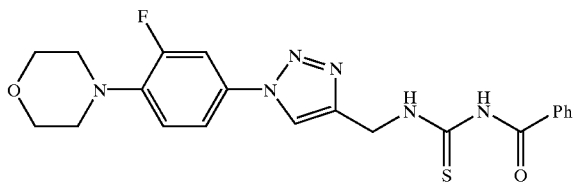

A mixture of C-[1-(3-fluoro-4-morplholin-4-yl-phenyl)-1H-[1,2,3]triazol-4-yl]-methylamine (0.3 g, 1.08 mmol), obtained in Example 17, and benzoylisothiocyanate (0.2 g, 1.3 mmol), in anhydrous acetone (20 mL) was allowed to stir at room temperature for 3 h. Upon concentration and purification of the resulting residue by column chromatography, the title compound was obtained as white solid (0.28 g, 60%). Mp. 138° C.

$^1$HNMR (CDCl$_3$): δ 11.25 (brs, 1H), 9.12 (brs, 1H), 8.13 (s, 1H), 7.90–7.70 (m, 3H), 7.70–7.30 (m, 4H), 7.05 (t, J=8.7 Hz, 1H), 5.12 (d, J=5.4 Hz, 2H), 4.01–3.80 (m, 4H), 3.25–3.05 (m, 4H).

MS (m/e): 441 (M$^+$), 422, 382, 320, 233, 122, 105.

EXAMPLE 71

Pyrazine-2-carboxylic acid [1-(3-fluoro-4-morpholin-4-yl-phenyl)-1H-[1,2,3]triazol-4-ylmethyl]-amide

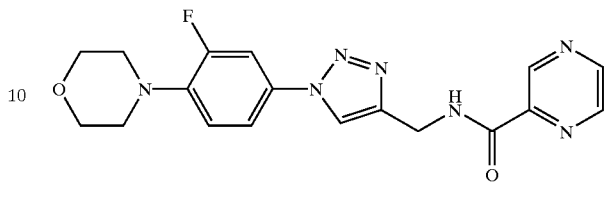

To a solution of pyrazine 2-carboxylic acid (0.09 g, 0.72 mmol) and DCC (0.2 g, 1.08 mmol) in dry acetonitrile (20 mL) was added catalytic amount of N,N-dimethylaminopyridine (DMAP) and stirred for 15 min. A solution of C-[1-(3-fluoro-4-morpholin-4-yl-phenyl)-1H-[1,2,3]triazol-4-yl]-methylamine (0.2 g, 0.72 mmol), obtained in Example 17, in dry acetonitrile (5 mL) was then added to the reaction mixture and stirred for additional 4 h. Evaporation of acetonitrile left a thick liquid, which was poured into crushed ice to obtain a white solid. The solid was further purified by column chromatography. Yield—0.15 g, 60%. Mp. 215° C.

$^1$H NMR (CDCl$_3$): δ 9.40 (s, 1H), 8.70 ((, J=2.4 Hz, 1H), 8.54 (s, 1H), 8.40 (br s, 1H), 8.01 (s, 1H), 7.55–7.35 (m, 2H), 7.02 (t, J=8.8 Hz, 1H), 4.84 (d, J=6.4 Hz, 1H), 4.01–3.80 (m, 411), 3.30–3.10 (m, 4H).

MS (m/e): 384 (M$^+$+1), 336, 206, 172.

EXAMPLE 72

N-{1-[3-fluoro-4-(4-thiomorpholinyl)phenyl]-1H-1,2,3-triazol-4-ylmethyl}-pyrazine-2-carboxamide

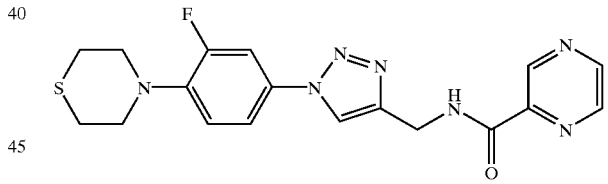

A solution of pyrazine-2-carboxylic acid (127 mg, 1.02 mmol) and DCC (211 mg, 1.02 mmol) in acetonitrile (5 mL) was added to a stirring solution of C-[1-(3-fluoro-4-thiomorpholin-4-yl-phenyl)-1H-[1,2,3]triazol-4-yl]-methylamine (200 mg, 0.68 mmol), obtained in Example 19, in dry acetonitrile (10 mL) and allowed to stir at room temperature for 6 h. The reaction mixture was then poured into ice-cooled water and extracted with ethyl acetate (20 mL×2). The organic portion was washed with water followed by brine and dried over sodium sulfate. Upon concentration and purification by silica gel column chromatography (acetone/chloroform, 15:85) the title compound was obtained (245 mg, 90%). Mp. 216–218° C.

H NMR (CDCl$_3$): δ 9.40 (s, 1H), 8.81 (s, 1H), 8.55 (s, 1H), 8,42 (br s, 1H), 8.01 (s, 1H), 7.55–7.35 (m, 2H), 7.05 (t, J=8.6 Hz, 1H), 4.85 (d, J=5.8 Hz, 2H), 3.50–3.30 (m, 4H), 2.90–2.70 (m, 4H).

MS (m/e): 400 (M$^+$+1), 95.

EXAMPLE 73

Dithiocarbonic acid O-[1-(3-fluoro-4-morpholin-4-yl-phenyl)-1H-[1,2,3]triazol-4-ylmethyl] ester S-methyl ester

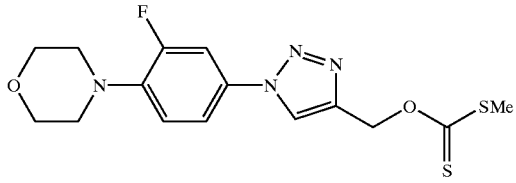

To a solution of [1-(3-fluoro-4-morpholin-4-yl-phenyl)-1H-[1,2,3]triazol-4-yl]-methanol (0.3 g, 1.08 mmol), obtained in Example 2, in DMF, (20 mL) was added potassium tert-butoxide (0.12 g, 1.08 mmol) at 0–5° C. followed by carbon disulfide (0.24 g, 3.23 mmol) and the reaction mixture was stirred at the same temperature for 3 h. Subsequently, methyl iodide (0.15 g, 1.08 mmol) was added to it. The reaction mixture was then diluted with water and extracted with ethyl acetate (30 mL×2). Combined ethyl acetate portion was washed with water followed by brine and dried over sodium sulfate. The oily liquid obtained upon concentration was purified by column chromatography to produce the title compound as white solid (0.2 g, 51%). Mp. 118° C.

$^1$H NMR (CDCl$_3$): δ 8.03 (s, 1H), 7.55–7.35 (m, 2H), 7.01 (t, J=8.6 Hz, 1H), 5.84 (s, 2H), 4.00 (s, 3H), 4.01–3.80 (m, 4H), 3.25–3.05 (m, 4H), 2.56 (s, 3H).

MS (m/e): 369 (M$^+$+1), 309, 279, 233.

EXAMPLE 74

4-{2-Fluoro-4-[4-(pyridin-2-yloxymethyl)-[1,2,3]triazol-1-yl]-phenyl}-morpholine & 1-[1-(3-Fluoro-4-morpholin-4-yl-phenyl)-1H-[1,2,3]triazol-4-ylmethyl]-1H-pyridin-2-one (74A)

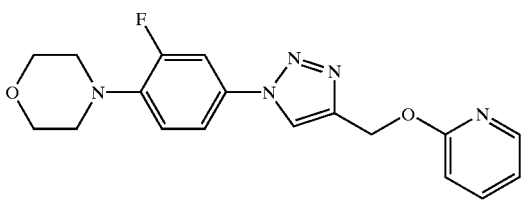

(74B)

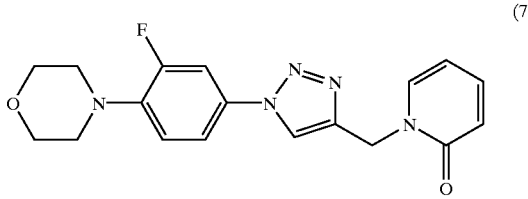

To a suspension of sodium hydride (23 mg, 0.97 mmol) in dry DMF (5 mL) was added 2-pyridinol (0.11 g, 1.21 mmol) and allowed to stir for 10 min. A solution of Methanesulfonic acid 1-(3-fluoro-4-morpholin-4-yl-phenyl)-1H-[1,2,3]triazol-4-ylmethyl ester (0.3 g, 0.81 mmol), obtained in Example 8, in dry DMF (2 mL) was added to the above suspension and heated to 60° C. for 2 h. lThe reaction mixture was then diluted with ethyl acetate (30 mL) and organic portion was washed with water followed by brine and dried over sodium sulfate. Evaporation of volatiles and purification of the resulting residue by column chromatography yielded initially compound 74A (20 mg, 10%) followed by compound 74B (150 mg, 53%). Mp. 158° C.

Compound 74A $^1$H NMR (CDCl$_3$): δ 8.20–8.10 (m, 1H), 8.01 (s, 1H), 7.70–7.40 (m, 3H), 7.10–6.75 (m, 3H), 5.58 (s, 2H), 4.01–3.80 (m, 4H), 3.30–3.10 (m, 4H).

MS (m/e): 356 (M$^+$+1), 263, 233, 113, 96.

Compound 74B $^1$H NMR (CDCl$_3$): δ 8.17 (s, 1H), 7.63 (dd, J=6.8 & 1.5 Hz, 1H), 7.6–7.30 (m, 3H), 7.0 (t, J=8.8 Hz, 1H), 6.73 (d, J=9.3 Hz, 1H), 6.22 (t, J=6.6 Hz, 1H), 5.23 (s, 2H), 4.01–3.80 (m, 4H), 3.30–3.10 (m, 4H).

MS (m/e): 356 (M$^+$+1).

EXAMPLE 75

N-{1-[3-Fluoro-4-(4-thiomorpholinyl)phenyl]-1H-1,2,3-triazol-4-ylmethyl}-pyridine-2-carboxamide

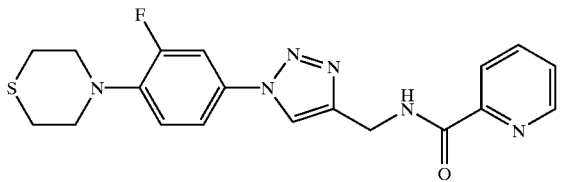

The title compound (245 mg, 90%) was obtained from C-[1-(3-fluoro-4-thiomorpholin-4-yl-phenyl)-1H-[1,2,3]triazol-4-yl]-methylamine (200 mg, 0.68 mmol), as reported in Example 19, pyridine-2-carboxylic acid (126 mg, 1.02 mmol) and DCC (211 mg, 1.02 mmol), by a procedure as described in Example 71. Mp. 190–192° C.

$^1$H NMR (CDCl$_3$): δ 8.65 (br s, 1H), 8.55 (d, J=4.9 Hz, 1H), 8.22 (d, J=7.8 Hz, 1H), 8.01 (s, 1H), 7.50–7.31 (m, 3H), 7.05 (t, J=8.7 Hz, 1H), 4.85 (d, J=5.8 Hz, 2H), 3.50–3.30 (m, 4H), 2.90–2.70 (m, 4H).

MS (m/e): 399 (M$^+$+1), 224, 148, 100, 93.

EXAMPLE 76

[1-(3-Fluoro-4-morpholin-4-yl-phenyl)-1H-[1,2,3]triazol-4-ylmethyl]-thiourea

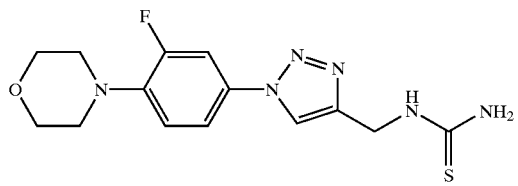

To a solution of 4-[2-fluoro-4-(4-isothiocyanatomethyl-[1,2,3]triazol-1-yl)-phenyl]-morpholine (0.1 g, 0.313 mmol), obtained in Example 34, in methanol (5 mL) was added ammouia solution (18%, 1 mL) and stirred at room temperature for 5 h. The reaction mixture was then diluted with ethyl acetate (40 mL) and the organic portion was washed successively with water, satd. NaHCO$_3$ solution and brine. Upon drying over sodium sulfate and concentration, a thick residue was obtained, which was purified by column chromatography to yield the title compound (90 mg, 90%). Mp. 192° C.

$^1$H NMR (CDCl$_3$+DMSO-d$_6$): δ 8.10 (s, 1H), 7.50–7.30 (m, 2H), 6.99 (t, J=8.8 Hz, 1H), 6.43 (br s, 2H), 4.82 (br s, 2H), 3.90–3.70 (m, 4H), 3.20–3.0 (m, 4H).

MS (m/e): 337 (M$^+$+1), 320, 278, 233, 196.

EXAMPLE 77

{1-[3-Fluoro-4-(1-oxo-1lambda*4*-thiomorpholin-4-yl)-phenyl]-1H-[1,2,3]triazol-4-ylmethyl}-thiourea

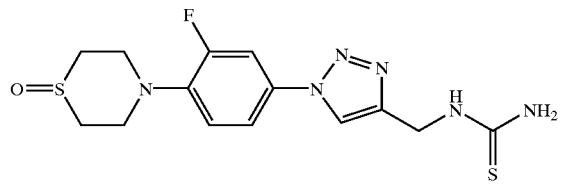

To a solution of 4-[2-fluoro-4-(4-isothiocyanatomethyl-[1,2,3]triazol-1-yl)-phenyl]-thiomorpholine-1-oxide (100 mg, 0.28 mmol), obtained in Example 37, in aqueous ammonia (18%, 3 mL) at 0° C. was added methanol (few drops) and stirred at room temperature for 0.5 h. The precipitate formed was filtered off and the solid was washed with diethyl ether to obtain the title compound (103 mg, 98%). Mp. 228–230° C.

$^1$H NMR (CDCl$_3$+DMSO-d$_6$): δ 8.60 (s, 1H), 8.05 (br s, 1H), 7.82–7.61 (m, 2H), 7.31 (t, J=8.6 Hz, 1H), 7.22–7.02 (m, 2H), 4.75 (br s, 2H), 3.71 (t, J=11.3 Hz, 2H), 3.51–3.30 (br s, 2H), 3.20–2.82 (m, 4H).

MS (m/e): 369 (M$^+$+1), 297, 271, 215, 195, 103.

EXAMPLE 78

1-{1-[3-Fluoro-4-(1-oxo-1lambda*4*-thiomorpholin-4-yl)-phenyl]-1H-[1,2,3]triazol-4-ylmethyl}-3-methyl-thiourea

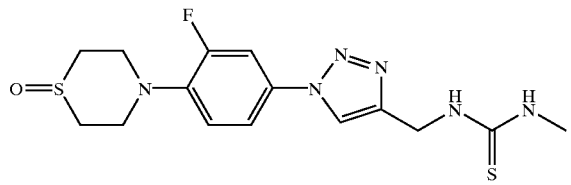

A solution of 4-[2-fluoro-4-(4-isothiocyanatomethyl-[1,2,3]triazol-1-yl)-phenyl]-thiomorpholine-]-oxide (100 mg, 0.28 mmol), obtained in Example 37, in 40% methyl amine (3 mL) was stirred at 0° C. for 30 min. The precipitate formed was filtered off and the solid was washed with diethyl ether to obtain the title compound (107 mg, 98%). Mp. 182–184° C.

$^1$H NMR (CDCl$_3$+DMSO-d$_6$): δ 8.55 (s, 1H), 7.91 (br s, 1H), 7.81–7.60 (m, 2H), 7.30 (t, J=9.0 Hz, 1H), 4.82 (brs, 2H), 3.71 (t, J=11.1 Hz, 2H), 3.52–3.31 (m, 2H), 3.22–2.80 (m, 7H).

MS (m/e): 382 (M$^+$), 380, 349, 310, 265, 103.

EXAMPLE 79

2,2-Dichloro-N-[1-(3-fluoro-4-morpholin-4-yl-phenyl)-1H-[1,2,3]triazol-4-ylmethyl]-acetamide

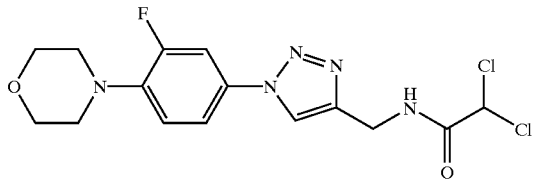

To a solution of C-[1-(3-fluoro-4-morpholin-4-yl-phenyl)-1H-[1,2,3]triazol-4-yl]-methylamine (0.2 g, 0.72 mmol), obtained in Example 17, and triethylamine (0.14 g, 1.44 mmol) in anhydrous THF (10 mL) was added dichloroacetyl chloride (0.16 g, 1.08 mmol) at 0° C. It was brought to room temperature gradually and allowed to stir for 1 h. Reaction mixture was then diluted with ethyl acetate (40 mL) and the organic portion was washed with water followed by brine and dried over sodium sulfate. Evaporation of volatiles and column chromatographic purification of the resulting material yielded the title compound as white solid (0.2 g, 70%). Mp. 190° C.

$^1$H NMR (CDCl$_3$): δ 7.96 (s, 1H), 7.60–7.20 (m, 2H), 7.05 (t, J=8.8 Hz, 1H), 5.98 (s, 1H), 4.68 (d, J=5.9 Hz, 2H), 4.01–3.80 (m, 4H), 3.25–3.05 (m, 4H).

MS (m/e): 388 (M$^+$), 354, 271, 233.

EXAMPLE 80

N-{1-[3-Fluoro-4-(1-oxo-1lambda*4*-thiomorpholin-4-yl)-phenyl]-1H-[1,2,3]triazol-4-ylmethyl}-methanesulfonamide

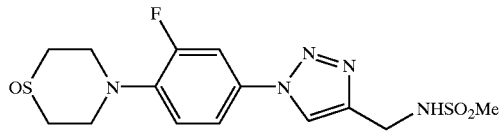

To a stirring solution of C-{1-[3-fluoro-4-(1-oxo-1lambda*4*-thiomorpholin-4-yl)-phenyl]-1H-[1,2,3]triazol-4-yl}-methylamine (100 mg, 0.32 mmol), obtained in Example 27, in dichloromethane (5 mL) at 0° C. was added triethylamine (50 mg, 0.5 mmol) followed by methanesulfonyl chloride (44 mg, 0.39 mmol) and allowed to stir at room temperature for 2 h. The reaction mixture was then absorbed on silica gel and purified by column chromatography (methanol/chloroform, 1:24) to obtain the sulfonamide derivative (121 mg, 97%). Mp. 174–176° C.

$^1$H NMR (CDCl$_3$+DMSO-d$_6$): δ 8.72 (s, 1H), 7.91–7.60 (m, 2H), 7.35 (t, J=9.3 Hz, 1H), 4.35 (d, J=5.9 Hz, 2H), 3.71 (t, J=11.3 Hz, 2H), 3.50–3.30 (m, 2H), 3.22–2.80 (m, 4H), 2.95 (s, 3H).

MS (m/e): 388 (M$^+$+1), 372, 352, 312, 180, 96.

EXAMPLE 81

N-{1-[3-fluoro-4-(4-thiomorpholinyl)phenyl]-1H-1,2,3-triazol-4-ylmethyl}-pyridine-2-thiocarboxamide

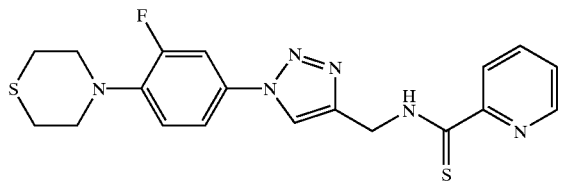

To a stirring solution of N-{1-[3-fluoro-4-(-4-thiomorpholinyl)phenyl]-1H-1,2,3-triazol-4-ylmethyl}pyridine-2-carboxamide (150 mg, 0.38 mmol), obtained in the Example 75, in toluene (10 mL) was added $P_4S_{10}$ (167 mg, 0.38 mmol) and HMDO (hexamethyl disiloxane, 61 mg, 0.38 mmmol) under argon atmosphere. The reaction mixture was refluxed for 24 h and allowed to cool to room temperature. Saturated sodium bicarbonate solution was added after the evaporation of toluene and extracted with ethyl acetate (20 mL×2). The organic portion was washed with water followed by brine and dried over sodium sulfate. Upon concentration and purification by silica gel column chromatography (ethyl acetate/pet. ether, 1:4) the title compound was obtained as white solid (97 mg, 60%). Mp. 158–160° C.

$^1$H NMR (CDCl$_3$): δ 10.7 (br s, 1H), 8.71 (d, J=8.3 Hz, 1H), 8.50 (d, J=4.4 Hz, 1H), 8.11 (s, 1H), 7.80 (t, J=6.4 Hz, 1H), 7.50–7.31 (m, 2H), 7.05 (t, J=8.8 Hz, 1H), 5.25 (d, J=5.8 Hz, 2H), 3.50–3.30 (m, 4H), 2.90–2.70 (m, 4H).

MS (m/e): 415 (M$^+$+1), 386, 349, 307, 207.

EXAMPLE 82

{1-[3-Fluoro-4-(4-oxo-piperidin-1-yl)-phenyl]-1H-[1,2,3]triazol-4-ylmethyl}-thiocarbamic acid O-methyl ester

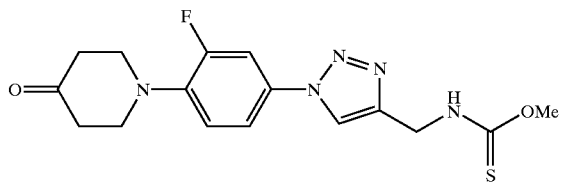

To a solution of {1-[4-(1,4-dioxa-8-aza-spiro[4.5]dec-8-yl)-3-fluoro-phenyl]-1H-[1,2,3]triazol-4-ylmethyl}-thiocarbamic acid O-methyl ester (0.18 g, 0.44 mmol), obtained in the Example 62, in THF (3 ml) was added 5% aq. HCl (3 ml) and stirred at room temperature for 24 h. The reaction mixture was neutralized with NaHCO$_3$ solution and extracted with ethyl acetate (50 ml×2). Combined organic portion was washed with water followed by brine and dried over sodium sulfate. Upon concentration and purification by silica gel column chromatography (ethyl acetate/chlorotbrnn, 1:9) the title compound was obtained as pale yellow solid (120 mg, 75%). Mp. 145–147° C.

$^1$H NMR (CDCl$_3$): δ 9.58 (br s, —NH), 8.70 & 8.61 (2 s, in the ratio of 4:1, rotamer, 1H), 7.81–7.60 (m, 2H), 7.31 (t, J=9.1 Hz, 1H), 4.72 & 4.39 (2 d, in the ratio of 4:1, rotamer, J=5.6 Hz, 2H), 3.80 & 3.91 (2 s, in the ratio of 1:4, rotamer, 3H), 3.50–3.30 (m, 4H), 2.60–2.40 (m, 4H).

MS (m/e): 364 (M$^+$+1), 332 (M$^+$—OMe), 245.

EXAMPLE 83

{1-[3-Fluoro-4-(4-hydroxyimino-piperidin-1-yl)-phenyl]-1H-[1,2,3]triazol-4-ylmethyl}-thiocarbamic acid O-methyl ester

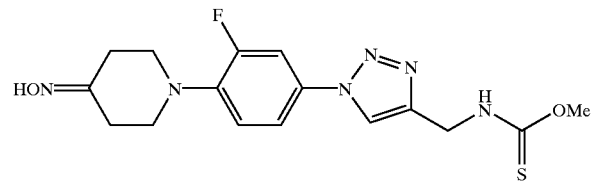

To a solution of {1-[3-Fluoro-4-(4-oxo-piperidin-1-yl)-phenyl]-1H-[1,2,3]triazol-4-ylmethyl}-thiocarbamic acid O-methyl ester (90 mg, 0.25 mmol), obtained in the Example 82, in methanol (5 ml) was added pyridine (40 mg, 0.5 mmol) followed by hydroxylamine hydrochloride (34 mg, 0.5 mmol) and refluxed for 1 h. The reaction mixture was then diluted with ethyl acetate (100 ml) and the organic portion was washed with water followed by brine and dried over sodium sulfate. Upon concentration and purification of the resulting product by silica gel column chromatography (MeOH/CHCl$_3$, 1:9), the title compound was obtained as white solid (30 mg, 32%). Mp. 141–142° C.

$^1$H NMR (CDCl$_3$): δ 8.89 (br s, 1H), 8.20 and 8.05 (2 s, in the ratio of 4:1, rotamer, 1H), 7.61–7.40 (m, 2H), 7.11 (t, J=8.6 Hz, 1H), 4.88 and 4.59 (2 d, in the ratio of 4:1, rotamer, J=5.6 Hz, 2H), 4.05 & 3.91 (2 s in the ratio of 1:4, rotaimer 3H), 3.40–3.20 (m, 4H), 2.69–2.50 (m, 4H).

MS (m/e): 379 (M$^+$+1), 347 (M$^+$—OMe), 331, 260.

EXAMPLE 84

{1-[4-(4-Dicyanomethylene-piperidin-1-yl)-3-fluoro-phenyl]-1H-[1,2,3]triazol-4-ylmethyl}-thiocarbamic acid O-methyl ester

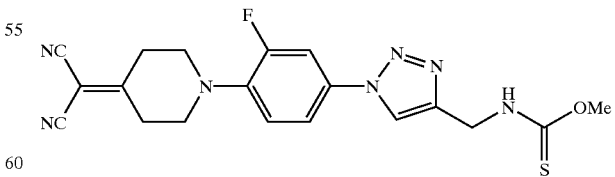

To a stirred solution of malononitrilc (22 mg, 0.33 mmol) and CsF (42 mg, 0.28 mmol) in ethanol (5 ml) was added {1-[3-Fluoro-4-(4-oxo-piperidin-1-yl)-phenyl]-1H-[1,2,3]triazol-4-ylmethyl}-thiocarbamic acid O-methyl ester (100 mg, 0.28 mmol), obtained in Example 82. The reaction mixture was allowed to stir at room temperature for 2 h and then diluted with ethyl acetate (100 ml). The organic portion was washed with water followed by brine and dried over sodium sulfate. Removal of volatiles and purification of the resulting residue by silica gel column chromatography (ethyl acetate/pet. ether, 1:1), the title compound was obtained as white solid (45 mg, 40%). Mp. 198° C.

$^1$H NMR (CDCl$_3$): δ 8.11 & 7.81 (2 s, in the ratio of 4:1, rotamer, 1H), 7.60–7.39 (m, 2H), 7.26 (t, J=8.6 Hz, 1H), 4.88 & 4.69 (2 d, in the ratio of 4:1, rotamer, J=5.6 Hz, 2H), 4.11 & 4.02 (2 s, in the ratio of 1:4, rotamer, 31.1), 3.40 (t, J=5.4 Hz, 4H), 3.02 (t, J=5.4 Hz, 4H).

MS (m/e): 412 (M$^+$+1), 408, 380 (M$^+$—OMe), 282, 119.

EXAMPLE 85

{1-[3,5-Difluoro-4-(4-oxo-piperidin-1-yl)-phenyl]-1H-[1,2,3]triazol-4-ylmethyl}thiocarbamic acid O-methyl ester

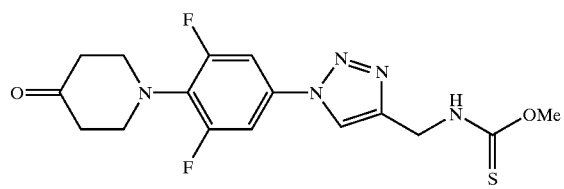

To a DMF solution (5 ml) of 1-(4-azido-2,6-difluorophenyt)-4-piperidinone (1.5 g, 5.90 mmol), obtained in Preparation 18, and diisopropylethyl amine (767 mg, 5.95 mmol) was added prop-2-ynyl-thiocarbamine acid-O-methyl ester (921 mg, 7.14 mmol) followed by the addition of cuprous iodide (1.13 g, 5.95 mmol) in portion and stirred at room temperature for 0.5 h. Saturated solution of amnionium chloride (20 ml) was added to the reaction mixture followed by the addition of ainmonium hydroxide solution. The blue colour solution was then diluted with ethylacetate (150 ml) and aqueous layer was separated. The organic layer was washed with water followed by brine and dried over sodium sulfate. Evaporation of volatiles and purification of the resulting residue through silica gel column (ethyl acetate/pet ether: 1:1) yielded the title compound (900 mg, 40%), mp 175–176° C.

$^1$H NMR (CDCl$_3$): δ 9.69 (bs, 1H, D$_2$O exchangeable), 8.74 & 8.70 (2s, 1H, rotamers in a ratio of 4:1), 7.75 (d, J=9.2 Hz, 2H), 4.73 & 4.44 (2d, J=5.3 Hz, 2H, rotamers in a ratio of 4:1), 3.95 & 3.88 (2s, 3H, rotamers in a ratio of 1:4), 3.58–3.40 (m, 4H), 2.57–2.41 (m, 4H).

MS (m/e): 382 (M$^+$+1), 350 (M$^+$—OMe), 334, 318, 293, 265.

IR (cm$^{-1}$): 3289, 3127, 1707, 1516.

In vitro Data

Minimum Inhibiton Concentrations (MICs) were determined by broth microdilution technique as per the guidelines prescribed om the fifth edition of Approved Standards, NCCLS document M7-A5 Vol 20—No 2, 2000 Villinova, Pa.

Initial stock solution of the test compound was prepared in DMSO. Subsequent two fold dilutions were carried out in sterile Mueller Hinton Broth (Difco) (MHB).

Frozen cultures stocks were inoculated into 50 mL sterile MHB in 250 mL Erlyn Meyer flasks.

Composition of MHB is as follows:

Beef Extract Powder—2.0 g/liter

Acid Digest of Casein—17.5 g/liter

Soluble Starch—1.5 g/liter

Final pH 7.3±0.1

Flasks were incubated for 4 to 5 h at 35° C. on a rotary shaker at 150 rpm. Inoculum was prepared by diluting the culture in sterile MHB to obtain a turbidity of 0.5 McFarland standard. This corresponds to 1–2×10$^8$ CFU/mL. The stock was further diluted in sterile broth to obtain 1–2×10$^6$ CFU/mL. 50 µl of the above diluted inoculum was added from 1–10 wells. The plates were incubated overnight at 37° C.

MIC is read as the lowest concentration of the compound that completely inhibits growth of the organism in the microdilution wells as detected by the unaided eye.

| Organism | Culture No. | DRCC No. |
|---|---|---|
| Staphylococcus aureus | ATCC 33591 | 019 |
| Staphylococcus aureus | ATCC 49951 | 213 |
| Staphylococcus aureus | ATCC 29213 | 035 |
| Enterococcus faecalis | ATCC 29212 | 034 |
| Enterococcus faecalis | NCTC 12201 | 153 |
| Enterococcus faecium | NCTC 12202 | 154 |
| Escherichia coli | ATCC 25922 | 018 |

ATCC: American Type Culture Collection, USA
NCTC: National Collections of Type Cultures, Colindale, UK
DRCC: Dr. Reddy's Culture Collection, Hyderabad, India The in vitro antibacterial activity data is showvn in TABLE 1.

TABLE 1

In vitro Activity of Compounds against Gram positive and Gram negative bacteria

Antimicrobial Screening (MIC) µg/mL

| | Staphylococcus aureus | | | Enterococcus sp | | | E coli |
|---|---|---|---|---|---|---|---|
| Example No. | 019 MRSA | 213 Smith S | 035 S | 034 S | 153 R | 154 R | 18 S |
| 51 | 1 | 1 | 1 | 2 | 1 | 2 | 32 |
| 52 | 2 | 2 | 2 | 2 | 2 | 2 | 256 |
| 54 | 2 | 2 | 4 | 4 | 4 | 4 | 32 |
| 55 | 4 | 4 | 4 | 18 | 4 | 8 | 32 |
| 56 | 1 | 1 | 2 | 2 | 2 | 8 | 32 |
| 58 | 1 | 2 | 2 | 4 | 2 | 4 | 32 |
| 59 | 2 | 2 | 4 | 8 | 8 | 8 | >32 |
| 60 | 1 | 1 | 2 | 2 | 1 | 4 | >32 |
| 61 | 2 | 2 | 4 | 2 | 2 | 8 | >32 |
| 67 | 1 | 1 | 1 | 1 | 1 | 1 | 32 |

What is claimed is:

1. A compound of formula (I)

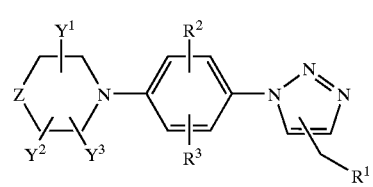

wherein R$^1$ represents halo, azido, thioalcohol, isothiocyanate, isoindole-1,3-dione, NHR$^4$ where R$^4$ represents hydrogen atom, or substituted or unsubstituted groups selected from (C$_1$–C$_{10}$)alkyl, (C$_1$–C$_{10}$)acyl, thio(C$_1$–C$_{10}$)acyl, (C$_1$–C$_{10}$)alkoxycarbonyl, (C$_3$–C$_{10}$)

cycloalkoxythiocarbonyl, $(C_2-C_{10})$alkenyloxycarbonyl, $(C_2-C_{10})$alkenylcarbonyl, heteroaryl, aryloxycarbonyl, heteroarylcarbonyl, heteroarylthiocarbonyl, $(C_1-C_{10})$alkoxythiocarbonyl, $(C_2-C_{10})$alkenyloxythiocarbonyl, aryloxythiocarbonyl, —C(=O)—C(=O)—$(C_1-C_{10})$alkyl, —C(=O)—C(=O)-aryl, —C(=O)—C(=O)—$(C_1-C_{10})$alkoxy, —C(=O)—C(=O)-aryloxy, —C(=O)—C(=S)—$(C_1-C_{10})$alkyl, —C(=O)—C(=S)-aryl, —C(=S)—S—$(C_1-C_{10})$alkyl, —C(=S)—NH$_2$, —C(=S)—NH—$(C_1-C_{10})$alkyl, —C(=S)—N—$((C_1-C_{10})$alkyl$)_2$, —C(=S)—NH—$(C_2-C_{10})$alkenyl, —C(=S)—C(=O)—$(C_1-C_{10})$alkoxy, —C(=S)—C(=O)-aryloxy, —C(=S)—O—C(=O)—$(C_1-C_{10})$alkyl, —C(=S)—C(=S)—$(C_1-C_{10})$alkyl, —C(=S)—C(=S)-aryl, —C(=S)—NH—C(=O)-aryl, —C(=S)—NH-aralkyl, —C(=S)—NH-heteroaralkyl, —C(=NH)—NH$_2$, —C(=NH)—$(C_1-C_{10})$alkyl, —C(=NH)-aryl, —S(O)$_2$$(C_1-C_{10})$alkyl, —S(O)$_2$aryl, thiomorpholinylthiocarbonyl, pyrrolidinylthiocarbonyl or —C(=S)—N(R'R''), where R' and R'' together form a substituted or unsubstituted 5 or 6 member heterocycle ring containing nitrogen and optionally having one or two additional hetero atoms selected from O, S or N; OR$^5$ where R$^5$ represents hydrogen, substituted or unstubstituted groups selected from $(C_1-C_{10})$acyl, heteroaryl, S(O)$_2$$(C_1-C_{10})$alkyl, S(O)$_2$aryl or —C(=S)—S—$(C_1-C_{10})$alkyl; N(R$^6$)$_2$, where —(R$^6$)$_2$ together represent a substituted or unsubstituted 5 or 6 member heterocycle ring containing nitrogen and optionally having one or two additional hetero atoms selected from O, S or N; R$^2$ and R$^3$ are the same or different and independently represent hydrogen, halogen atom, substituted or unsubstituted $(C_1-C_{10})$alkyl group, halo$(C_1-C_{10})$alkyl, cyano, nitro, SR$^a$, NR$^a$, or OR$^a$ where R$^a$ represents substituted or unsubstituted $(C_1-C_{10})$alkyl group; Z represents S, S(O)$_n$ where n represents 1–2, —S=NR, or —S(=O)=NR, wherein R represents hydrogen or substituted or unsubstituted $(C_1-C_{10})$alkyl; Y$^1$, Y$^2$ and Y$^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of Y$^1$, Y$^2$ or Y$^3$ represent =O, =S, substituted or unsubstituted =NOH; or

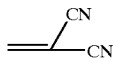

group; its tautomeric forms, its stereoisomers, its polymorphs, it rotamers, its pharmaceutically acceptable salts or its pharmaceutically acceptable solvates.

2. The compound as claimed in claim 1, wherein a 5 or 6 member heterocyclic ring formed by R' and R'' and/or heterocyclic ring formed by —(R$^6$)$_2$ is selected from the group consisting of pyrrolidinyl, pyrrolyl, morpholinyl, thiomorpholinyl, benzothiazolyl, benzoimidazolyl, pyridinyl, pyridazinyl, pyrimidinyl and pyrazinyl.

3. The compound as claimed in claim 1, wherein when one or more of R$^4$, or the group consisting of heterocycle formed by R' and R'' or the heterocycle formed by —(R$^6$)$_2$ are substituted, the substituent is selected from the groud consisting of halogen atom, hydroxy, amino, cyano, nitro, $(C_1-C_{10})$alkyl, hydroxy$(C_1-C_{10})$alkyl, $(C_1-C_{10})$alkoxy, =O, =S, aryl, hydroxyaryl, pyridyl, mono$(C_1-C_{10})$alkylamino, di$(C_1-C_{10})$alkylamino, $(C_1-C_{10})$alkoxyaryl, $(C_1-C_{10})$alkoxycarbonyl, carboxylic acid CONH$_2$, CONHMe, CONMe$_2$, CONHEt, CONEt$_2$, CONHPh, COOCH$_3$, COOC$_2$H$_5$ and COOC$_3$H$_7$.

4. The compound as claimed in claim 1, wherein when one or more of R2, R$^3$, R$^5$, or R$^a$ are substituted, the substituent(s) is selected from the group consisting of hydroxy, halogen, nitro, amino, $(C_1-C_{10})$alkyl, $(C_1-C_{10})$alkoxy, =O, =S, cyano group, carboxylic acid or CONH$_2$, CONHMe, CONMe$_2$, CONHEt, CONEt$_2$, CONHPh, COOCH$_3$, COOC$_2$H$_5$ and COOC$_3$H$_7$.

5. The compound as claimed in claim 1, wherein when one or more of Y$^1$, Y$^2$ or Y$^3$ are substituted, the substituent (s) is selected from the group consisting of hydroxy, nitro, cyano, amino, tert-butyldimethylsilyloxy, halogen atom, $(C_1-C_6)$alkyl, $(C_1-C_6)$alkoxy, $(C_3-C_6)$cycloalkyl, aryl, benzyloxy, acyl and acyloxy group.

6. The compound of the formula (I) as claimed in claim 1, selected from the group consisting of:

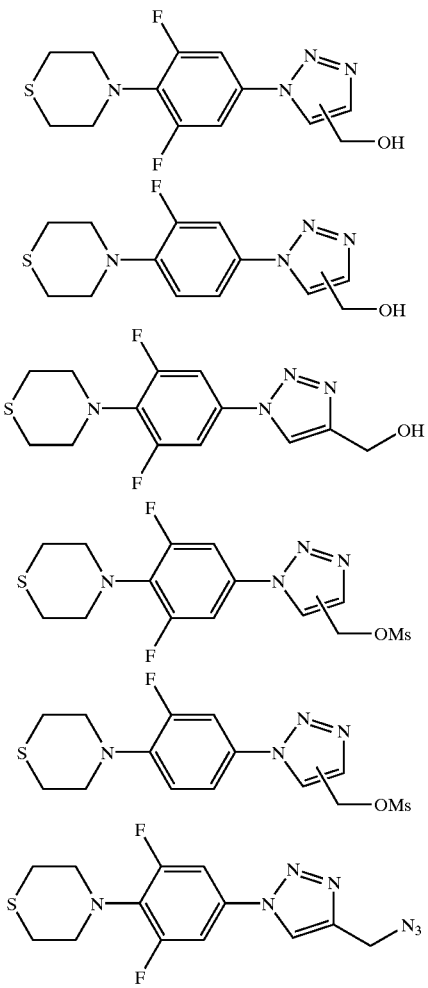

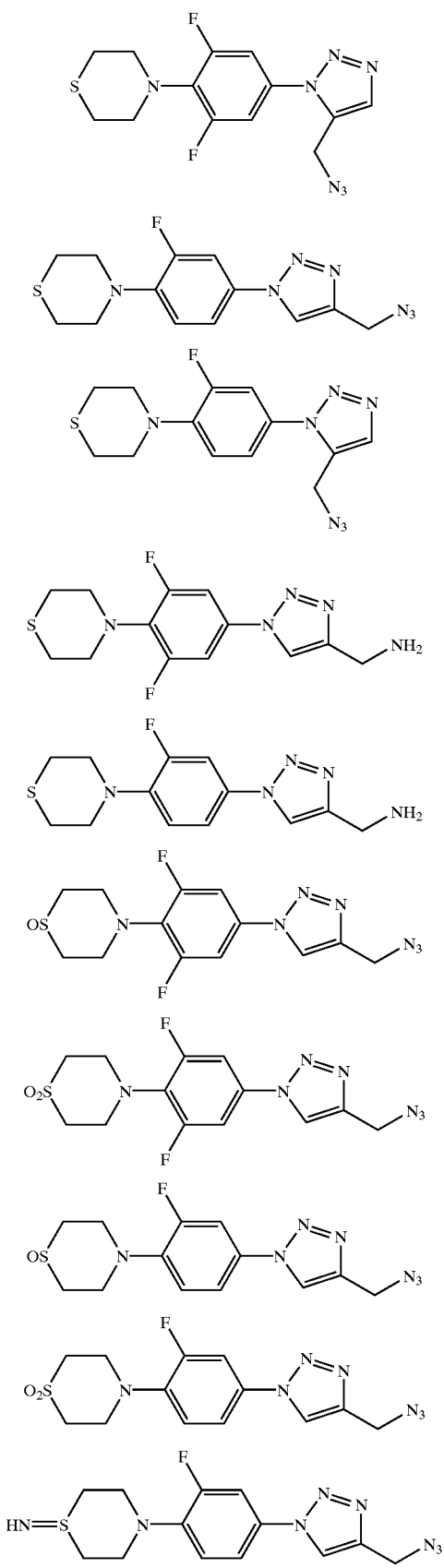
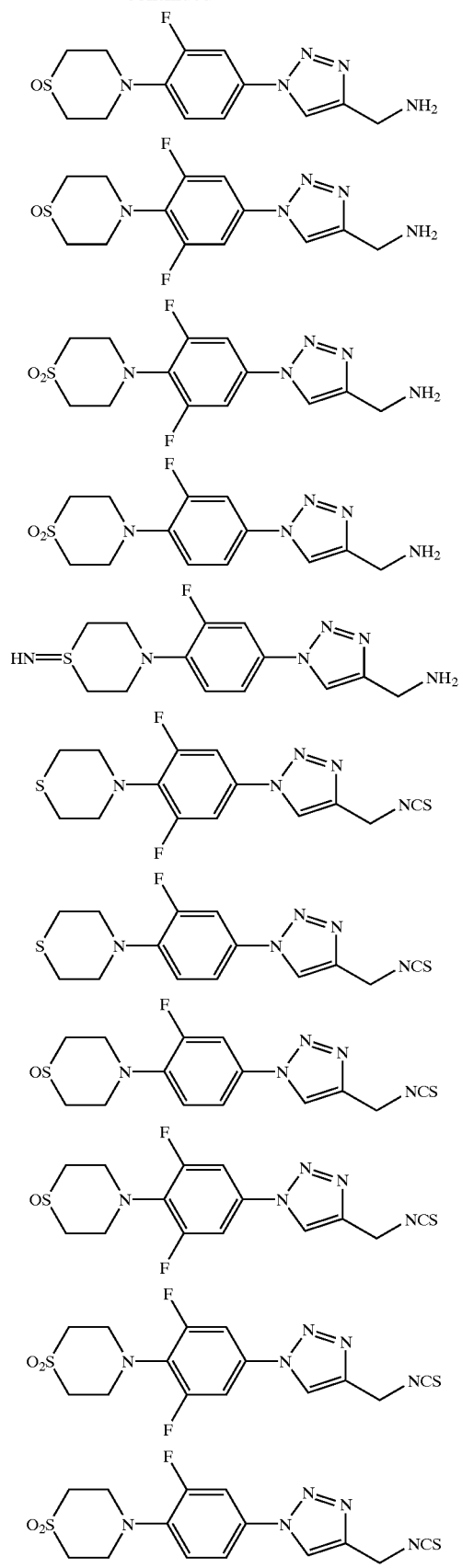

-continued
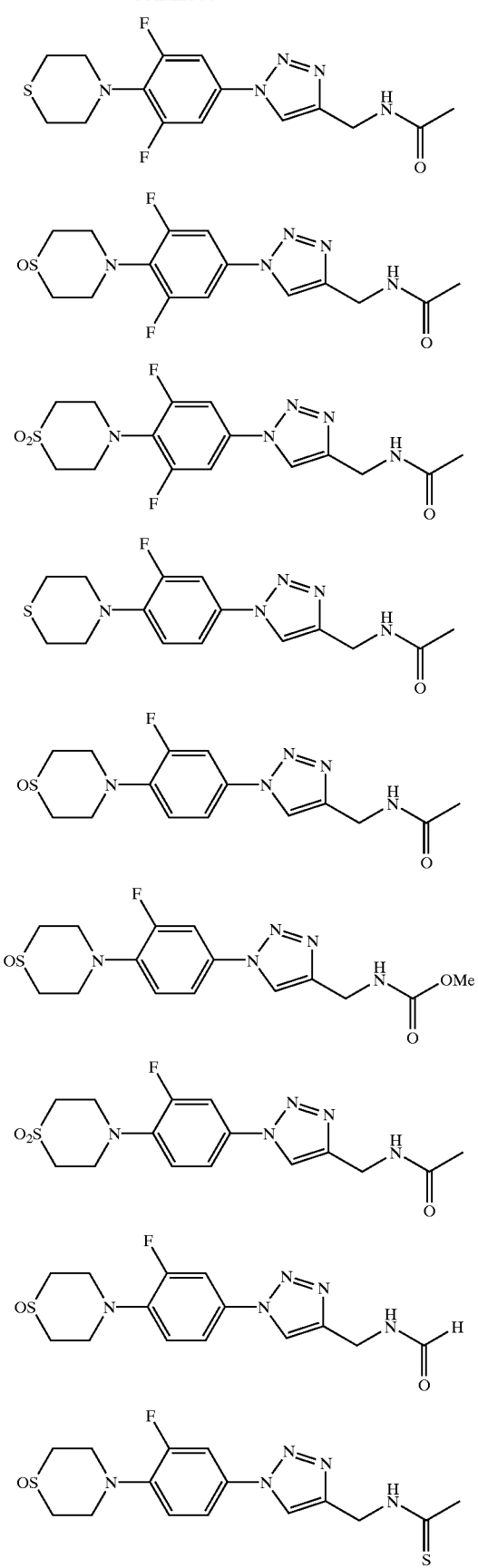
-continued
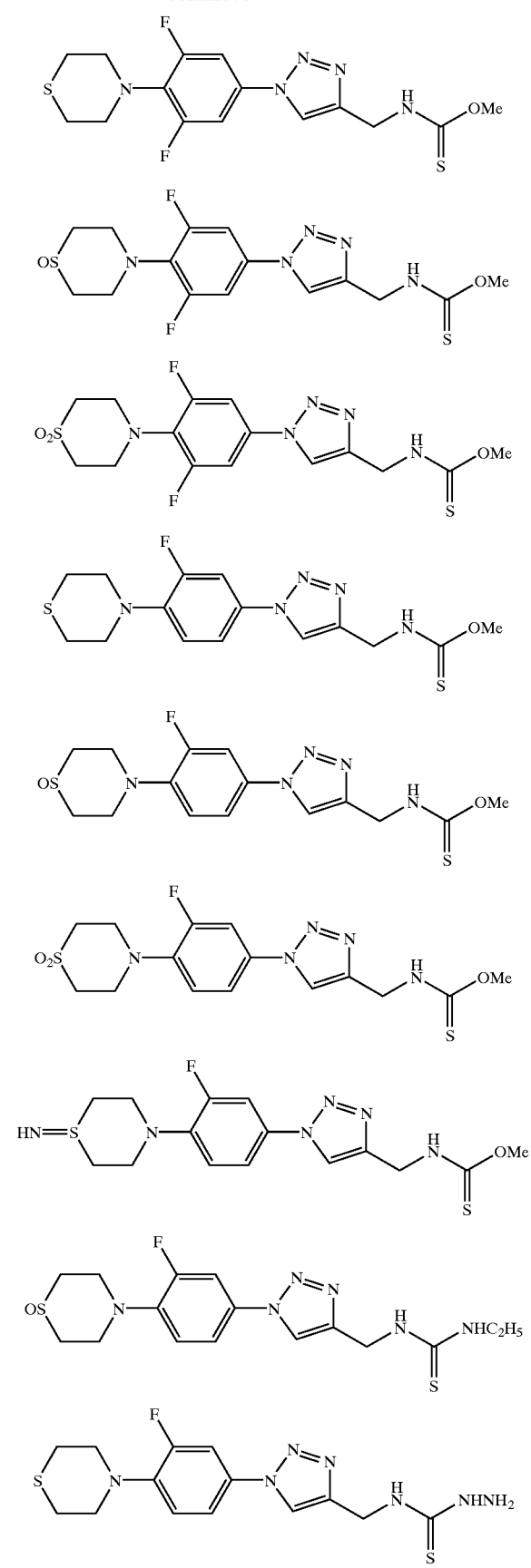

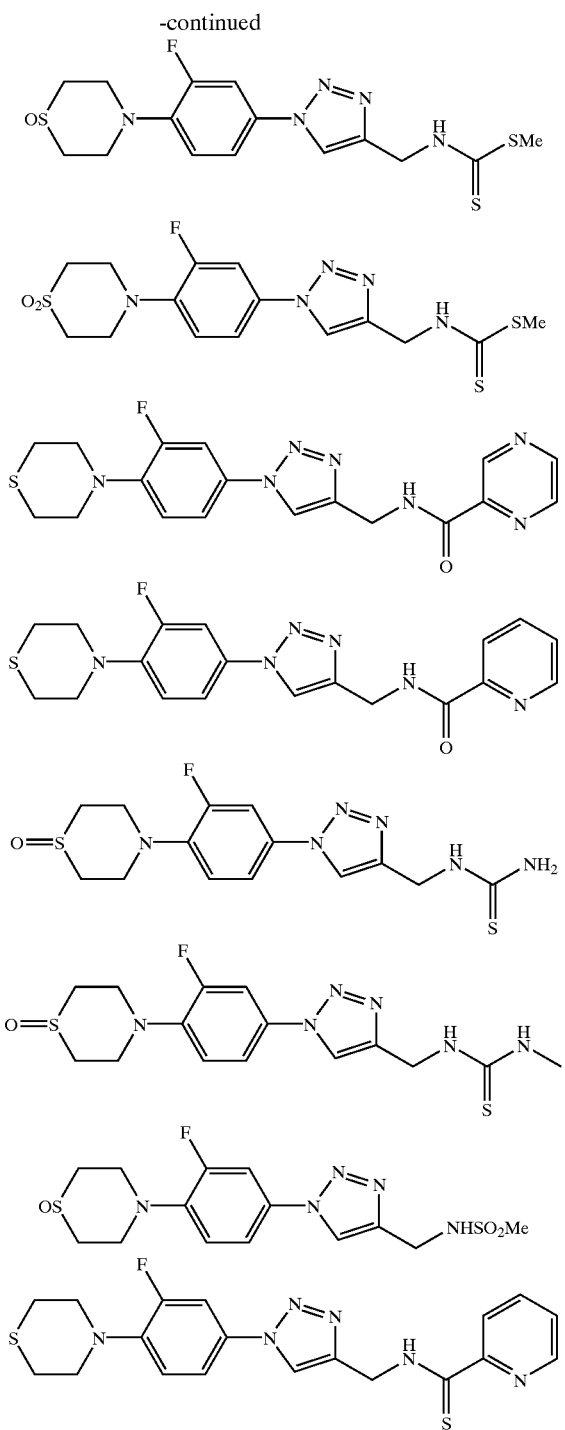

or a pharmaceutically acceptable salt thereof.

7. The compound of formula (I), as claimed in claim 1 or 6, wherein the pharmaceutically acceptable salt is selected from the group consisting of Li, Na, K, Ca, Mg, Fe, Cu, Zn, Mn; salts of organic bases, chiral bases, natural amino acids, unnatural amino acids, substituted amino acids, guanidine, substituted guanidine salts; ammonium, substituted ammonium salts, aluminum salts and acid addition salts.

8. The compound of compound of formula (I), as claimed in claim 7, wherein the salt of the organic base is selected from the group consisting of N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, and spermidine.

9. The compound of formula (I) as claimed in claim 7, wherein the salt of the chiral base is selected from the group consisting of alkylphenylamine, glycinol, and phenyl glycinol.

10. The compound of formula (I) as claimed in claim 7, wherein the salt of the natural amino acid is selected from the group consisting of glycine, alanine, valine, leucine, isoleucine, norleucine, tyrosine, cystine, cysteine, methionine, proline, hydroxy proline, histidine, ornithine, lysine, arginine, serine, threonine, and phenylalanine.

11. The compound of formula (I), as claimed in claim 7, wherein the salt of the unnatural amino acid is selected from the group consisting of D-isomers or the salt is a substituted guanidine wherein the substituent(s) is selected from the group consisting of nitro, amino, alkyl, alkenyl and alkynyl.

12. A compound of formula (I) as claimed in claim 7, wherein the acid addition salt is selected from the group consisting of sulphates, nitrates, phosphates, perchlorates, borates, halides, acetates, tartrates, maleates, citrates, succinates, palmoates, methanesulphonates, benzoates, salicylates, hydroxynaphthoates, benzenesulfonates, ascorbates, glycerophosphates, and ketoglutarates.

13. A process for the preparation of the compound of formula (I)

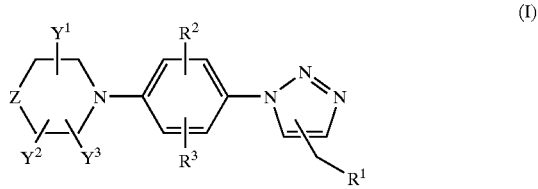

(I)

where $R^1$ represents azido group; $R^2$ and $R^3$ are the same or different and independently represent hydrogen, halogen atom, substituted or unsubstituted $(C_1-C_{10})$alkyl group, halo $(C_1-C_{10})$alkyl, cyano, nitro, $SR^a$, $NR^a$, or $OR^a$ where $R^a$ represents substituted or unsubstituted $(C_1-C_{10})$alkyl group; Z represents S, —S(O)$_n$ where n represents 1–2, —S=NR, or S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

group; its tautomeric forms, it rotamers, its stereoisomers, its polymorphs, its pharmaceutically acceptable salts or its pharmaceutically acceptable solvates, which comprises:

(a) (i) reacting the compound of formula (Ia)

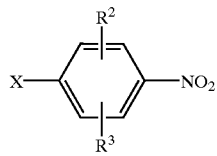
(Ia)

where X represents halogen atom; $R^2$ and $R^3$ are as defined above, with a compound of formula (Ib)

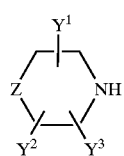
(Ib)

where Z, $Y^1$, $Y^2$ and $Y^3$ are as defined above, to produce a compound of formula (Ic)

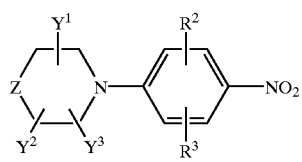
(Ic)

where Z, $Y^1$, $Y^2$, $Y^3$, $R^2$ and $R^3$ are as defined above, (ii) reducing the compound of formula (Ic) by using reducing agent to a compound of formula (Id)

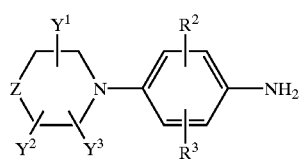
(Id)

where Z, $Y^1$, $Y^2$, $Y^3$, $R^2$ and $R^3$ are as defined above, (iii) converting the compound of formula (Id) to a compound of formula (Ie)

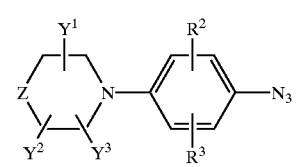
(Ie)

where Z, $Y^1$, $Y^2$, $Y^3$, $R^2$ and $R^3$ are as defined above, (iv) converting the compound of formula (Ie), to a compound of formula (If)

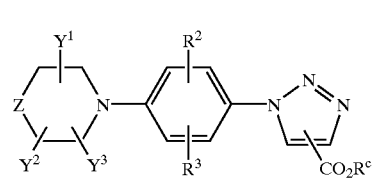
(If)

where $R^c$ represents substituted or unsubstituted $(C_1-C_{10})$alkyl group; Z, $Y^1$, $Y^2$, $Y^3$, $R^2$ and $R^3$ are as defined above, (v) reducing the compound of formula (If), to obtain a compound of formula (I)

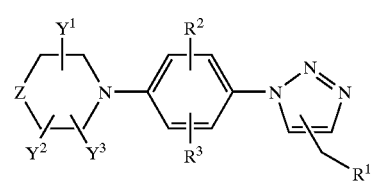
(I)

where $R^1$ represents hydroxy group; and Z, $Y^1$, $Y^2$, $Y^3$, $R^2$ and $R^3$ are as defined above, (vi) converting the compound of formula (I), where $R^1$ represents hydroxy group, to a compound of formula (I), where $R^1$ represents $OR^5$ wherein $R^5$ represents substituted or unsubstituted $S(O)_2(C_1-C_{10})$alkyl or $S(O)_2$aryl group and all other symbols are as defined above and (vii) converting the compound of formula (I) where $R^1$ represents $OR^5$ wherein $R^5$ represents substituted or unsubstituted $S(O)_2(C_1-C_{10})$alkyl or $S(O)_2$aryl group, to a compound of formula (I) where $R^1$ represents azido group and all other symbols are as defined above or (b) (i) converting the compound of formula (Ie),

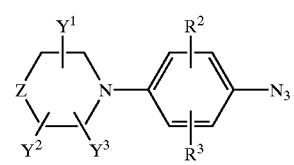
(Ie)

where Z, $Y^1$, $Y^2$, $Y^3$, $R^2$ and $R^3$ are as defined above, to a compound of formula (I)

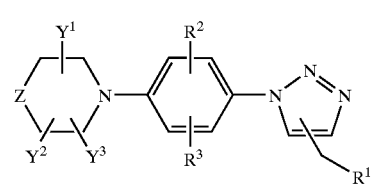
(I)

where $R^1$ represents hydroxy; Z, $Y^1$, $Y^2$, $Y^3$, $R^2$ and $R^3$ are as defined above and (ii) reacting the compound of formula (I) where $R^1$ represents hydroxy group, with MsCl, triethylamine and sodium azide to a give a compound of formula (I)

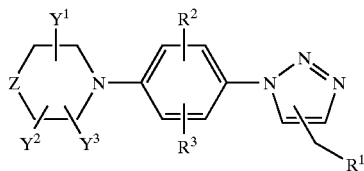

(I)

where R¹ represents azido; Z, Y¹, Y², Y³, R² and R³ are as defined above or (c) (i) converting the compound of formula (Ie)

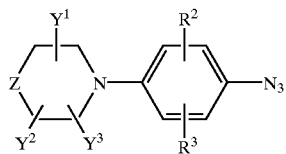

(Ie)

where Z, Y¹, Y², Y³, R² and R³ are as defined above, to a compound of formula (I)

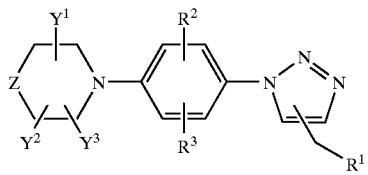

where R¹ represents halogen atom; and Z, Y¹, Y², Y³, R² and R³ are as defined above and (ii) converting the compound of formula (I) where R¹ represents halogen atom, to a compound of formula (I), wherein R¹ represents azido group.

14. A process for the preparation of compound of formula (I)

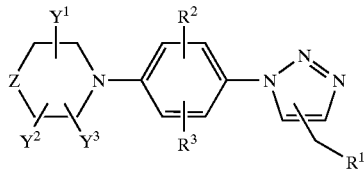

(I)

where R¹ represents azido group, R² and R³ are same or different and independently represent hydrogen, halogen atom, substituted or unsubstituted ($C_1$–$C_{10}$alkyl group, halo ($C_1$–$C_{10}$)alkyl, cyano, nitro, $SR^a$, $NR^a$, or $OR^a$ where $R^a$ represents substituted or unsubstituted ($C_1$–$C_{10}$)alkyl group; Z represents —S(O)$_n$, where n represents 1 or 2; Y¹, Y² and Y³ are the same or different and independently represent hydrogen, halogen, cyano, nitro, formyl, hydroxy, amino or substituted or unsubstituted groups selected from ($C_1$–$C_{10}$) alkyl, hydroxy($C_1$–$C_{10}$)alkyl, ($C_1$–$C_{10}$)alkoxy($C_1$–$C_{10}$) alkyl, ($C_1$–$C_{10}$)alkoxycarbonyl, carboxy($C_1$–$C_{10}$)alkyl, ($C_1$–$C_{10}$)alkylsulfonyl, ($C_1$–$C_{10}$)alkylcarbonylamino ($C_1$–$C_{10}$)alkyl, arylcarbonylamino($C_1$–$C_{10}$)alkyl, ($C_1$–$C_{10}$) alkylcarbonyloxy($C_1$–$C_{10}$)alkyl, amino($C_1$–$C_{10}$)alkyl, mono($C_1$–$C_{10}$)alkylamino, di($C_1$–$C_{10}$)alkylamino, arylamino, ($C_1$–$C_{10}$)alkoxy, aryl, aryloxy, aralkyl, heteroaryl, heteroaralkyl, heterocyclyl or heterocycloalkyl;

or any one or two of Y¹, Y² or Y³ represent =O, =S, substituted or unsubstituted =NOH; or

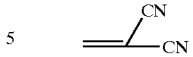

group; its tautomeric forms, its regioisomers, it rotamers, its stereoisomers, its polymorphs, its pharmaceutically acceptable salts or its pharmaceutically acceptable solvates, which comprises: oxidizing the compound of formula (I), where R¹ represents azido group; Z represents S, and all other symbols are as defined above, by using m-chloroperoxybenzoic acid (m-CPBA) or hydrogen peroxide.

15. A process for the preparation of compound of formula (I)

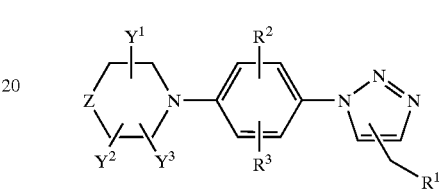

(I)

R¹ represents NHR⁴ wherein R⁴ represents hydrogen atom; R² and R³ are the same or different and independently represent hydrogen, halogen atom, substituted or unsubstituted ($C_1$–$C_{10}$)alkyl group, halo($C_1$–$C_{10}$)alkyl, cyano, nitro, $SR^a$, $NR^a$, or $OR^a$ where $R^a$ represents substituted or unsubstituted ($C_1$–$C_{10}$)alkyl group; Z represents S, S(O)$_n$ where n represents 1-2, —S=NR, or —S(=O)=NR wherein R represents hydrogen or substituted or unsubstituted ($C_1$–$C_{10}$)alkyl; Y¹, Y² and Y³ are the same or different and independently represent hydrogen, halogen, cyano, nitro, formyl, hydroxy, amino or substituted or unsubstituted groups selected from ($C_1$–$C_{10}$)alkyl, hydroxy($C_1$–$C_{10}$)alkyl, ($C_1$–$C_{10}$)alkoxy($C_1$–$C_{10}$)alkyl, ($C_1$–$C_{10}$)alkoxycarbonyl, carboxy($C_1$–$C_{10}$)alkyl, ($C_1$–$C_{10}$)alkylsulfonyl, ($C_1$–$C_{10}$) alkylcarbonylamino($C_1$–$C_{10}$)alkyl, arylcarbonylamino ($C_1$–$C_{10}$)alkyl, ($C_1$–$C_{10}$)alkylcarbonyloxy($C_1$–$C_{10}$)alkyl, amino($C_1$–$C_{10}$)alkyl, mono($C_1$–$C_{10}$)alkylamino, di($C_1$–$C_{10}$) alkylamino, arylamino, ($C_1$–$C_{10}$)alkoxy, aryl, aryloxy, aralkyl, heteroaryl, heteroaralkyl, heterocyclyl or heterocycloalkyl; or any one or two of Y¹, Y² or Y³ represent =O, =S, substituted or unsubstituted =NOH; or

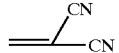

group; its tautomeric forms, it rotamers, its stereoisomers, its polymorphs, its pharmaceutically acceptable salts or its pharmaceutically acceptable solvates, which comprises:

(a) (i) converting the compound of formula (If)

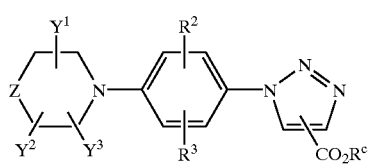

(If)

where $R^c$ represents substituted or unsubstituted ($C_1$–$C_{10}$)alkyl group; and Z, Y¹, Y², Y³, R² and R³ are as defined above, to a compound of formula (Ig)

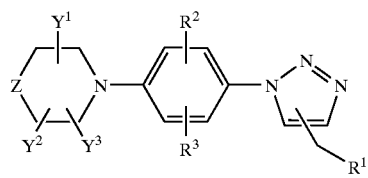
(Ig)

where Z, $Y^1$, $Y^2$, $Y^3$, $R^2$ and $R^3$ are as defined above and (ii) reducing the compound of formula (Ig), to produce a compound of formula (I) where $R^1$ represents $NHR^4$ wherein $R^4$ represents hydrogen atom and all other symbols are as defined above or (b) (i) reducing the compound of formula (I) wherein $R^1$ represents azido group, to a compound of formula (I)

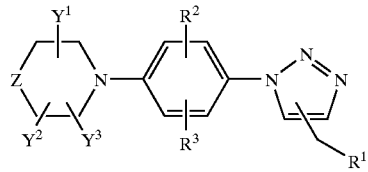
(I)

where $R^1$ represents $NHR^4$ wherein $R^4$ represents hydrogen atom; $Y^1$, $Y^2$, $Y^3$, $R^2$, $R^3$ and Z are as defined above.

16. A process for the preparation of compound of formula (I)

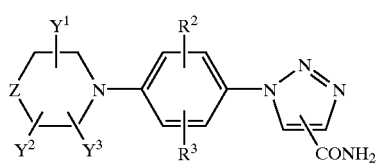
(I)

$R^1$ represents hydroxy group; $R^2$ and $R^3$ are the same or different and independently represent hydrogen, halogen atom, substituted or unsubstituted $(C_1-C_{10})$alkyl group, halo $(C_1-C_{10})$alkyl, cyano, nitro, $SR^a$, $NR^a$, or $OR^a$ where $R^a$ represents substituted or unsubstituted $(C_1-C_{10})$alkyl group; Z represents S, $S(O)_n$ where n represents 1–2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

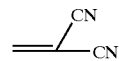

group; its tautomeric forms, it rotamers, its stereoisomers, its polymorphs, its pharmaceutically acceptable salts or its pharmaceutically acceptable solvates, which comprises:

(a) (i) reacting the compound of formula (Ia)

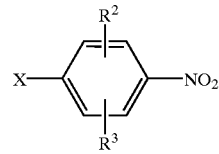
(Ia)

where X represents halogen atom; $R^2$ and $R^3$ are as defined above, with a compound of formula (Ib)

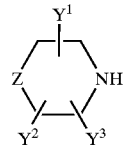
(Ib)

where Z, $Y^1$, $Y^2$ and $Y^3$ are as defined above, to produce a compound of formula (Ic)

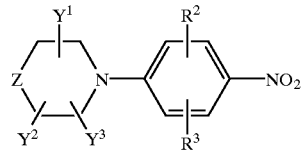
(Ic)

where Z, $Y^1$, $Y^2$, $Y^3$, $R^2$ and $R^3$ are as defined above, (ii) reducing the compund of formula (Ic) by using reducing agent to a compound of formula (Id)

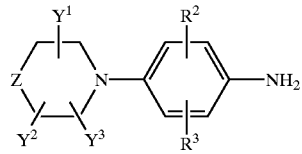
(Id)

where Z, $Y^1$, $Y^2$, $Y^3$, $R^2$ and $R^3$ are as defined above, (iii) converting the compound of formula (Id) to a compound of formula (Ie)

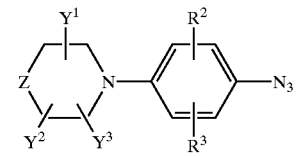
(Ie)

where Z, $Y^1$, $Y^2$, $Y^3$, $R^2$ and $R^3$ are as defined above, (iv) converting the compound of formula (Ie), to a compound of formula (If)

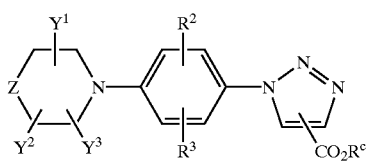
(If)

where $R^c$ represents $(C_1-C_{10})$alkyl group; Z, $Y^1$, $Y^2$, $Y^3$, $R^2$ and $R^3$ are as defined above and (v) reducing the compound of formula (If), to give a compound of formula (I)

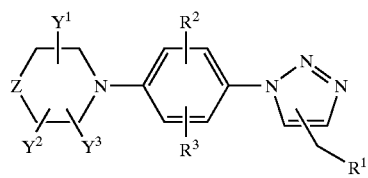
(I)

where $R^1$ represents hydroxy group; Z, $Y^1$, $Y^2$, $Y^3$, $R^2$ and $R^3$ are as defined above, or (b) (i) converting the compound of formula (Ie),

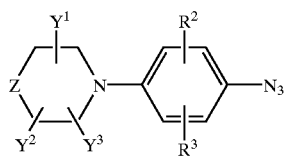
(Ie)

where Z, $Y^1$, $Y^2$, $Y^3$, $R^2$ and $R^3$ are as defined above, to a compound of formula (I)

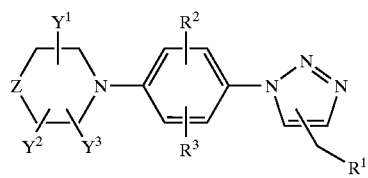
(I)

where $R^1$ represents hydroxy; Z, $Y^1$, $Y^2$, $Y^3$, $R^2$ and $R^3$ are as defined above, or (c) (i) converting the compound of formula (Ie),

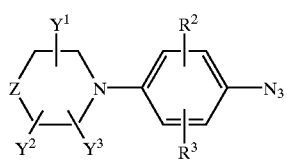
(Ie)

where Z, $Y^1$, $Y^2$, $Y^3$, $R^2$ and $R^3$ are as defined above, to a compound of formula (I),

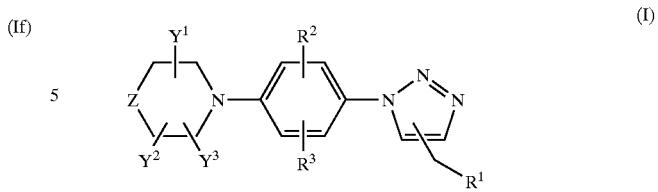
(I)

where $R^1$ represents $OR^5$ wherein $R^5$ represents substituted or unsubstituted $(C_1-C_{10})$acyl group, and all other symbols are as defined above and (ii) hydrolysis of the compound of formula (I) where $R^1$ represents $OR^5$ wherein $R^5$ is as defined above, to a compound of formula (I), where $R^1$ represents hydroxy group and all other symbols are as defined above.

17. A process for the preparation of compound of formula (I)

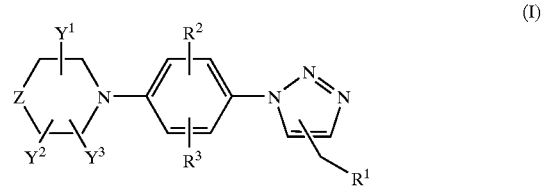
(I)

where $R^1$ represents $NHR^4$, wherein $R^4$ represents substituted or unsubstituted acetyl group; $R^2$ and $R^3$ may be same or different and independently represent hydrogen, halogen atom, substituted or unsubstituted $(C_1-C_{10})$alkyl group, halo $(C_1-C_{10})$alkyl, cyano, nitro, $SR^a$, $NR^a$, or $OR^a$ where $R^a$ represents substituted or unsubstituted $(C_1-C_{10})$alkyl group; Z represents S, $S(O)_n$ where n represents 1–2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH or

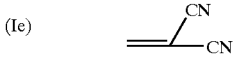

group; its tautomeric forms, it rotamers, its stereoisomers, its polymorphs, its pharmaceutically acceptable salts or its pharmaceutically acceptable solvates, which comprises: reacting the compound of formula (I) where $R^1$ represents azido group and all other symbols are as defined above, with thiolacetic acid.

18. A process for the preparation of compound of formula (I)

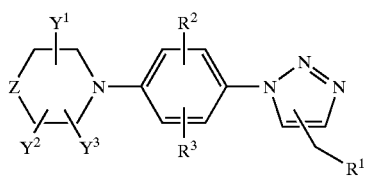
(I)

where $R^1$ represents $NHR^4$, where $R^4$ represents substituted or unsubstituted —C(=S)—$R^{4a}$, wherein $R^{4a}$ represents $(C_1-C_{10})$alkyl, halo$(C_1-C_{10})$alkyl, aryl, heteroaryl, —C(=O)—$(C_1-C_{10})$alkoxy, —C(=O)-aryloxy, —C(=S)—$(C_1-C_{10})$alkyl or —C(=S)-aryl; $R^2$ and $R^3$ are the same or different and independently represent hydrogen, halogen atom, substituted or unsubstituted $(C_1-C_{10})$alkyl group, halo$(C_1-C_{10})$alkyl, cyano, nitro, $SR^a$, $NR^a$, or $OR^a$ where $R^a$ represents substituted or unsubstituted $(C_1-C_{10})$ alkyl group; Z represents S, $S(O)_n$ where n represents 1–2, —S=NR, —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$ alkyl, hydroxy$(C_1-C_{10})$alkyl, $(C_1-C_{10})$alkoxy$(C_1-C_{10})$ alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino $(C_1-C_{10})$alkyl, arylcarbonylamino$(C_1-C_{10})$alkyl, $(C_1-C_{10})$ alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

group; its tautomeric forms, it rotamers, its stereoisomers, its polymorphs, its pharmaceutically acceptable salts or its pharmaceutically acceptable solvates, which comprises: reacting the compound of formula (I) where $R^1$ represents $NHR^4$, where $R^4$ represents substituted or unsubstituted —C(=O)—$R^{4a}$, wherein $R^{4a}$ represents $(C_1-C_{10})$alkyl, halo$(C_1-C_{10})$alkyl, aryl, heteroaryl, —C(=O)—$(C_1-C_{10})$ alkoxy, —C(=O)-aryloxy, —C(=S)—$(C_1-C_{10})$alkyl or —C(=S)-aryl and all other symbols are as defined above, with a solution of amide and Lawesson's reagent (2,4-bis (methoxyphenyl)-1,3-dithia-2,4-diphosphetane-2,4-disulfide).

19. A process for the preparation of compound of formula (I)

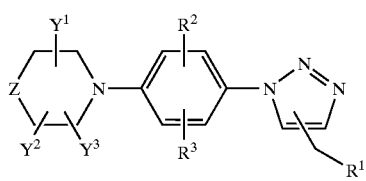
(I)

where $R^1$ represents $NHR^4$, wherein $R^4$ represents substituted or unsubstituted —C(=S)—$OR^{4b}$, wherein $R^{4b}$ represents $(C_1-C_{10})$alkyl, cyclo$(C_3-C_{10})$alkyl, aryl, $(C_2-C_{10})$ alkenyl or —(C=O)—$(C_1-C_{10})$alkyl group; $R^2$ and $R^3$ are the same or different and independently represent hydrogen, halogen atom, substituted or unsubstituted $(C_1-C_{10})$alkyl group, halo$(C_1-C_{10})$alkyl, cyano, nitro, $SR^a$, $NR^a$, or $OR^a$ where $R^a$ represents substituted or unsubstituted $(C_1-C_{10})$ alkyl group; Z represents S, $S(O)_n$ where n represents 1–2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$ alkyl, hydroxy$(C_1-C_{10})$alkyl, $(C_1-C_{10})$alkoxy$(C_1-C_{10})$ alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino $(C_1-C_{10})$alkyl, arylcarbonylamino$(C_1-C_{10})$alkyl, $(C_1-C_{10})$ alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

group; its tautomeric forms, it rotamers, its stereoisomers, its polymorphs, its pharmaceutically acceptable salts or its pharmaceutically acceptable solvates, which comprises:

(i) reacting compound of formula (I)

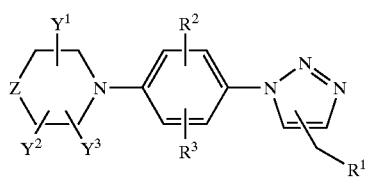
(I)

where $R^1$ represents azido group; and all other symbols are as defined above, with triphenylphosphine/water or $H_2$—Pd/C, to produce a compound of formula (I), where $R^1$ represents $NHR^4$, wherein $R^4$ represents hydrogen atom and all other symbols are as defined above, (ii) reacting compound of formula (I), where $R^1$ represents $NHR^4$, wherein $R^4$ represents hydrogen atom, with thiophosgene or carbon disulfide and chloromethylformate, to produce a compound of formula (I)

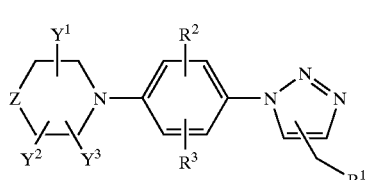
(I)

where $R^1$ represents isothiocyanate group; and all symbols are as defined above, (iii) converting compound of formula (I) where $R^1$ represents isothiocynate group, to a compound of formula (I), where $R^1$ represents $NHR^4$, wherein $R^4$ represents substituted or unsubstituted —C(=S)—$OR^{4b}$, wherein $R^{4b}$ is as defined above and all other symbols are as defined above.

20. A process for the preparation of compound of formula (I)

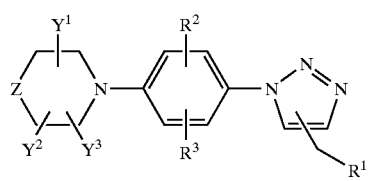

where $R^1$ represents $NHR^4$, where $R^4$ represents substituted or unsubstituted groups selected from —C(=S)—NH$_2$, —C(=S)—NH—(C$_1$–C$_{10}$)alkyl, —C(=S)—N—((C$_1$–C$_{10}$)alkyl)$_2$, —C(=S)—NH—(C$_2$–C$_{10}$)alkenyl, C(=S)—NH—C(=O)-aryl, —C(=S)—NH-aralkyl, —C(=S)—NH-heteroaralkyl or —C(=S)—N(R'R''), wherein R' and R'' groups together form a substituted or unsubstituted 5 or 6 membered cyclic ring containing nitrogen and optionally having one or two additional hetero atoms selected from O, S or N; $R^2$ and $R^3$ are the same or different and independently represent hydrogen, halogen atom, substituted or unsubstituted (C$_1$–C$_{10}$)alkyl group, halo (C$_1$–C$_{10}$)alkyl, cyano, nitro, SR$^a$, NR$^a$, or OR$^a$ where R$^a$ represents substituted or unsubstituted (C$_1$–C$_{10}$)alkyl group; Z represents S, S(O)$_n$ where n represents 1–2, —S=NR, or —S(=O)=NR wherein R represents hydrogen or substituted or unsubstituted (C$_1$–C$_{10}$)alkyl; $Y^1$, $Y^2$ and $Y^3$ are the same or different and independently represent hydrogen, halogen, cyano, nitro, formyl, hydroxy, amino or substituted or unsubstituted groups selected from (C$_1$–C$_{10}$)alkyl, hydroxy(C$_{1-10}$)alkyl, (C$_1$–C$_{10}$)alkoxy(C$_1$–C$_{10}$)alkyl, (C$_1$–C$_{10}$)alkoxycarbonyl, carboxy(C$_1$–C$_{10}$)alkyl, (C$_1$–C$_{10}$)alkylsulfonyl, (C$_1$–C$_{10}$)alkylcarbonylamino(C$_1$–C$_{10}$)alkyl, arylcarbonylamino(C$_1$–C$_{10}$)alkyl, (C$_1$–C$_{10}$)alkylcarbonyloxy(C$_1$–C$_{10}$)alkyl, amino(C$_{1-10}$)alkyl, mono(C$_{1-10}$)alkylamino, di(C$_1$–C$_{10}$)alkylamino, arylamino, (C$_1$–C$_{10}$)alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

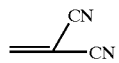

group; its tautomeric forms, it rotamers, its stereoisomers, its polymorphs, its pharmaceutically acceptable salts or its pharmaceutically acceptable solvates, which comprises: reacting a compound of formula (I) where $R^1$ represents isothiocyanate group and all other symbols are as defined above, with ammonia gas or amine.

21. A process for the preparation of compound of formula (I)

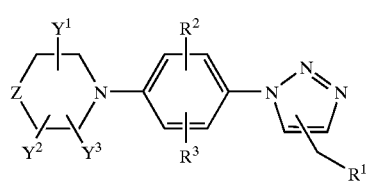

where $R^1$ represents $NHR^4$, wherein $R^4$ represents substituted or unsubstituted —C(=S)—SR$^{4c}$, wherein $R^{4c}$ represents (C$_1$–C$_{10}$)alkyl group; $R^2$ and $R^3$ are the same or different and independently represent hydrogen, halogen atom, substituted or unsubstituted (C$_1$–C$_{10}$)alkyl group, halo (C$_1$–C$_{10}$)alkyl, cyano, nitro, SR$^a$, NR$^a$, or OR$^a$ where R$^a$ represents substituted or unsubstituted (C$_1$–C$_{10}$)alkyl group; Z represents S, S(O)$_n$ where n represents 1–2, —S=NR, or —S(=O)=NR wherein R represents hydrogen or substituted or unsubstituted (C$_1$–C$_{10}$)alkyl; $Y^1$, $Y^2$ and $Y^3$ are the same or different and independently represent hydrogen, halogen, cyano, nitro, formyl, hydroxy, amino or substituted or unsubstituted groups selected from (C$_1$–C$_{10}$)alkyl, hydroxy(C$_1$–C$_{10}$)alkyl, (C$_1$–C$_{10}$)alkoxy(C$_1$–C$_{10}$)alkyl, (C$_1$–C$_{10}$)alkoxycarbonyl, carboxy(C$_1$–C$_{10}$)alkyl, (C$_1$–C$_{10}$) alkylsulfonyl, (C$_1$–C$_{10}$)alkylcarbonylamino(C$_1$–C$_{10}$)alkyl, arylcarbonylamino(C$_1$–C$_{10}$)alkyl, (C$_1$–C$_{10}$)alkylcarbonyloxy(C$_1$–C$_{10}$)alkyl, amino(C$_1$–C$_{10}$)alkyl, mono(C$_1$–C$_{10}$)alkylamino, di(C$_1$–C$_{10}$)alkylamino, arylamino, (C$_1$–C$_{10}$)alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

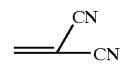

group; its tautomeric forms, it rotamers, its stereoisomers, its polymorphs, its pharmaceutically acceptable salts or its pharmaceutically acceptable solvates, which comprises: reacting the compound of formula (I), where $R^1$ represents $NHR^4$, wherein $R^4$ represents hydrogen atom and all other symbols are as defined above, with CS$_2$ and alkylhalide.

22. A process for the preparation of compound of formula (I)

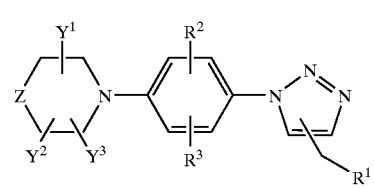

where $R^1$ represents $NHR^4$, wherein $R^4$ represents substituted or unsubstituted —C(=S)—NH—R$^{4d}$, wherein $R^{4d}$ represents C(=O)-aryl group; $R^2$ and $R^3$ are the same or different and independently represent hydrogen, halogen atom, substituted or unsubstituted (C$_1$–C$_{10}$)alkyl group, halo (C$_1$–C$_{10}$)alkyl, cyano, nitro, SR$^a$, NR$^a$ or OR$^a$ where R$^a$ represents substituted or unsubstituted (C$_1$–C$_{10}$)alkyl group; Z represents S, S(O)$_n$ where n represents 1–2, —S=NR, or —S(=O)=NR wherein R represents hydrogen or substituted or unsubstituted (C$_1$–C$_{10}$)alkyl; $Y^1$, $Y^2$ and $Y^3$ are the same or different and independently represent hydrogen, halogen, cyano, nitro, formyl, hydroxy, amino or substituted or unsubstituted groups selected from (C$_1$–C$_{10}$)alkyl, hydroxy(C$_1$–C$_{10}$)alkyl, (C$_1$–C$_{10}$)alkoxy(C$_1$–C$_{10}$)alkyl, (C$_1$–C$_{10}$)alkoxycarbonyl, carboxy(C$_1$–C$_{10}$)alkyl, (C$_1$–C$_{10}$)alkylsulfonyl, (C$_1$–C$_{10}$)alkylcarbonylamino(C$_1$–C$_{10}$)alkyl, arylcarbonylamino(C$_1$–C$_{10}$)alkyl, (C$_1$–C$_{10}$)alkylcarbonyloxy(C$_1$–C$_{10}$)alkyl, amino(C$_1$–C$_{10}$)alkyl, mono(C$_1$–C$_{10}$)alkylamino, di(C$_1$–C$_{10}$)alkylamino, arylamino, (C$_1$–C$_{10}$)alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

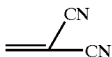

group; its tautomeric forms, it rotamers, its stereoisomers, its polymorphs, its pharmaceutically acceptable salts or its pharmaceutically acceptable solvates, which comprises: reacting the compound of formula (I), where $R^1$ represents $NHR^4$, wherein $R^4$ represents hydrogen atom and all other symbols are as defined above, with benzoylisothiocyanate.

23. A process for the preparation of compound of formula (I)

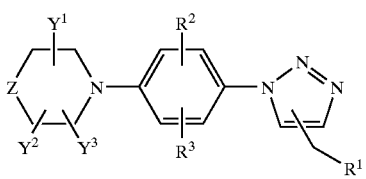

(I)

where $R^1$ represents $NHR^4$, wherein $R^4$ represents substituted or unsubstituted group selected from —C(=O)-heteroaryl; $R^2$ and $R^3$ are the same or different and independently represent hydrogen, halogen atom, substituted or unsubstituted $(C_1-C_{10})$alkyl group, halo$(C_1-C_{10})$alkyl, cyano, nitro, $SR^a$, $NR^a$ or $OR^a$ where $R^a$ represents substituted or unsubstituted $(C_1-C_{10})$alkyl group; Z represents S, $S(O)_n$ where n represents 1-2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-Cl10)$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

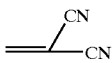

group; its tautomeric forms, it rotamers, its stereoisomers, its polymorphs, its pharmaceutically acceptable salts or its pharmaceutically acceptable solvates, which comprises: reacting the compound of formula (I), where $R^1$ represents $NHR^4$, wherein $R^4$ represents hydrogen atom and all other symbols are as defined above, with heteroaryl acid chloride.

24. A process for the preparation of compound of formula (I)

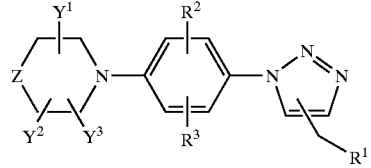

(I)

where $R^1$ represents $OR^5$, wherein $R^5$ represents substituted or unsubstituted heteroaryl or $R^1$ represents $N(R^6)_2$, wherein —$(R^6)_2$ together represent a substituted or unsubstituted 5 or 6 membered heterocycle optionally ring containing nitrogen and optionally having one or two additional hetero atoms selected from O, S or N; $R^2$ and $R^3$ are the same or different and independently represent hydrogen, halogen atom, substituted or unsubstituted $(C_1-C_{10})$alkyl group, halo$(C_1-C_{10})$alkyl, cyano, nitro, $SR^a$, $NR^a$, or $OR^a$ where $R^a$ represents substituted or unsubstituted $(C_1-C_{10})$alkyl group; Z represents S, $S(O)_n$ where n represents 1-2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

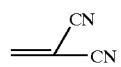

group; its tautomeric forms, it rotamers, its stereoisomers, its polymorphs, its pharmaceutically acceptable salts or its pharmaceutically acceptable solvates, which comprises: reacting the compound of formula (I), where $R^1$ represents $OR^5$, wherein $R^5$ represents substituted or unsubstituted $S(O)_2(C_1-C_{10})$alkyl or $S(O)_2$aryl group and all other symbols are as defined above, with 2-pyridinol.

25. A process for the preparation of compound of formula (I)

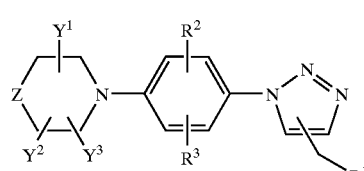

(I)

where $R^1$ represents $NHR^4$ where $R^4$ represents substituted or unsubstituted —(C=O)—$R^{4e}$ wherein $R^{4e}$ represents $(C_1-C_{10})$alkyl, $(C_1-C_{10})$alkoxy, $(C_2-C_{10})$alkenyl, halo $(C_1-C_{10})$alkyl, aryl, aryloxy, heteroaryl, $(C_2-C_{10})$ alkenyloxy, $(C_1-C_{10})$alkylcarbonyl, arylcarbonyl, aryloxycarbonyl, $(C_1-C_{10})$alkoxycarbonyl, $(C_1-C_{10})$ alkylthiocarbonyl or $(C_1-C_{10})$arylthiocarbonyl; $R^2$ and $R^3$ are the same or different and independently represent hydrogen, halogen atom, substituted or unsubstituted $(C_1-C_{10})$alkyl group, halo$(C_1-C_{10})$alkyl, cyano, nitro, $SR^a$, $NR^a$, or $OR^a$ where $R^a$ represents substituted or unsubstituted $(C_1-C_{10})$alkyl group; Z represents S, $S(O)_n$ where n represents 1–2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

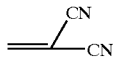

group; its tautomeric forms, it rotamers, its stereoisomers, its polymorphs, its pharmaceutically acceptable salts or its pharmaceutically acceptable solvates, which comprises: reacting the compound of formula (I), where $R^1$ represents $NHR^4$, wherein $R^4$ represents hydrogen atom and all other symbols are as defined above, with acid halide, alkylchloroformate or anhydride of acid.

26. A process for the preparation of compound of formula (I)

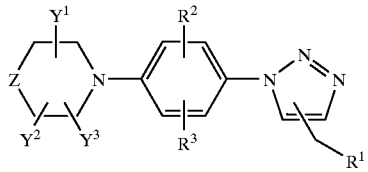

where $R^1$ represents $OR^5$, wherein $R^5$ represents substituted or unsubstituted group selected from —C(=S)—S—$(C_1-C_{10})$alkyl group; $R^2$ and $R^3$ are the same or different and independently represent hydrogen, halogen atom, substituted or unsubstituted $(C_1-C_{10})$alkyl group, halo$(C_1-C_{10})$alkyl, cyano, nitro, $SR^a$, $NR^a$, or $OR^a$ where $R^a$ represents substituted or unsubstituted $(C_1-C_{10})$alkyl group; Z represents S, $S(O)_n$ where n represents 1–2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

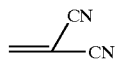

group; its tautomeric forms, it rotamers, its stereoisomers, its polymorphs, its pharmaceutically acceptable salts or its pharmaceutically acceptable solvates, which comprises: reacting the compound of formula (I), where $R^1$ represents $OR^5$, wherein $R^5$ represents hydrogen atom and all other symbols are as defined above, with $CS_2$ and alkyl halide.

27. A process for the preparation of compound of formula (I)

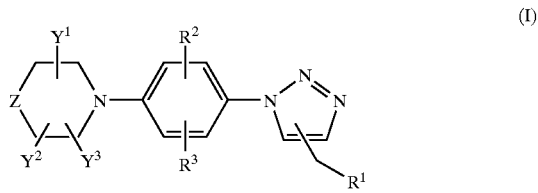

where $R^1$ represents $NHR^4$ where $R^4$ represents substituted or unsubstituted —C(=NH)—$NH_2$; $R^2$ and $R^3$ are the same or different and independently represent hydrogen, halogen atom, substituted or unsubstituted $(C_1-C_{10})$alkyl group, halo $(C_1-C_{10})$alkyl, cyano, nitro, $SR^a$, $NR^a$, or $OR^a$ where $R^a$ represents substituted or unsubstituted $(C_1-C_{10})$alkyl group; Z represents S, $S(O)_n$ where n represents 1–2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

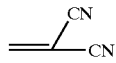

group; its tautomeric forms, it rotamers, its stereoisomers, its polymorphs, its pharmaceutically acceptable salts or its pharmaceutically acceptable solvates, which comprises:

(a) reacting a compound of formula (I), where $R^1$ represents $NHR^4$ wherein $R^4$ represents hydrogen atom and all other symbols are as defined above, with di-tert-butoxy carbonyl thiourea or (b) reacting the compound of formula (I), where $R^1$ represents $NHR^4$ wherein $R^4$ represents substituted or unsubstituted group selected from $S(O)_2(C_1-C_{10})$alkyl or $S(O)_2$aryl group and all other symbols are as defined above, with guanidine hydrochloride.

28. A process for the preparation of compound of formula (I)

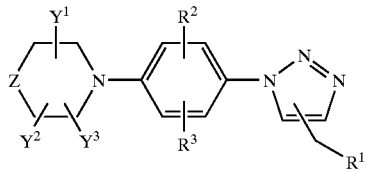

where $R^1$ represents $NHR^4$ where $R^4$ represents substituted or unsubstituted group selected from —C(=NH)—($C_1$–$C_{10}$)alkyl or —C(=NH)-aryl; $R^2$ and $R^3$ are the same or different and independently represent hydrogen, halogen atom, substituted or unsubstituted ($C_1$–$C_{10}$)alkyl group, halo ($C_1$–$C_{10}$)alkyl, cyano, nitro, $SR^a$, $NR^a$, or $OR^a$ where $R^a$ represents substituted or unsubstituted ($C_1$–$C_{10}$)alkyl group; Z represents S, S(O)$_n$ where n represents 1–2, —S=NR, or —S(=O)=NR wherein R represents hydrogen or substituted or unsubstituted ($C_1$–$C_{10}$)alkyl; $Y^1$, $Y^2$ and $Y^3$ are the same or different and independently represent hydrogen, halogen, cyano, nitro, formyl, hydroxy, amino or substituted or unsubstituted groups selected from ($C_1$–$C_{10}$)alkyl, hydroxy($C_1$–$C_{10}$)alkyl, ($C_1$–$C_{10}$)alkoxy($C_1$–$C_{10}$)alkyl, ($C_1$–$C_{10}$)alkoxycarbonyl, carboxy($C_1$–$C_{10}$)alkyl, ($C_1$–$C_{10}$) alkylsulfonyl, ($C_1$–$C_{10}$)alkylcarbonylamino($C_1$–$C_{10}$)alkyl, arylcarbonylamino($C_1$–$C_{10}$)alkyl, ($C_1$–$C_{10}$) alkylcarbonyloxy($C_1$–$C_{10}$)alkyl, amino($C_1$–$C_{10}$)alkyl, mono($C_1$–$C_{10}$)alkylamino, di($C_1$–$C_{10}$)alkylamino, arylamino, ($C_1$–$C_{10}$)alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

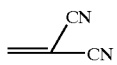

group; its tautomeric forms, it rotamers, its stereoisomers, its polymorphs, its pharmaceutically acceptable salts or its pharmaceutically acceptable solvates, which comprises:

(i) reacting the compound of formula (I)

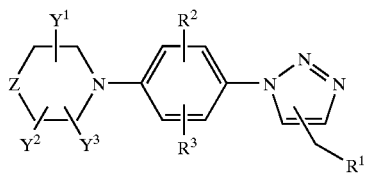

where $R^1$ repersents $NHR^4$, wherein $R^4$ represents —C(=S)—$NH_2$ and all other symbols are as defined above, with di tert-butoxy carbonyl ether [(BOC)$_2$O], to produce a compound of formula (I)

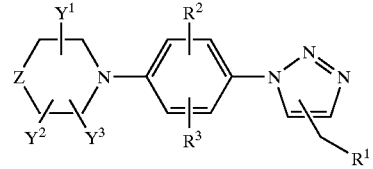

where $R^1$ represents $NHR^4$, wherein $R^4$ represents —C(=S)—$NH_2$ group substituted with tert-butoxy carbonyl group and all other symbols are as defined above and (ii) reacting the above compound of formula (I), with a compound of formula (Ij)

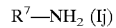

where $R^7$ represents substituted or unsubstituted ($C_1$–$C_{10}$)alkyl or aryl group, to produce a compound of formula (I) where $R^1$ represents $NHR^4$ where $R^4$ represents substituted or unsubstituted group selected from —C(=NH)—($C_1$–$C_{10}$)alkyl or —C(=NH)-aryl group and all other symbols are as defined above.

29. A process for the preparation of compound of formula (I)

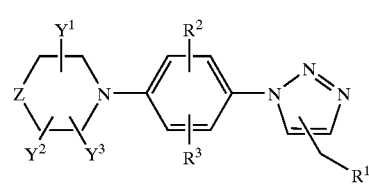

where $R^1$ represents halo, azido, thioalcohol, isothiocyanate, isoindole-1,3-dione, $NHR^4$, where $R^4$ represents hydrogen, substituted or unsubstituted groups selected from ($C_1$–$C_{10}$) alkyl, ($C_1$–$C_{10}$)acyl, thio($C_1$–$C_{10}$)acyl, ($C_1$–$C_{10}$) alkoxycarbonyl, ($C_3$–$C_{10}$)cycloalkoxythiocarbonyl, ($C_2$–$C_{10}$)alkenyloxycarbonyl, ($C_2$–$C_{10}$)alkenylcarbonyl, heteroaryl, aryloxycarbonyl, heteroarylcarbonyl, heteroarylthiocarbonyl, ($C_1$–$C_{10}$)alkoxythiocarbonyl, ($C_2$–$C_{10}$)alkenyloxythiocarbonyl, aryloxythiocarbonyl, —C(=O)—C(=O)—($C_1$–$C_{10}$)alkyl, —C(=O)—C(=O)-aryl, —C(=O)—C(=O)—($C_1$–$C_{10}$)alkoxy, —C(=O)—C(=O)-aryloxy, —C(=O)—C(=S)—($C_1$–$C_{10}$)alkyl, —C(=O)—C(=S)-aryl, —C(=S)—S—($C_1$–$C_{10}$)alkyl, —C(=S)—$NH_2$, —C(=S)—NH—($C_1$–$C_{10}$)alkyl, —C(=S)—N—(($C_1$–$C_{10}$)alkyl)$_2$, —C(=S)—NH—($C_2$–$C_{10}$)alkenyl, C(=S)—C(=O)—($C_1$–$C_{10}$)alkoxy, —C(=S)—C(=O)-aryloxy, —C(=S)—O—C(=O)—($C_1$–$C_{10}$)alkyl, C(=S)—C(=S)—($C_1$–$C_{10}$)alkyl, —C(=S)—C(=S)-aryl, —C(=S)—NH-C(=O)-aryl, —C(=S)—NH-aralkyl, —C(=S)—NH-heteroaralkyl, —C(=NH)—$NH_2$, —C(=NH)—($C_1$–$C_{10}$)alkyl, —C(=NH)-aryl, S(O)$_2$($C_1$–$C_{10}$)alkyl, S(O)$_2$aryl, thiomorpholinylthiocarbonyl, pyrrolidinylthiocarbonyl or —C(=S)—N(R'R''), where R' and R'' together form a substituted or unsubstituted 5 or 6 member heterocycle ring containing nitrogen and optionally having one or two additional hetero atoms selected from O, S or N; $OR^5$ where $R^5$ represents hydrogen, substituted or unstubstituted groups selected from ($C_1$–$C_{10}$)acyl, heteroaryl, S(O)$_2$($C_1$–$C_{10}$) alkyl, S(O)$_2$aryl or —C(=S)—S—($C_1$–$C_{10}$)alkyl; N($R^6$)$_2$, where —($R^6$)$_2$ together represent a substituted or unsubstituted 5 or 6 member heterocycle ring containing nitrogen and optionally having one or two additional hetero atoms selected from O, S or N; $R^2$ and $R^3$ are the same or different and independently represent hydrogen, halogen atom, substituted or unsubstituted $(C_1-C_{10})$alkyl group, halo$(C_1-C_{10})$alkyl, cyano, nitro, $SR^a$, $NR^a$, or $OR^a$ where $R^a$ represents substituted or unsubstituted $(C_1-C_{10})$alkyl group; Z represents $S(O)_n$ where n represents 1–2; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

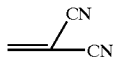

group; its tautomeric forms, it rotamers, its stereoisomers, its polymorphs, its pharmaceutically acceptable salts or its pharmaceutically acceptable solvates, which comprises: oxidizing the compound of formula (I) where Z represents 'S' and all other symbols are as defined above, by using m-chloroperoxybenzoic acid (m-CPBA) or hydrogen peroxide.

30. A process for the preparation of compound of formula (I)

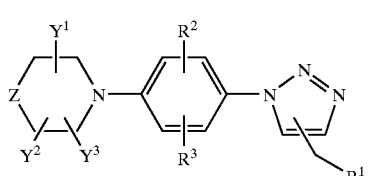

where $R^1$ represents halogen atom; $R^2$ and $R^3$ are the same or different and independently represent hydrogen, halogen atom, substituted or unsubstituted $(C_1-C_{10})$alkyl group, halo $(C_1-C_{10})$alkyl, cyano, nitro, $SR^a$, $NR^a$, or $OR^a$ where $R^a$ represents substituted or unsubstituted $(C_1-C_{10})$alkyl group; Z represents S, $S(O)_n$ where n represents 1–2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

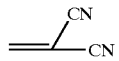

group; its tautomeric forms, it rotamers, its stereoisomers, its polymorphs, its pharmaceutically acceptable salts or its pharmaceutically acceptable solvates, which comprises: converting the compound of formula (I) where $R^1$ represents hydroxy group and all other symbols are as defined above, with $SOCl_2$, $PCl_5/PBr_3$, tetrahalomethane, in the presence of $PPh_3$ or $P(alkyl)_3$.

31. A process for the preparation of compound of formula (I)

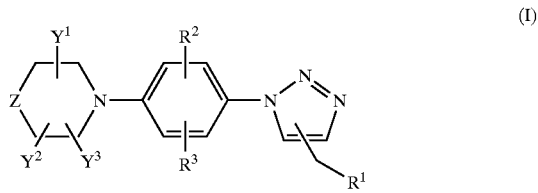

where $R^1$ represents 'SH' group; $R^2$ and $R^3$ are the same or different and independently represent hydrogen, halogen atom, substituted or unsubstituted $(C_1-C_{10})$alkyl group, halo $(C_1-C_{10})$alkyl, cyano, nitro, $SR^a$, $NR^a$, or $OR^a$ where $R^a$ represents substituted or unsubstituted $(C_1-C_{10})$alkyl group; Z represents S, $S(O)_n$ where n represents 1–2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_1)$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

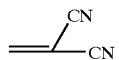

group; its tautomeric forms, it rotamers, its stereoisomers, its polymorphs, its pharmaceutically acceptable salts or its pharmaceutically acceptable solvales, which comprises:
(i) reacting the compound of formula (I) where $R^1$ represents halogen atom, to produce a compound of formula (Ih),

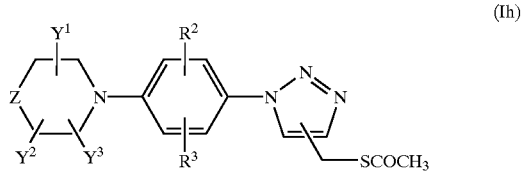

where all other symbols are as defined above, with a base and thiolacetic acid,
(ii) reacting the compound of formula (Ih), to produce a compound of formula (I) where $R^1$ represents SH group and all other symbols are as defined above, with base.

32. A pharmaceutical composition comprising a compound of formula (I)

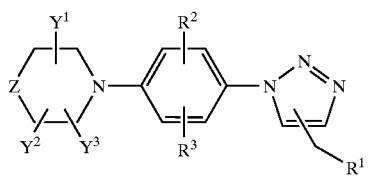
(I)

as claimed in claim 1 and a pharmaceutically acceptable carrier, diluent, excipient or solvate.

33. The pharmaceutical composition as claimed in claim 32, in the form of a tablet, capsule, powder, syrup, solution or suspension.

34. A method of treating a bacterial infection comprising administering an effective amount of a compound of formula (I) as claimed in claim 1 to a patient in need thereof.

35. A method of treating a bacterial infection comprising administering an effective amount of a pharmaceutical composition as claimed in claim 32 or 33 to a patient in need thereof.

36. A composition comprising a compound as claimed in claim 6 and a pharmaceutically acceptable carrier, diluent, excipient or solvate.

37. The pharmaceutical composition as claimed in claim 36, in the form of a tablet, capsule, powder, syrup, solution or suspension.

38. A method of treating a bacterial infection comprising administering an effective amount of a compound as claimed in claim 6 to a patient in need thereof.

39. A method of treating a bacterial infection comprising administering an effective amount of a composition as claimed in claim 36 or 37 to a patient in need thereof.

40. A compound of formula (Ie)

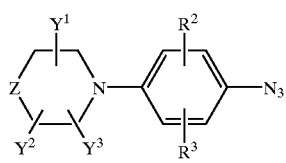
(Ie)

where $R^2$ and $R^3$ are the same or different and independently represent hydrogen, halogen atom, substituted or unsubstituted $(C_1–C_{10})$alkyl group, halo$(C_1–C_{10})$alkyl, cyano, nitro, $SR^a$, $NR^a$, or $OR^a$ where $R^a$ represents substituted or unsubstituted $(C_1–C_{10})$alkyl group; Z represents S, $S(O)_n$ where n represents 1–2, —S=NR, or —S(=O)=NR wherein R represents hydrogen or substituted or unsubstituted $(C_1–C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1–C_{10})$alkyl, hydroxy$(C_1–C_{10})$alkyl, $(C_1–C_{10})$alkoxy$(C_1–C_{10})$alkyl, $(C_1–C_{10})$alkoxycarbonyl, carboxy$(C_1–C_{10})$alkyl, $(C_1–C_{10})$alkylsulfonyl, $(C_1–C_{10})$alkylcarbonylamino$(C_1–C_{10})$alkyl, arylcarbonylamino$(C_1–C_{10})$alkyl, $(C_1–C_{10})$alkylcarbonyloxy$(C_1–C_{10})$alkyl, amino$(C_1–C_{10})$alkyl, mono$(C_1–C_{10})$alkylamino, di$(C_1–C_{10})$alkylamino, arylamino, $(C_1–C_{10})$alkoxy, aryl, aryloxy, aralkyl, heteroaryl, heteroaralkyl, heterocyclyl or heterocloalkyl; or any one or two of $Y^1$, $Y^2$ or $Y^3$ represent =O, =S, substituted or unsubstituted =NOH; or

group.

41. A process for the preparation of compound of formula (Ie), as claimed in claim 40

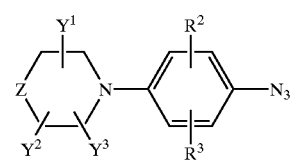
(Ie)

where Z, $Y^1$, $Y^2$, $Y^3$, $R^2$ and $R^3$ are as defined in claim 40, which comprises the steps of:

(i) reacting the compound of formula (Ia)

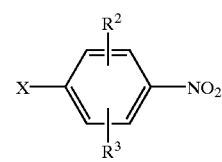
(Ia)

where X represents halogen atom; $R^2$ and $R^3$ are as defined in claim 40, with a compound of formula (Ib)

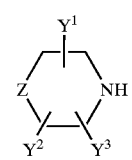
(Ib)

where Z, $Y^1$, $Y^2$ and $Y^3$ are as defined in claim 40, to produce a compound of formula (Ic)

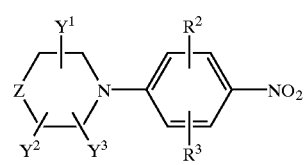
(Ic)

where Z, $Y^1$, $Y^2$, $Y^3$, $R^2$ and $R^3$ are as defined in claim 40, (ii) reducing the compund of formula (Ic) by using reducing agent to a compound of formula (Id)

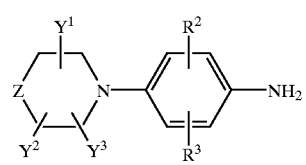
(Id)

where Z, $Y^1$, $Y^2$, $Y^3$, $R^2$ and $R^3$ are as defined in claim 40, and (iii) converting the compound of formula (Id) to a compound of formula (Ie)

(Ie)

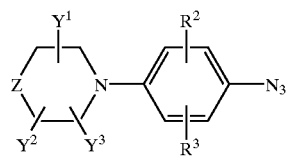

where Z, $Y^1$, $Y^2$, $Y^3$, $R^2$ and $R^3$ are as defined in claim 40.

42. A compound of formula (If)

(If)

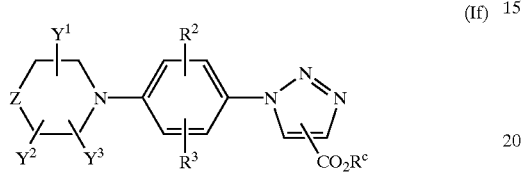

where $R^c$ represents substituted or unsubstituted ($C_1$–$C_{10}$) alkyl group; $R^2$ and $R^3$ are the same or different and independently represent hydrogen, halogen atom, substituted or unsubstituted ($C_1$–$C_{10}$)alkyl group, halo($C_1$–$C_{10}$)alkyl, cyano, nitro, $SR^a$, $NR^a$, or $OR^a$ where $R^a$ represents substituted or unsubstituted ($C_1$–$C_{10}$)alkyl group; Z represents S, $S(O)_n$ where n represents 1–2, —S=NR, or —S(=O)=NR wherein R represents hydrogen or substituted or unsubstituted ($C_1$–$C_{10}$)alkyl; $Y^1$, $Y^2$ and $Y^3$ are the same or different and independently represent hydrogen, halogen, cyano, nitro, formyl, hydroxy, amino or substituted or unsubstituted groups selected from ($C_1$–$C_{10}$)alkyl, hydroxy($C_1$–$C_{10}$)alkyl, ($C_1$–$C_{10}$)alkoxy($C_1$–$C_{10}$)alkyl, ($C_1$–$C_{10}$)alkoxycarbonyl, carboxy($C_1$–$C_{10}$)alkyl, ($C_1$–$C_{10}$)alkylsulfonyl, ($C_1$–$C_{10}$)alkylcarbonylamino($C_1$–$C_{10}$)alkyl, arylcarbonylamino($C_1$–$C_{10}$)alkyl, ($C_1$–$C_{10}$)alkylcarbonyloxy($C_1$–$C_{10}$)alkyl, amino($C_1$–$C_{10}$)alkyl, mono($C_1$–$C_{10}$)alkylamino, di($C_1$–$C_{10}$)alkylamino, arylamino, ($C_1$–$C_{10}$)alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

group.

43. A process for the preparation of compound of formula (If), as claimed in claim 42

(If)

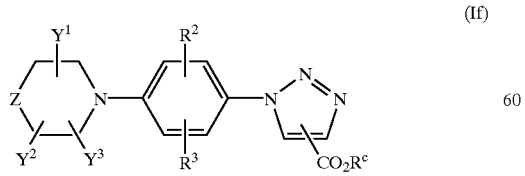

where Z, $Y^1$, $Y^2$, $Y^3$, $R^c$, $R^2$ and $R^3$ are as defined in claim 42, which comprises the steps of:

(i) reacting the compound of formula (Ia)

(Ia)

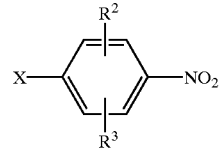

where X represents halogen atom; $R^2$ and $R^3$ are as defined in claim 42, with a compound of formula (Ib)

(Ib)

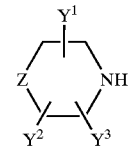

where Z, $Y^1$, $Y^2$ and $Y^3$ are as defined in claim 42, to produce a compound of formula (Ic)

(Ic)

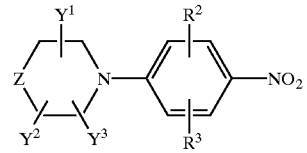

where Z, $Y^1$, $Y^2$, $Y^3$, $R^2$ and $R^3$ are as defined in claim 42, (ii) reducing the compund of formula (Ic)

(Id)

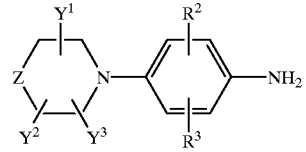

where Z, $Y^1$, $Y^2$, $Y^3$, $R^2$ and $R^3$ are as defined in claim 42, by using reducing agent to a compound of formula (Id)

(iii) converting the compound of formula (Id)

(Ie)

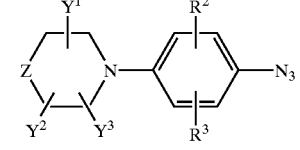

where Z, $Y^1$, $Y^2$, $Y^3$, $R^2$ and $R^3$ are as defined in claim 42, to a compound of formula (Ie) and (iv) converting the compound of formula (Ie)

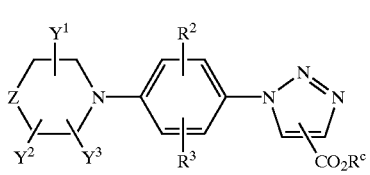
(If)

where Z, $Y^1$, $Y^2$, $Y^3$, $R^c$, $R^2$ and $R^3$ are as defined in claim 42, to a compound of formula (If).

44. A compound of formula (Ig)

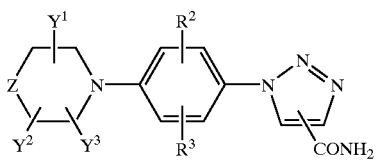
(Ig)

where $R^2$ and $R^3$ are the same or different and independently represent hydrogen, halogen atom, substituted or unsubstituted $(C_1-C_{10})$alkyl group, halo$(C_1-C_{10})$alkyl, cyano, nitro, $SR^a$, $NR^a$, or $OR^a$ where $R^a$ represents substituted or unsubstituted $(C_1-C_{10})$alkyl group; Z represents S, $S(O)_n$ where n represents 1–2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino $(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

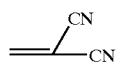

group.

45. A process for the preparation of compound of formula (Ig), as claimed in claim 44

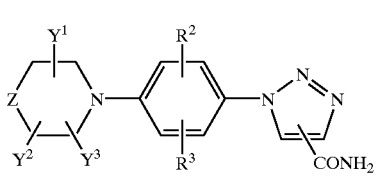
(Ig)

where Z, $Y^1$, $Y^2$, $Y^3$, $R^2$ and $R^3$ are as defined in claim 44, which comprises the steps of:

(i) converting a compound of formula (If)

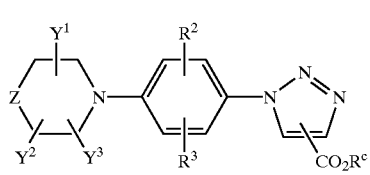
(If)

where $R^c$ represents substituted or unsubstituted $(C_1-C_6)$ alkyl group and all other symbols are as defined in claim 44, to produce a compound of formula (Ig), where all symbols are as defined in claim 44.

46. A compound of formula (Ij)

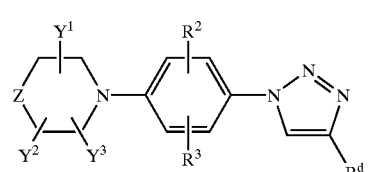
(Ij)

where $R^d$ represents substituted or unsubstituted groups selected from —$(C_1-C_{10})$alkyl, —$CO_2R^c$, —$CH_2OH$, —$CH_2NH_2$, —$CH_2N$(Pthalimide), —$CH_2NH$—C(=S)S—O$(C_1-C_{10})$alkyl or —$CH_2NH$—C(=O)—$(C_1-C_{10})$alkyl where $R^c$ is substituted or unsubstituted $(C_1-C_{10})$alkyl; $R^2$ and $R^3$ are the same or different and independently represent hydrogen, halogen atom, substituted or unsubstituted $(C_1-C_{10})$alkyl group, halo$(C_1-C_{10})$alkyl, cyano, nitro, $SR^a$, $NR^a$, or $OR^a$ where $R^1$ represents substituted or unsubstituted $(C_1-C_{10})$alkyl group; Z represents S, $S(O)_n$ where n represents 1–2, —S=NR, or —S(=O)=NR wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino $(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent =O, =S, substituted or unsubstituted =NOH; or

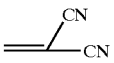

group.

47. A process for the preparation of compound of formula (Ij), as claimed in claim 46,

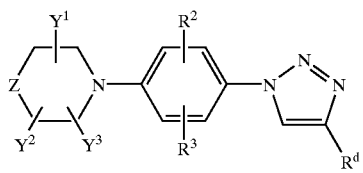

(Ij)

where Z, $Y^1$, $Y^2$, $Y^3$, $R^2$, $R^3$ and $R^d$ are as defined in claim 46, which comprises the steps of:
(i) converting the compound of formula (Ie),

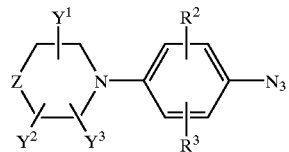

(Ie)

where Z, $Y^1$, $Y^2$, $Y^3$, $R^2$ and $R^3$ are as defined in claim 46, with $$\equiv\!\!-\!R^d$$ (Ih)

where $R^d$ is as defined in claim 46, to a compound of formula (Ij)

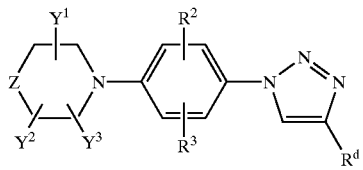

(Ij)

where Z, $Y^1$, $Y^2$, $Y^3$, $R^d$, $R^2$ and $R^3$ are as defined in claim 46.

48. A process for the preparation of compound of formula (I)

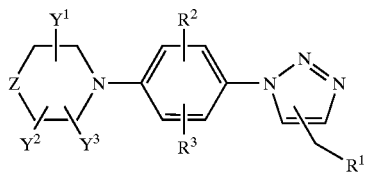

(I)

where $R^1$ represent $NHR^4$ wherein $R^4$ represents substituted or unstubstituted $-S(O)_2(C_1-C_{10})$alkyl or $-S(O)_2$aryl group; $R^2$ and $R^3$ are the same or different and independently represent hydrogen, halogen atom, substituted or unsubstituted $(C_1-C_{10})$alkyl group, halo$(C_1-C_{10})$alkyl, cyano, nitro, $SR^a$, $NR^a$, or $OR^a$ where $R^a$ represents substituted or unsubstituted $(C_1-C_{10})$alkyl group; Z represents S, $S(O)_n$ where n represents 1–2, $-S=NR$, or $S(=O)=NR$ wherein R represents hydrogen or substituted or unsubstituted $(C_1-C_{10})$alkyl; $Y^1$, $Y^2$ and $Y^3$ are the same or different and independently represent hydrogen, halogen, cyano, nitro, formyl, hydroxy, amino or substituted or unsubstituted groups selected from $(C_1-C_{10})$alkyl, hydroxy$(C_1-C_{10})$alkyl, $(C_1-C_{10})$alkoxy$(C_1-C_{10})$alkyl, $(C_1-C_{10})$alkoxycarbonyl, carboxy$(C_1-C_{10})$alkyl, $(C_1-C_{10})$alkylsulfonyl, $(C_1-C_{10})$alkylcarbonylamino$(C_1-C_{10})$alkyl, arylcarbonylamino$(C_1-C_{10})$alkyl, $(C_1-C_{10})$alkylcarbonyloxy$(C_1-C_{10})$alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; or any one or two of $Y^1$, $Y^2$ or $Y^3$ represent $=O$, $=S$, substituted or unsubstituted $=NOH$; or

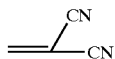

group; its tautomeric forms, it rotamers, its stereoisomers, its polymorphs, its pharmaceutically acceptable salts or its pharmaceutically acceptable solvates, which comprises: reacting the compound of formula (I), where $R^1$ represents $NHR^4$ where $R^4$ represents hydrogen atom and all other symbols are as defined above, by treating with alkylsulfonylchloride or arylsulfonylchloride.

49. A method for treating a microbial infection comprising administering an effective amount of a compound of formula I as defined in claim 1 to a patient in need thereof wherein the microbial infection is caused by a gram-positive aerobic bacteria, anaerobic organism, acid-fast organism or gram-negative bacteria.

50. A method for preventing a microbial infection in a patient at risk for developing a bacterial infection comprising administering an effective amount of a compound of formula I as defined in claim 1 to a patient in need thereof wherein the microbial infection is caused by a gram-positive aerobic bacteria, anaerobic organism, acid-fast organism or gram-negative bacteria.

51. A method for treating a microbial infection comprising administering an effective amount of a compound of formula I as defined in claim 6 to a patient in need thereof wherein the microbial infection is caused by a gram-positive aerobic bacteria, anaerobic organism, acid-fast organism or gram-negative bacteria.

52. A method for preventing a microbial infection in a patient at risk for developing a bacterial infection comprising administering an effective amount of a compound of formula I as defined in claim 6 to a patient in need thereof wherein the microbial infection is caused by a gram-positive aerobic bacteria, anaerobic organism, acid-fast organism or gram-negative bacteria.

53. A composition comprising a compound as claimed in claim 7 and a pharmaceutically acceptable carrier, diluent, excipient or solvate.

54. The pharmaceutical composition as claimed in claim 53, in the form of a tablet, capsule, powder, syrup, solution or suspension.

55. A method of treating a bacterial infection comprising administering an effective amount of a compound as claimed in claim 7 to a patient in need thereof.

56. A method of treating a bacterial infection comprising administering an effective amount of a composition as claimed in claim 53 or 54 to a patient in need thereof.

* * * * *